United States Patent
Zheng et al.

(10) Patent No.: US 9,453,022 B2
(45) Date of Patent: Sep. 27, 2016

(54) USE OF SMALL MOLECULE INHIBITORS TARGETING THE INTERACTION BETWEEN RAC GTPASE AND P67 (PHOX)

(71) Applicant: CHILDREN'S HOSPITAL MEDICAL CENTER, Cincinnati, OH (US)

(72) Inventors: Yi Zheng, Cincinnati, OH (US); Prakash Jagtap, North Andover, MA (US); Emily E. Bosco, North Potomac, MD (US); Jaroslaw Meller, Cincinnati, OH (US); Marie-Dominique Filippi, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 14/378,089

(22) PCT Filed: Feb. 13, 2013

(86) PCT No.: PCT/US2013/025977
§ 371 (c)(1),
(2) Date: Aug. 11, 2014

(87) PCT Pub. No.: WO2013/123081
PCT Pub. Date: Aug. 22, 2013

(65) Prior Publication Data
US 2015/0025067 A1 Jan. 22, 2015

Related U.S. Application Data

(60) Provisional application No. 61/598,822, filed on Feb. 14, 2012.

(51) Int. Cl.
| | | |
|---|---|---|
| C07D 491/052 | (2006.01) | |
| C07D 498/04 | (2006.01) | |
| C07D 215/36 | (2006.01) | |
| C07D 215/38 | (2006.01) | |
| C07D 215/48 | (2006.01) | |
| C07D 409/04 | (2006.01) | |
| C07D 401/04 | (2006.01) | |
| A61K 31/473 | (2006.01) | |
| A61K 31/4738 | (2006.01) | |
| A61K 31/5365 | (2006.01) | |
| A61K 31/5377 | (2006.01) | |
| C07D 221/16 | (2006.01) | |
| C07D 491/04 | (2006.01) | |
| C07D 215/06 | (2006.01) | |
| C07D 491/048 | (2006.01) | |

(52) U.S. Cl.
CPC ......... *C07D 491/052* (2013.01); *A61K 31/473* (2013.01); *A61K 31/4738* (2013.01); *A61K 31/5365* (2013.01); *A61K 31/5377* (2013.01); *C07D 215/06* (2013.01); *C07D 215/36* (2013.01); *C07D 215/38* (2013.01); *C07D 215/48* (2013.01); *C07D 221/16* (2013.01); *C07D 401/04* (2013.01); *C07D 409/04* (2013.01); *C07D 491/04* (2013.01); *C07D 491/048* (2013.01); *C07D 498/04* (2013.01)

(58) Field of Classification Search
CPC ............ C07D 491/052; C07D 498/04; C07D 215/36; C07D 215/38; C07D 215/48; C07D 409/04; C07D 401/04
USPC ........ 546/61, 74, 79, 89; 514/284, 289, 290, 514/291
See application file for complete search history.

(56) References Cited

U.S. PATENT DOCUMENTS

| | | | |
|---|---|---|---|
| 6,051,601 | A | 4/2000 | Dombroski et al. |
| 7,465,727 | B2 | 12/2008 | Tahri et al. |
| 2008/0167334 | A1 | 7/2008 | Prossnitz et al. |
| 2008/0221118 | A1 | 9/2008 | Staehle et al. |
| 2008/0287414 | A1 | 11/2008 | Bergman et al. |
| 2011/0178077 | A1* | 7/2011 | Brodin et al. ............. 514/233.2 |

FOREIGN PATENT DOCUMENTS

| | | |
|---|---|---|
| WO | WO 01/17533 | 3/2001 |
| WO | WO 2004/072046 | 8/2004 |
| WO | WO 2011/009523 A1 | 1/2011 |
| WO | WO 2013/123081 A2 | 8/2013 |

OTHER PUBLICATIONS

Edwards et al. Molecular Pharmacology (2005), 68(5), 1301-1310.*
Bosco, E et al., "Rational design of small molecule inhibitors targeting the Rac GTPase—p67*phox* signaling axis in inflammation," *Chem Biol.*, Feb. 24, 2012, 9(2): 228-242.
Rognan, D., "Chemogenomic approaches to rational drug design," *Brit J Pharmacol.*, 2007, 152: 38-52.
International Search Report and Written Opinion mailed Apr. 26, 2013, issued in International Application No. PCT/US2013/025977, filed Feb. 13, 2013.
Bosco, Emily E. et al., RAC1 Targeting Suppresses P53 Deficiency-Mediated Lymphomagnesis, Blood, Apr. 22, 2010, 115(16), pp. 3320-3328.
Das, Biswanath et al., Tungstophosphoric Acid-Catalyzed Imino-Diels-Alder Reaction: An Efficient One-Pot Synthesis of Pyrano- and Furanoquinolines Derivatives, Synthetic Communications, 39, 2009, pp. 3825-3832.
Filippi, Marie-Dominique et al., Localization of Rac2 via the C Terminus and Aspartic Acid 150 Specifies Superoxide Generation, Actin Polarity and Chemotaxis in Neutrophils, Nature Immunology, vol. 5, No. 7, Jul. 2004, pp. 744-751.
Goudar, Mahesh A. et al, Imino Diels-Alder Reactions: Efficient Synthesis of Pyrano and Furanoquinolines Catalyzed by Antimony (III) Sulfate, Letters in Organic Chemistry, 2008, 5, pp. 628-632.
Li, Jianjun et al., Proline Triflate Catalysed Diels-Alder Reaction in the Synthesis of Tetrahydroquinoline Derivatives, Journal of Chemical Research, Aug. 2009, pp. 499-504.

(Continued)

*Primary Examiner* — Kahsay Habte
(74) *Attorney, Agent, or Firm* — Knobbe Martens Olson & Bear LLP

(57) ABSTRACT

Inhibitors of p67$^{phox}$ protein are provided herein, as well as pharmaceutical compositions and methods recited thereto.

14 Claims, 36 Drawing Sheets

(56) References Cited

OTHER PUBLICATIONS

Mahajan, Deepali et al., Antimony Chloride Doped on Hydroxyapetite Catalyzed Stereoselective One-Pot Synthesis of Pyrano[3,2-C]Quinolines, Tetrahedron Letters 47, 2006, pp. 7919-7921.

Mahesh, M. et al., Imino Diels-Alder Reactions: Efficient Synthesis of Pyrano and Furoquinolines Catalyzed by ZrCl4, Synthetic Communication, vol. 34, No. 22, 2004, pp. 4089-4104.

Nagaiah, K. et al, Phosphomolybdic Acid-Catalyzed Efficient One-Pot Three-Component Asa-Diels-Alder Reaction Under Solvent-Free Conditions: A Facile Synthesis of Trans-Fused Pyrano- and Furanotetrahydroquinolines, Tetrahedron Letters 47, 2006, pp. 4409-4413.

Nagarapu, Lingaiah et al., Tin(II)Chloride Catalyzed Synthesis of Pyranoquinolines, Phenanthridinone and Phenanthridine Derivatives, European Journal of Chemistry, 2011 2(2), pp. 260-265.

Narsaiah, Venkat A.et al, Samarium Triflate as Mild and Efficient Catalyst for Aza-Diels-Alder Reaction: A Facile Synthesis of Cis-Fused Pyrano- and Furanoquinolines, Synthetic Communications, 40, 2010, pp. 1750-1757.

Oh, Hana et al., Video Article: Neutrophil Isolation Protocol, Journal of Visualized Experiments, 17, 2008, p. 745.

Orlov, V.D. et al., Substituted 1,10B-Dihydro-5H-Pyrazolo[1,5-C]-1,3-Benzoxazines, Translated from Khimiya Geterotsiklicheskikh Soedinenii, No. 8, pp. 1131-1136, Aug. 1991.

Ravikumar, K. et al., Imino Diels-Alder Adducts. XII. Two Pyranol[3,2-C]Quinolines, Acta Crystallographica Section C: Crystal Structure Communications, 2006, C62, pp. 574-576.

Salehi, Javad. et al., One-Pot Synthesis of Pyrano- and Furanoquinolines Catalyzed by Molten Tetra-N-Butylophosphonium Bromide Under Solvent-Free Conditions, Journal of Hetrocyclic Chemistry,48(2) , Mar. 2011, pp. 484-488.

Servant, Guy et al., Dynamics of a Chemoattractant Receptor in Living Neutrophils During Chemotaxis, Molecular Biology of the Cell, vol. 10, Apr. 1999, pp. 1163-1178.

Srinivasa, A. et al., Imino Diels-Alder Reactions: Efficient Synthesis of Pyrano- and Furanoquinolines Catalyzed by 4-Nitrophthalic Acid, Monatshefte fur Chemie (Chemical Monthly), 139, 2008, pp. 141-145.

Svetlik, Jan et al. Synthesis of Some Pyrazolo [1,5-C][1,3]Benzoxazines and a New 5H-Pyrazolo[1,5-C][1,3,2]Benzoxazaphosphorine Ring Systems, Journal of Heterocyclic Chemistry, 42, (2005), pp. 1143-1147.

Wind, S. et al., Comparative Pharmacology of Chemically Distinct Nadph Oxidase Inhibitors, British Journal of Pharmacology, 2010, pp. 885-898.

Yadav, J.S. et al, Aza-Diels-Alder Reactions in Ionic Liquids: A Facile Synthesis of Pyrano- and Furanoquinolines, Tetrahedron 59, 2003, pp. 1599-1604.

Yadav, J.S. et al., Novel Use of Selectfluor™ for the Synthesis of Cis-Fused Pyrano- and Furanotetrahydroquinolines, Advanced Synthesis and Catalysis, 2003, 34, pp. 1203.1206.

Yu, Yong et al., Stereoselective Synthesis of Pyrano[3,2-C]- and Furano[3,2-C]Quinolines: Gadolinium Chloride Catalyzed One-Pot Aza-Diels-Alder Reactions, Heteroatom Chemistry, 2010, 21(5), pp, 351-354.

Zhou, Zhuqing et al., Stereoselective Synthesis of Pyrano[3,2-C]- and Furano[3,2-C]Quinolines: Samarium Diiodide-Catalyzed One-Pot Aza-Diels-Alder Reactions, European Journal of Organic Chemistry, 2007, pp. 5265-5269.

Canadian Office Action in Canadian Application No. 2864331, filed Aug. 11, 2014, dated Apr. 7, 2016.

Extended European Search Report with the Communication pursuant to Rules 70(2) and 70a(2) EPC in European Patent Application No. 13749793.9, filed Aug. 21, 2014, dated May 4, 2016.

"Small Molecule targeting of NADPH oxidase in neutrophils SBIR.gov", Jan. 1, 2010, XP055260588, Retrieved from the Internet: URL: https//www.sbir.gov.sbirsearch/detail/378569.

* cited by examiner

| FIG. 3A-1 | FIG. 3A-2 |

FIG. 3A

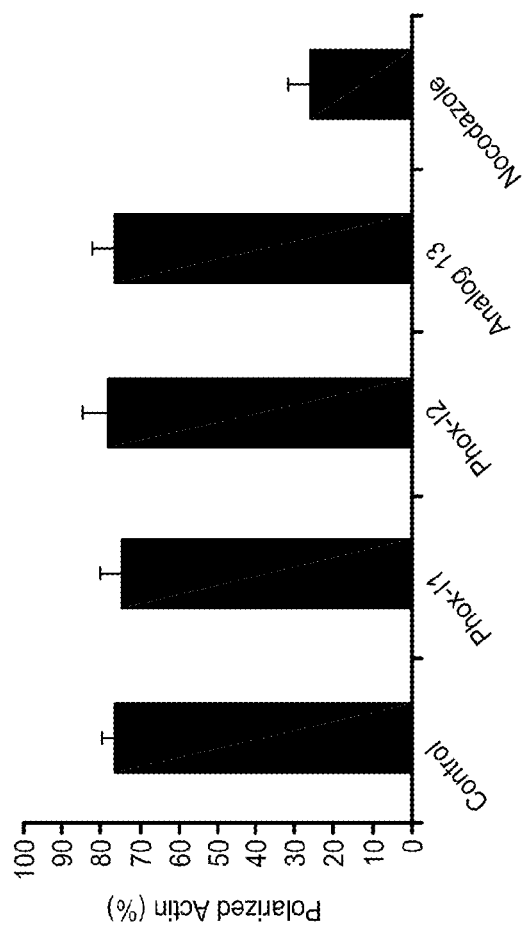
FIG. 4C
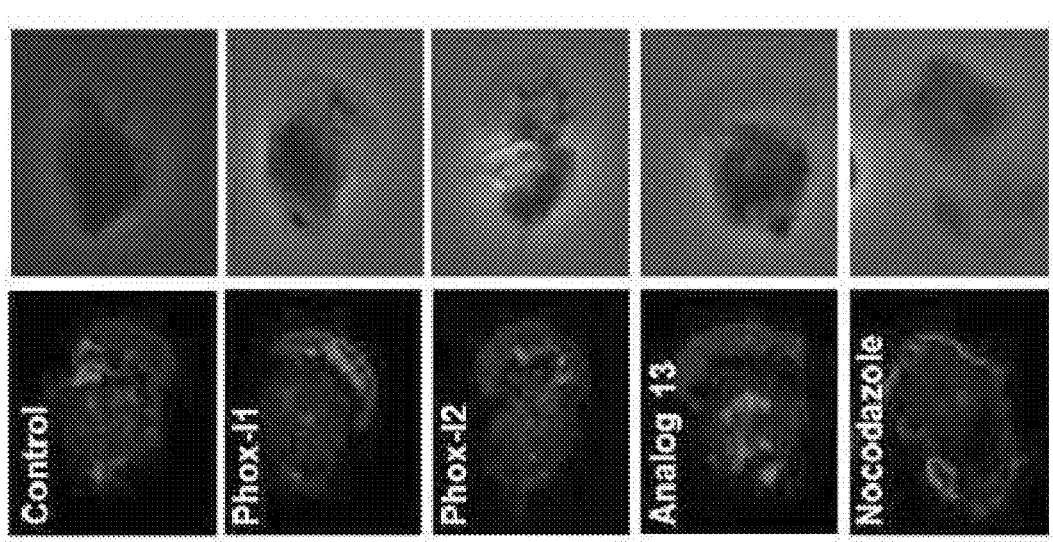

USE OF SMALL MOLECULE INHIBITORS TARGETING THE INTERACTION BETWEEN RAC GTPASE AND P67 (PHOX)

Any and all priority claims identified in the Application Data Sheet, or any correction thereto, are hereby incorporated by reference under 37 CFR 1.57. For example, this application is a U.S. National Phase of International Application No. PCT/US2013/025977, filed on Feb. 13, 2013 designating the U.S. and published on Aug. 22, 2013 as WO 2013/123081, which claims the benefit of and priority to U.S. Provisional Application No. 61/598,822, filed Feb. 14, 2012, the disclosure of which is hereby expressly incorporated by reference in its entirety.

STATEMENT REGARDING FEDERALLY SPONSORED R&D

This invention was made with government support under HL099244, CA141341, and HL091805 awarded by the National Institutes of Health. The government has certain rights in the invention.

BACKGROUND

1. Field

The subject matter provided herein relates to inhibition of $p67^{phox}$ protein; in particular compounds, compositions and methods relating to inhibition of $p67^{phox}$ protein.

2. Description of the Related Technology

The multicomponent nicotinamide adenine dinucleotide phosphate (NADPH) oxidase NOX2 enzyme complex facilitates the production of reactive oxygen species (ROS) to mediate innate immunity. NADPH oxidase-dependent processes occur in many different cell types for both host defense and intracellular signal transduction. Inappropriate regulation of the NADPH oxidase complex has been proposed to contribute to a multitude of inflammation-mediated disorders. Biochemical studies have identified a molecular mechanism of NOX2 regulation; its activation is dependent on a series of protein interactions that are initiated in the cytoplasm and translocate to the cell membrane for full NADPH oxidase complex activation. In response to inflammatory stimuli, four cytosolic proteins in the "regulatory complex," that is, Rac1/2, $p47^{phox}$, $p67^{phox}$ and $p40^{phox}$, are translocated to the membrane, where they interact with the plasma membrane-bound NOX2 and $p22^{phox}$ subunits. One limiting step in the assembly of this active NADPH oxidase complex is the binding of p67phox to the activated, GTP-bound Rac1 and/or Rac2. The binding of $p67^{phox}$ to Rac1/2-GTP allows for the complete assembly of the complex and activation of NOX2 NADPH oxidase.

SUMMARY

Provided are compounds, compositions and methods relating to the inhibition to $p67^{phox}$. The compounds, compositions and methods provided herein include a compound having the structure of Formula I:

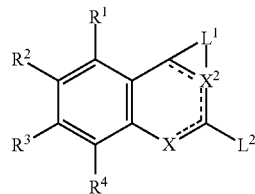

I or a pharmaceutically acceptable salt thereof, wherein:

$L^1$ is selected from the group consisting of $C_{3-6}$ alkyl, $C_{3-6}$ alkenyl, $C_{2-5}$ alkoxy, $C_{1-5}$ heteroalkyl, $-CH_2-C(R^{10})=N-$, $C_{5-6}$ cycloalkyl, $C_{5-6}$ cycloalkenyl, and arylalkyl, each optionally substituted with one or more $R^{1A}$;

$R^{10}$ is hydrogen or $R^{1A}$;

$L^2$ is aryl or heteroaryl each optionally substituted with one or more with one or more $R^{2A}$;

each $R^{1A}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro, said aryl, heteroaryl, heterocyclyl, arylalkyl, heteroarylalkyl, heterocyclylalkyl, cycloalkyl, cycloalkenyl, and (cycloalkyl)alkyl in the definition of $R^{1A}$ are each optionally substituted with one or more $R^{1AA}$;

each $R^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, $(C_1-C_6)$alkyl optionally substituted with up to 5 fluoro, and $(C_1-C_6)$alkoxy optionally substituted with up to 5 fluoro;

each $R^{2A}$ is independently selected from the group consisting of hydroxy, halo, cyano, nitro, $-S(O)_zNR^{1B}R^{1C}$, $-NHS(O)_zNR^{1B}R^{1C}$, $-OC(=O)NR^{1B}R^{1C}$, $-NHC(=O)NR^{1B}R^{1C}$, $-C(=O)NR^{1B}R^{1C}$, $-NR^{1B}R^{1C}$, $-S(O)_zR^{1D}$, $-NHS(O)_zR^{1D}$, $-NHC(=O)R^{1D}$, $-OC(=O)R^{1D}$, $-C(=O)R^{1D}$, $-C(=O)OR^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$alkoxy optionally substituted with up to 5 fluoro;

$R^1$, $R^2$, $R^3$, and $R^4$ are each independently selected from the group consisting of hydrogen, hydroxy, halo, cyano, nitro, $-S(O)_zNR^{1B}R^{1C}$, $-NHS(O)_zNR^{1B}R^{1C}$, $-OC(=O)NR^{1B}R^{1C}$, $-NHC(=O)NR^{1B}R^{1C}$, $-C(=O)NR^{1B}R^{1C}$, $-NR^{1B}R^{1C}$, $-S(O)_zR^{1D}$, $-NHS(O)_zR^{1D}$, $-NHC(=O)R^{1D}$, $-OC(=O)R^{1D}$, $-C(=O)R^{1D}$, $-C(=O)OR^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$alkoxy optionally substituted with up to 5 fluoro;

each $NR^{1B}R^{1C}$ is independently selected, wherein $R^{1B}$ and $R^{1C}$ are each independently from the group consisting of hydrogen, $C_{1-6}$alkyl, aryl, arylalkyl, cycloalkyl, (cycloalkyl)alkyl, $(R^{1BB}R^{1CC}N)$alkyl, and $(R^{1BB}R^{1CC}N)C(=O)-$;

each $R^{1D}$ is independently selected from the group consisting of hydroxy, aryl, heteroaryl, heterocyclyl, arylalkyl, cycloalkyl, cycloalkenyl, (cycloalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro;

each $R^{1BB}R^{1CC}N$ is independently selected, wherein $R^{1BB}$ and $R^{1CC}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

X is O (oxygen), S (sulfur), N (nitrogen) or $NR^{11}$;

each z is independently 0, 1 or 2;

$R^{11}$ is H (hydrogen) or $C_{1-6}$ alkyl;

$X^2$ is C (carbon), $CR^{12}$, or N (nitrogen);

$R^{12}$ is H (hydrogen) or $C_{1-6}$ alkyl; and each dashed line is an optional double bond.

BRIEF DESCRIPTION OF THE DRAWINGS

FIGS. 4A-G set forth data demonstrating that Phox-I1 and Phox-I2 show undetectable toxicity and site effects. (A) Apoptosis analysis by FACS of HL-60 cells treated with compound or vehicle control for 2 hours prior to 7-AAD and Annexin V staining. (B) HL-60 cells from A were harvested and lysates were immunoblotted for levels of pPAK, and actin was used as a control for loading. (C) F-actin reorganization in freshly isolated fMLP-stimulated primary murine neutrophils was analyzed. Representative images (left panel) and quantification (right panel) are displayed. Treatment with Analog 13 is included as a "dead analog" that possesses no intrinsic ROS inhibitory activity, and nocodazole is included as a positive control for actin disruption. Cells were exposed to a 10 μM dose of Phox-I1, Phox-I2, and Analog 13, and 200 nM nocodazole. (D) The effect of Phox-I on NOX4 mediated ROS production was tested in primary murine neutrophils transfected with a NOX4 expressing plasmid. 10 μM Phox-I1 was applied to the cells for 30 min prior to ROS assay by luminol chemiluminescence in the presence of HRP. The fMLP-stimulated ROS activity in the presence or absence of 10 uM Phox-I1 was measured in parallel. (E) The antioxidant abilities of these lead compounds were tested by prestimulating dHL-60 cells with fMLP for 30 minutes prior to treatment with Phox-I1 or Phox-I2. Levels of superoxide were analyzed by DCFDA assay and FACS. NAC, apocyanin, DPI, and NSC23766 treated cells served as controls. (F) For affinity assay, DMSO-differentiated HL-60 cells were treated with standard effective dose of indicated compound for 2 hours, washed, and allowed to recover in normal media for 4 hours or 2 hours prior to fMLP stimulation and DCFDA ROS production assay by FACS analysis. (G) For stability assay, DMSO-differentiated HL-60 cells were treated with 20 μM dose of compound for the indicated time period prior to fMLP stimulation and DCFDA ROS production assay by FACS analysis. 30 minute and 18 hour time periods are not displayed because they revealed no ROS inhibition.

DETAILED DESCRIPTION

Figure 1A:
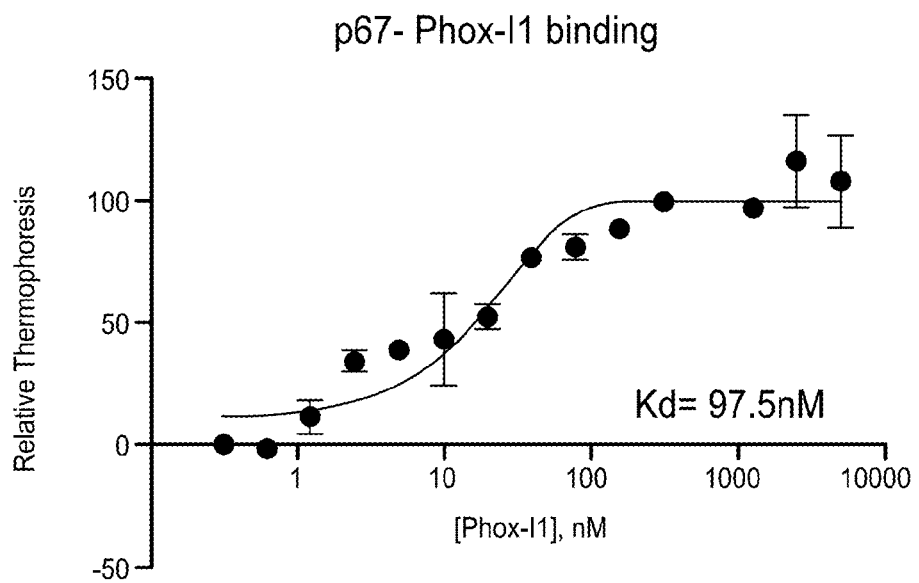
FIGS. 1A-G set forth the results of microscale thermophoresis demonstrating binding affinity and specificity of Phox-I1 to $p67^{phox}$. (A) Using microscale thermophoresis, $p67^{phox}$ recombinant protein (1-200) was able to bind Phox-I1 with an Kd of ~100 nM. (B) Similar to A, the ability of Phox-I1 to bind a recombinant mutant of $p67^{phox}$ at the site critical for Rac1-GTP binding, p67R38Q, was tested by microscale thermophoresis. (C) Experiment described in B was repeated with a random $p67^{phox}$ mutation, R188A. (D) Constitutively active Rac1V12 mutant protein binds $p67^{phox}$ with an Kd of ~40 nM using microscale thermophoresis. (E) Rac1 wild type protein (predominantly in GDP-bound state) cannot bind $p67^{phox}$ using microscale thermophoresis. (F) Competitive binding of $p67^{phox}$ with Phox-I1 or vehicle control, followed by titration of RacV12 protein using above methods. (G) Phox-I1 is unable to bind RacV12 recombinant protein via above technique.

It is to be understood that both the foregoing general description and the following detailed description are exemplary and explanatory only and are not restrictive of the embodiments claimed. In this application, the use of the singular includes the plural unless specifically stated otherwise. In this application, the use of "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

In certain embodiments a compound is provided having the structure of Formula I:

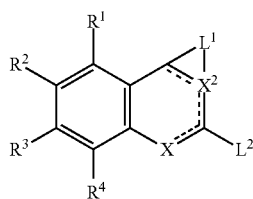

I or a pharmaceutically acceptable salt thereof, wherein:

$L^1$ is selected from the group consisting of $C_{3-6}$ alkyl, $C_{3-6}$ alkenyl, $C_{2-5}$ alkoxy, $C_{1-5}$ heteroalkyl, —$CH_2$—$C(R^{10})$ =N—, $C_{5-6}$ cycloalkyl, $C_{5-6}$ cycloalkenyl, and arylalkyl, each optionally substituted with one or more $R^{1A}$;

$L^2$ is

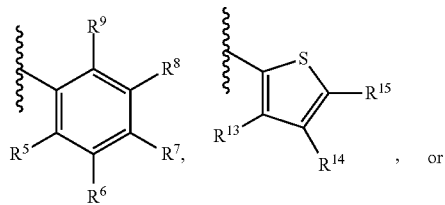

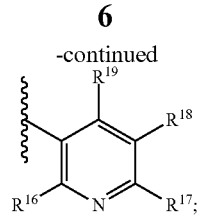

$R^{10}$ is hydrogen or $R^{1A}$;

$R^{1A}$ is hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, ($R^{1BB}R^{1CC}$N)alkyl, ($C_1$-$C_6$)alkyl optionally substituted with up to 5 fluoro, and ($C_1$-$C_6$)alkoxy optionally substituted with up to 5 fluoro, said aryl, heteroaryl, heterocyclyl, arylalkyl, heteroarylalkyl, heterocyclylalkyl, cycloalkyl, cycloalkenyl, and (cycloalkyl)alkyl in the definition of $R^{1A}$ are each optionally substituted with one or more $R^{1AA}$;

each $R^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, ($C_1$-$C_6$)alkyl optionally substituted with up to 5 fluoro, and ($C_1$-$C_6$)alkoxy optionally substituted with up to 5 fluoro;

$R^1$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^D$, —NHC(=O)R$^{1D}$, —OC(=O)R$^{1D}$, —C(=O)R$^{1D}$, —C(=O)OR$^{1D}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$) alkoxy optionally substituted with up to 5 fluoro;

$R^2$ is selected from the group consisting of fluoro, bromo, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —S(O)$_z$R$^{1D}$, —OC(=O)R$^{1D}$, hydroxy($C_2$-$C_6$)alkyl, aryl, heteroaryl, heterocyclyl, arylalkyl, (cycloalkyl)alkyl, ($C_3$-$C_7$)cycloalkyl, ($C_4$-$C_6$)alkyl optionally substituted with up to 5 fluoro, and ($C_2$-$C_6$)alkoxy optionally substituted with up to 5 fluoro;

$R^3$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)R$^{1D}$, —NHC(=O)R$^{1D}$, —OC(=O)R$^{1D}$, —C(=O)R$^{1D}$, —C(=O)OR$^{1D}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$) alkoxy optionally substituted with up to 5 fluoro;

$R^4$ is selected from the group consisting of hydrogen, hydroxy, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)R$^{1D}$, —NHC(=O)R$^{1D}$, —OC(=O)R$^{1D}$, —C(=O)R$^{1D}$, —C(=O)OR$^{1D}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$) alkoxy optionally substituted with up to 5 fluoro;

each NR$^{1B}$R$^{1C}$ is independently selected, wherein R$^{1B}$ and R$^{1C}$ are each independently from the group consisting of hydrogen, $C_{1-6}$alkyl, aryl, arylalkyl, cycloalkyl, (cyclolalkyl)alkyl, $(R^{1BB}R^{1CC}N)$alkyl, and $(R^{1BB}R^{1CC}N)C(=O)-$;

$R^{1D}$ is independently selected from the group consisting of hydroxy, aryl, heteroaryl, heterocyclyl, arylalkyl, cycloalkyl, cycloalkenyl, (cyclolalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro;

each $R^{1BB}R^{1CC}N$ is independently selected, wherein $R^{1BB}$ and $R^{1CC}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

$R^5$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1-C_6$)alkyl, aryl, heteroaryl, heterocyclyl, arylalkyl, (cyclolalkyl)alkyl, $(C_3-C_7)$cycloalkyl, $(C_1-C_6)$alkyl optionally substituted with up to 5 fluoro, and $(C_3-C_6)$alkoxy optionally substituted with up to 5 fluoro;

$R^6$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1-C_6$)alkyl, aryl, heteroaryl, heterocyclyl, arylalkyl, (cyclolalkyl)alkyl, $(C_3-C_7)$cycloalkyl, $(C_2-C_6)$alkyl optionally substituted with up to 5 fluoro, and $(C_1-C_6)$alkoxy optionally substituted with up to 5 fluoro;

$R^7$ is selected from the group consisting of hydrogen, fluoro, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —NHS(O)$_z$R$^{1G}$, —NHC(=O)R$^{1G}$, —OC(=O)R$^{1G}$, hydroxy($C_1-C_6$)alkyl, aryl, heteroaryl, heterocyclyl, arylalkyl, (cyclolalkyl)alkyl, $(C_3-C_7)$cycloalkyl, $(C_1-C_6)$alkyl optionally substituted with up to 5 fluoro, and $(C_3-C_6)$alkoxy optionally substituted with up to 5 fluoro;

$R^8$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1-C_6$)alkyl, aryl, heteroaryl, heterocyclyl, arylalkyl, (cyclolalkyl)alkyl, $(C_2-C_6)$alkyl optionally substituted with up to 5 fluoro, and $(C_1-C_6)$alkoxy optionally substituted with up to 5 fluoro;

$R^9$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1-C_6$)alkyl, aryl, heteroaryl, heterocyclyl, arylalkyl, (cyclolalkyl)alkyl, $(C_3-C_7)$cycloalkyl, $(C_1-C_6)$alkyl optionally substituted with up to 5 fluoro, and $(C_3-C_6)$alkoxy optionally substituted with up to 5 fluoro, wherein one or more of $R^5$, $R^6$, $R^7$, $R^8$, and $R^9$ is not hydrogen or methyl;

each $NR^{1E}R^{1F}$ is independently selected, wherein $R^{1E}$ and $R^{1F}$ are each independently from the group consisting of hydrogen, $C_{1-6}$alkyl, aryl, arylalkyl, cycloalkyl, (cyclolalkyl)alkyl, $(R^{1EE}R^{1FF}N)$alkyl, and $(R^{1EE}R^{1FF}N)C(=O)-$;

$R^{1G}$ is independently selected from the group consisting of hydroxy, aryl, heteroaryl, heterocyclyl, arylalkyl, cycloalkyl, cycloalkenyl, (cyclolalkyl)alkyl, $(R^{1EE}R^{1FF}N)$alkyl, $(C_1-C_6)$alkyl optionally substituted with up to 5 fluoro, and $(C_1-C_6)$alkoxy optionally substituted with up to 5 fluoro;

each $R^{1EE}R^{1FF}N$ is independently selected, wherein $R^{1EE}$ and $R^{1FF}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

X is O (oxygen), S (sulfur), N (nitrogen) or $NR^{11}$;

each z is independently 0, 1 or 2;

$R^{11}$ is H (hydrogen) or $C_{1-6}$ alkyl;

$X^2$ is C (carbon), $CR^{12}$, or N (nitrogen);

$R^{12}$ is H (hydrogen) or $C_{1-6}$ alkyl;

$R^{13}$ and $R^{14}$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$ hydroxy($C_1-C_6$)alkyl, aryl, heteroaryl, heterocyclyl, arylalkyl, (cyclolalkyl)alkyl, $(C_3-C_7)$cycloalkyl, $(C_1-C_6)$alkyl optionally substituted with up to 5 fluoro, and $(C_1-C_6)$alkoxy optionally substituted with up to 5 fluoro;

$R^{15}$ is halo;

$R^{16}$, $R^{17}$, $R^{18}$, and $R^{19}$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1-C_6$)alkyl, aryl, heteroaryl, heterocyclyl, arylalkyl, (cyclolalkyl)alkyl, $(C_3-C_7)$cycloalkyl, $(C_1-C_6)$alkyl optionally substituted with up to 5 fluoro, and $(C_1-C_6)$alkoxy optionally substituted with up to 5 fluoro wherein one or more of $R^{16}$, $R^{17}$, $R^{18}$, and $R^{19}$ is not hydrogen; and each dashed line is an optional double bond.

In certain embodiments a compound is provided having the structure of Formula I:

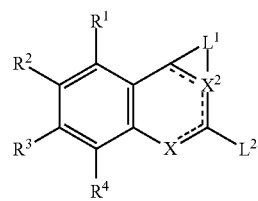

I a pharmaceutically acceptable salt thereof, wherein:

$L^1$ is selected from the group consisting of $C_{3-6}$ alkyl, $C_{3-6}$ alkenyl, $C_{2-5}$ alkoxy, $C_{1-5}$ heteroalkyl, —CH$_2$—C(R$^{10}$)

=N—, C$_{5-6}$ cycloalkyl, C$_{5-6}$ cycloalkenyl, and arylalkyl, each optionally substituted with one or more R$^{1A}$;

L$^2$ is

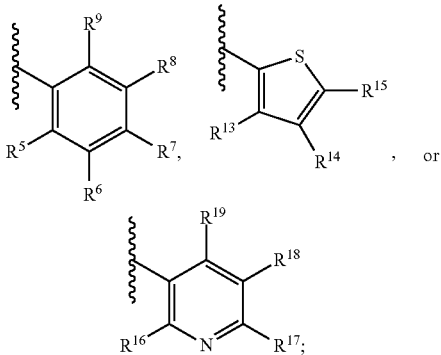

, or

R$^{10}$ is hydrogen or R$^{1A}$;

R$^{1A}$ is hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, (R$^{1BB}$R$^{1CC}$N)alkyl, (C$_1$-C$_6$)alkyl optionally substituted with up to 5 fluoro, and (C$_1$-C$_6$)alkoxy optionally substituted with up to 5 fluoro, said aryl, heteroaryl, heterocyclyl, arylalkyl, heteroarylalkyl, heterocyclylalkyl, cycloalkyl, cycloalkenyl, and (cyclolalkyl)alkyl in the definition of R$^{1A}$ are each optionally substituted with one or more R$^{1AA}$;

each R$^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, (C$_1$-C$_6$)alkyl optionally substituted with up to 5 fluoro, and (C$_1$-C$_6$)alkoxy optionally substituted with up to 5 fluoro;

R$^1$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

R$^2$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

R$^3$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

R$^4$ is selected from the group consisting of hydrogen, hydroxy, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

each NR$^{1B}$R$^{1C}$ is independently selected, wherein R$^{1B}$ and R$^{1C}$ are each independently from the group consisting of hydrogen, C$_{1-6}$alkyl, aryl, arylalkyl, cycloalkyl, (cyclolalkyl)alkyl, (R$^{1BB}$R$^{1CC}$N)alkyl, and (R$^{1BB}$R$^{1CC}$N)C(=O)—;

R$^{1D}$ is independently selected from the group consisting of hydroxy, aryl, heteroaryl, heterocyclyl, arylalkyl, cycloalkyl, cycloalkenyl, (cyclolalkyl)alkyl, (R$^{1BB}$R$^{1CC}$N)alkyl, (C$_1$-C$_6$)alkyl optionally substituted with up to 5 fluoro, and (C$_1$-C$_6$)alkoxy optionally substituted with up to 5 fluoro;

each R$^{1BB}$R$^{1CC}$N is independently selected, wherein R$^{1BB}$ and R$^{1CC}$ are each independently from the group consisting of hydrogen, C$_{1-6}$alkylOC(=O)—, C$_{1-6}$alkyl, C$_{1-6}$alkylC(=O)—, aryl, arylalkyl, cycloalkyl, and heterocyclyl;

R$^5$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_3$-C$_6$)alkyl optionally substituted with up to 5 fluoro, and (C$_2$-C$_6$)alkoxy optionally substituted with up to 5 fluoro;

R$^6$ is selected from the group consisting of hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_2$-C$_6$)alkyl, and (C$_2$-C$_6$)alkoxy optionally substituted with up to 5 fluoro;

R$^7$ is selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

R$^8$ is selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1$-$C_6$)alkyl, aryl, heteroaryl, heterocyclyl, arylalkyl, (cyclolalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^9$ is selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1$-$C_6$)alkyl, aryl, heteroaryl, heterocyclyl, arylalkyl, (cyclolalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

each NR$^{1E}$R$^{1F}$ is independently selected, wherein R$^{1E}$ and R$^{1F}$ are each independently from the group consisting of hydrogen, $C_{1-6}$alkyl, aryl, arylalkyl, cycloalkyl, (cyclolalkyl)alkyl, (R$^{1EE}$R$^{1FF}$N)alkyl, and (R$^{1EE}$R$^{1FF}$N)C(=O)—;

R$^{1G}$ is independently selected from the group consisting of hydroxy, aryl, heteroaryl, heterocyclyl, arylalkyl, cycloalkyl, cycloalkenyl, (cyclolalkyl)alkyl, (R$^{1EE}$R$^{1FF}$N)alkyl, ($C_1$-$C_6$)alkyl optionally substituted with up to 5 fluoro, and ($C_1$-$C_6$)alkoxy optionally substituted with up to 5 fluoro;

each R$^{1EE}$R$^{1FF}$N is independently selected, wherein R$^{1EE}$ and R$^{1FF}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

X is O (oxygen), S (sulfur), N (nitrogen) or NR$^{11}$;

each z is independently 0, 1 or 2;

R$^{11}$ is H (hydrogen) or $C_{1-6}$ alkyl;

$X^2$ is C (carbon), CR$^{12}$, or N (nitrogen);

R$^{12}$ is H (hydrogen) or $C_{1-6}$ alkyl;

R$^{13}$, and R$^{14}$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1$-$C_6$)alkyl, aryl, heteroaryl, heterocyclyl, arylalkyl, (cyclolalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

R$^{15}$ is halo;

R$^{16}$, R$^{17}$, R$^{18}$, and R$^{19}$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy($C_1$-$C_6$)alkyl, aryl, heteroaryl, heterocyclyl, arylalkyl, (cyclolalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro wherein one or more of R$^{16}$, R$^{17}$, R$^{18}$, and R$^{19}$ is not hydrogen; and each dashed line is an optional double bond.

In certain embodiments a pharmaceutical composition is provided comprising a pharmaceutically acceptable excipient, and a compound having the structure of Formula I:

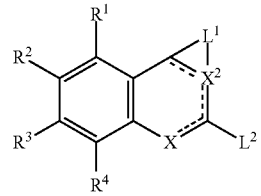

or a pharmaceutically acceptable salt thereof, wherein:

$L^1$ is selected from the group consisting of $C_{3-6}$ alkyl, $C_{3-6}$ alkenyl, $C_{2-5}$ alkoxy, $C_{1-5}$ heteroalkyl, —CH$_2$—C(R$^{10}$)=N—, $C_{5-6}$ cycloalkyl, $C_{5-6}$ cycloalkenyl, and arylalkyl, each optionally substituted with one or more R$^{14}$;

$L^2$ is

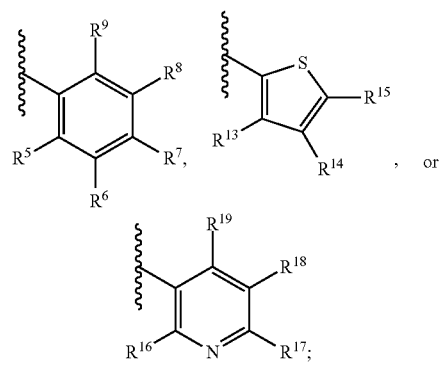

R$^{10}$ is hydrogen or R$^{14}$;

each R$^{14}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, (R$^{1BB}$R$^{1CC}$N)alkyl, ($C_1$-$C_6$)alkyl optionally substituted with up to 5 fluoro, and ($C_1$-$C_6$)alkoxy optionally substituted with up to 5 fluoro, said aryl, heteroaryl, heterocyclyl, arylalkyl, heteroarylalkyl, heterocyclylalkyl, cycloalkyl, cycloalkenyl, and (cyclolalkyl)alkyl in the definition of R$^{14}$ are each optionally substituted with one or more R$^{14A}$;

each R$^{14A}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, ($C_1$-$C_6$)alkyl optionally substituted with up to 5 fluoro, and ($C_1$-$C_6$)alkoxy optionally substituted with up to 5 fluoro;

R$^1$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy($C_1$-$C_6$)alkyl, aryl, heteroaryl, heterocyclyl, arylalkyl, (cyclolalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

R$^2$ is selected from the group consisting of hydrogen, fluoro, bromo, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)

$NR^{1B}R^{1C}$, $-S(O)_zR^{1D}$, $-OC(=O)R^{1D}$, hydroxy($C_2$-$C_6$)alkyl, aryl, heteroaryl, heterocyclyl, arylalkyl, (cycloalkyl)alkyl, ($C_3$-$C_7$)cycloalkyl, ($C_4$-$C_6$)alkyl optionally substituted with up to 5 fluoro, and ($C_2$-$C_6$) alkoxy optionally substituted with up to 5 fluoro;

$R^3$ is selected from the group consisting of hydrogen, hydroxy, halo, cyano, nitro, $-S(O)_zNR^{1B}R^{1C}$, $-NHS(O)_zNR^{1B}R^{1C}$, $-OC(=O)NR^{1B}R^{1C}$, $-NHC(=O)NR^{1B}R^{1C}$, $-C(=O)NR^{1B}R^{1C}$, $-NR^{1B}R^{1C}$, $-S(O)_zR^{1D}$, $-NHS(O)_zR^{1D}$, $-NHC(=O)R^{1D}$, $-OC(=O)R^{1D}$, $-C(=O)R^{1D}$, $-C(=O)OR^{1D}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^4$ is selected from the group consisting of hydrogen, hydroxy, halo, cyano, nitro, $-S(O)_zNR^{1B}R^{1C}$, $-NHS(O)_zNR^{1B}R^{1C}$, $-OC(=O)NR^{1B}R^{1C}$, $-NHC(=O)NR^{1B}R^{1C}$, $-C(=O)NR^{1B}R^{1C}$, $-NR^{1B}R^{1C}$, $-S(O)_zR^{1D}$, $-NHS(O)_zR^{1D}$, $-NHC(=O)R^{1D}$, $-OC(=O)R^{1D}$, $-C(=O)R^{2D}$, $-C(=O)OR^{2D}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro, wherein $R^2$ or $R^4$ is not hydrogen;

each $NR^{1B}R^{1C}$ is independently selected, wherein $R^{1B}$ and $R^{1C}$ are each independently from the group consisting of hydrogen, $C_{1-6}$alkyl, aryl, arylalkyl, cycloalkyl, (cyclolalkyl)alkyl, $(R^{1BB}R^{1CC}N)$alkyl, and $(R^{1BB}R^{1CC}N)C(=O)-$;

each $R^{1D}$ is independently selected from the group consisting of hydroxy, aryl, heteroaryl, heterocyclyl, arylalkyl, cycloalkyl, cycloalkenyl, (cyclolalkyl)alkyl, $(R^{1BB}R^{1CC}N)$alkyl, ($C_1$-$C_6$)alkyl optionally substituted with up to 5 fluoro, and ($C_1$-$C_6$)alkoxy optionally substituted with up to 5 fluoro;

each $R^{2D}$ is independently selected from the group consisting of hydroxy, aryl, heteroaryl, heterocyclyl, arylalkyl, cycloalkyl, cycloalkenyl, (cyclolalkyl)alkyl, $(R^{1BB}R^{1CC}N)$alkyl, ($C_1$-$C_6$)alkyl substituted with up to 5 fluoro, and ($C_1$-$C_6$)alkoxy substituted with up to 5 fluoro;

each $R^{1BB}R^{1CC}N$ is independently selected, wherein $R^{1BB}$ and $R^{1CC}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

$R^5$ is selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^6$ is selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^7$ is selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^8$ is selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

$R^9$ is selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro;

each $NR^{1E}R^{1F}$ is independently selected, wherein $R^{1E}$ and $R^{1F}$ are each independently from the group consisting of hydrogen, $C_{1-6}$alkyl, aryl, arylalkyl, cycloalkyl, (cyclolalkyl)alkyl, $(R^{1EE}R^{1FF}N)$alkyl, and $(R^{1EE}R^{1FF}N)C(=O)-$;

$R^{1G}$ is independently selected from the group consisting of hydroxy, aryl, heteroaryl, heterocyclyl, arylalkyl, cycloalkyl, cycloalkenyl, (cyclolalkyl)alkyl, $(R^{1EE}R^{1FF}N)$alkyl, ($C_1$-$C_6$)alkyl optionally substituted with up to 5 fluoro, and ($C_1$-$C_6$)alkoxy optionally substituted with up to 5 fluoro;

each $R^{1EE}R^{1FF}N$ is independently selected, wherein $R^{1EE}$ and $R^{1FF}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

X is O (oxygen), S (sulfur), N (nitrogen) or $NR^{11}$;

each z is independently 0, 1 or 2;

$R^{11}$ is H (hydrogen) or $C_{1-6}$ alkyl;

$X^2$ is C (carbon), $CR^{12}$, or N (nitrogen);

$R^{12}$ is H (hydrogen) or $C_{1-6}$ alkyl;

$R^{13}$, $R^{14}$, $R^{15}$, $R^{16}$, $R^{17}$, $R^{18}$, and $R^{19}$ are each independently selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1$-$C_6$)alkyl, aryl, heteroaryl, heterocyclyl, arylalkyl, (cycloalkyl)alkyl, ($C_3$-$C_7$)cycloalkyl, ($C_1$-$C_6$)alkyl optionally substituted with up to 5 fluoro, and ($C_1$-$C_6$)alkoxy optionally substituted with up to 5 fluoro; and each dashed line is an optional double bond.

In certain embodiments a pharmaceutical composition is provided comprising a pharmaceutically acceptable excipient, and a compound having the structure of Formula I:

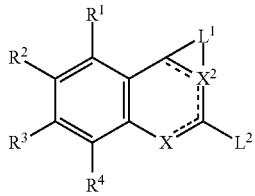

I or a pharmaceutically acceptable salt thereof,
wherein:
$L^1$ is selected from the group consisting of $C_{3-6}$ alkyl, $C_{3-6}$ alkenyl, $C_{2-5}$ alkoxy, $C_{1-5}$ heteroalkyl, —$CH_2$—$C(R^{10})$=N—, $C_{5-6}$ cycloalkyl, $C_{5-6}$ cycloalkenyl, and arylalkyl, each optionally substituted with one or more $R^{14}$;
$L^2$ is

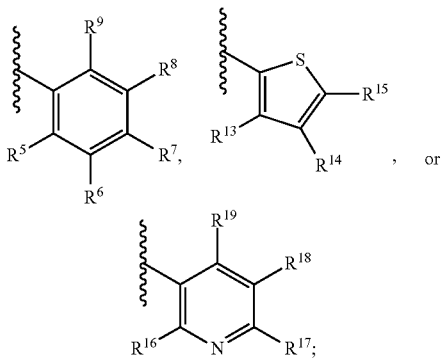

$R^{10}$ is hydrogen or $R^{14}$;
$R^{14}$ is hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro,
said aryl, heteroaryl, heterocyclyl, arylalkyl, heteroarylalkyl, heterocyclylalkyl, cycloalkyl, cycloalkenyl, and (cycloalkyl)alkyl in the definition of $R^{14}$ are each optionally substituted with one or more $R^{1AA}$;
each $R^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, $(C_1-C_6)$alkyl optionally substituted with up to 5 fluoro, and $(C_1-C_6)$alkoxy optionally substituted with up to 5 fluoro;
$R^1$ is selected from the group consisting of hydrogen, hydroxy, halo, cyano, nitro, —$S(O)_zNR^{1B}R^{1C}$, —NHS$(O)_zNR^{1B}R^{1C}$, —OC(=O)$NR^{1B}R^{1C}$, —NHC(=O)$NR^{1B}R^{1C}$, —C(=O)$NR^{1B}R^{1C}$, —$NR^{1B}R^{1C}$, —$S(O)_zR^{1D}$, —NHS(O)$R^{1D}$, —NHC(=O)$R^{1D}$, —OC(=O)$R^{1D}$, —C(=O)$R^{1D}$, —C(=O)O$R^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$ alkoxy optionally substituted with up to 5 fluoro;

$R^2$ is selected from the group consisting of hydrogen, hydroxy, halo, cyano, nitro, —$S(O)_zNR^{1B}R^{1C}$, —NHS$(O)_zNR^{1B}R^{1C}$, —OC(=O)$NR^{1B}R^{1C}$, —NHC(=O)$NR^{1B}R^{1C}$, —C(=O)$NR^{1B}R^{1C}$, —$NR^{1B}R^{1C}$, —$S(O)_zR^{1D}$, —NHS(O)$R^{1D}$, —NHC(=O)$R^1$, —OC(=O)$R^{1D}$, —C(=O)$R^{1D}$, —C(=O)O$R^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$ alkoxy optionally substituted with up to 5 fluoro;
$R^3$ is selected from the group consisting of hydrogen, hydroxy, halo, cyano, nitro, —$S(O)_zNR^{1B}R^{1C}$, —NHS$(O)_zNR^{1B}R^{1C}$, —OC(=O)$NR^{1B}R^{1C}$, —NHC(=O)$NR^{1B}R^{1C}$, —C(=O)$NR^{1B}R^{1C}$, —$NR^{1B}R^{1C}$, —$S(O)_zR^{1D}$, —NHS(O)$R^{1D}$, —NHC(=O)$R^{1D}$, —OC(=O)$R^{1D}$, —C(=O)$R^{1D}$, —C(=O)O$R^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$ alkoxy optionally substituted with up to 5 fluoro;
$R^4$ is selected from the group consisting of hydrogen, hydroxy, halo, cyano, nitro, —$S(O)_zNR^{1B}R^{1C}$, —NHS$(O)_zNR^{1B}R^{1C}$, —OC(=O)$NR^{1B}R^{1C}$, —NHC(=O)$NR^{1B}R^{1C}$, —C(=O)$NR^{1B}R^{1C}$, —$NR^{1B}R^{1C}$, —$S(O)_zR^{1D}$, —NHS(O)$R^{1D}$, —NHC(=O)$R^{1D}$, —OC(=O)$R^{1D}$, —C(=O)$R^{1D}$, —C(=O)O$R^{1D}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$ alkoxy optionally substituted with up to 5 fluoro;
each $NR^{1B}R^{1C}$ is independently selected, wherein $R^{1B}$ and $R^{1C}$ are each independently from the group consisting of hydrogen, $C_{1-6}$alkyl, aryl, arylalkyl, cycloalkyl, (cyclolalkyl)alkyl, $(R^{1BB}R^{1CC}N)$alkyl, and $(R^{1BB}R^{1CC}N)C(=O)$—;
$R^{1D}$ is independently selected from the group consisting of hydroxy, aryl, heteroaryl, heterocyclyl, arylalkyl, cycloalkyl, cycloalkenyl, (cycloalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro;
each $R^{1BB}R^{1CC}N$ is independently selected, wherein $R^{1BB}$ and $R^{1CC}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;
$R^5$ is selected from the group consisting of hydrogen, hydroxy, fluoro, cyano, —$S(O)_zNR^{1E}R^{1F}$, —NHS(O)$_zNR^{1E}R^{1F}$, —OC(=O)$NR^{1E}R^{1F}$, —NHC(=O)$NR^{1E}R^{1F}$, —C(=O)$NR^{1E}R^{1F}$, —$NR^{1E}R^{1F}$, —$S(O)_zR^{1G}$, —NHS(O)$_zR^{1G}$, —NHC(=O)$R^{1G}$, —OC(=O)$R^{1G}$, —C(=O)$R^{1G}$, —C(=O)O$R^{1G}$, hydroxy$(C_1-C_6)$alkyl, aryl, heteroaryl, heterocyclyl, arylalkyl, (cycloalkyl)alkyl, $(C_3-C_7)$cycloalkyl, $(C_3-C_6)$alkyl optionally substituted with up to 5 fluoro, and $(C_2-C_6)$alkoxy optionally substituted with up to 5 fluoro;
$R^6$ is selected from the group consisting of hydrogen, hydroxy, fluoro, cyano, —$S(O)_zNR^{1E}R^{1F}$, —NHS(O)$_zNR^{1E}R^{1F}$, —OC(=O)$NR^{1E}R^{1F}$, —NHC(=O)$NR^{1E}R^{1F}$, —C(=O)$NR^{1E}R^{1F}$, —$NR^{1E}R^{1F}$, —$S(O)_zR^{1G}$, —NHS(O)$_zR^{1G}$, —NHC(=O)$R^{1G}$, —OC(=O)$R^{1G}$, —C(=O)$R^{1G}$, —C(=O)O$R^{1G}$, hydroxy$(C_1-C_6)$alkyl, aryl, heteroaryl, heterocyclyl, arylalkyl, (cycloalkyl)alkyl, $(C_3-C_7)$cycloalkyl, $(C_1-C_6)$alkyl, and $(C_1-C_6)$alkoxy optionally substituted with up to 5 fluoro;

$R^7$ is selected from the group consisting of hydrogen, hydroxy, fluoro, cyano, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, heteroaryl, heterocyclyl, arylalkyl, (cyclolalkyl)alkyl, (C$_3$-C$_7$)cycloalkyl, (C$_3$-C$_6$)alkyl optionally substituted with up to 5 fluoro, and (C$_1$-C$_6$)alkoxy, wherein at least one of R$^5$, R$^6$ or R$^7$ is not hydrogen;

$R^8$ is selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

$R^9$ is selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

each NR$^{1E}$R$^{1F}$ is independently selected, wherein R$^{1E}$ and R$^{1F}$ are each independently from the group consisting of hydrogen, C$_{1-6}$alkyl, aryl, arylalkyl, cycloalkyl, (cyclolalkyl)alkyl, (R$^{1EE}$R$^{1FF}$N)alkyl, and (R$^{1EE}$R$^{1FF}$N)C(=O)—;

$R^{1G}$ is independently selected from the group consisting of hydroxy, aryl, heteroaryl, heterocyclyl, arylalkyl, cycloalkyl, cycloalkenyl, (cyclolalkyl)alkyl, (R$^{1EE}$R$^{1FF}$N)alkyl, (C$_1$-C$_6$)alkyl optionally substituted with up to 5 fluoro, and (C$_1$-C$_6$)alkoxy optionally substituted with up to 5 fluoro;

each R$^{1EE}$R$^{1FF}$N is independently selected, wherein R$^{1EE}$ and R$^{1FF}$ are each independently from the group consisting of hydrogen, C$_{1-6}$alkylOC(=O)—, C$_{1-6}$alkyl, C$_{1-6}$alkylC(=O)—, aryl, arylalkyl, cycloalkyl, and heterocyclyl;

X is O (oxygen), S (sulfur), N (nitrogen) or NR$^{11}$;
each z is independently 0, 1 or 2;
R$^{11}$ is H (hydrogen) or C$_{1-6}$ alkyl;
X$^2$ is C (carbon), CR$^{12}$, or N (nitrogen);
R$^{12}$ is H (hydrogen) or C$_{1-6}$ alkyl;
R$^{13}$, R$^{14}$, R$^{15}$, R$^{16}$, R$^{17}$, R$^{18}$, and R$^{19}$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro; and
each dashed line is an optional double bond.

In certain embodiments a method of inhibiting p67$^{phox}$ protein is provided, the method comprising contacting p67$^{phox}$ protein with a compound having the structure of Formula I:

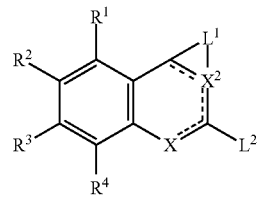

I or a pharmaceutically acceptable salt thereof,
wherein:
L$^1$ is selected from the group consisting of C$_{3-6}$ alkyl, C$_{3-6}$ alkenyl, C$_{2-5}$ alkoxy, C$_{1-5}$ heteroalkyl, —CH$_2$—C(R$^{10}$)=N—, C$_{5-6}$ cycloalkyl, C$_{5-6}$ cycloalkenyl, and arylalkyl, each optionally substituted with one or more R$^{1A}$;
R$^{10}$ is hydrogen or R$^{1A}$;
L$^2$ is aryl or heteroaryl each optionally substituted with one or more with one or more R$^{2A}$;
each R$^{1A}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, (R$^{1BB}$R$^{1CC}$N)alkyl, (C$_1$-C$_6$)alkyl optionally substituted with up to 5 fluoro, and (C$_1$-C$_6$)alkoxy optionally substituted with up to 5 fluoro,
said aryl, heteroaryl, heterocyclyl, arylalkyl, heteroarylalkyl, heterocyclylalkyl, cycloalkyl, cycloalkenyl, and (cycloalkyl)alkyl in the definition of R$^{1A}$ are each optionally substituted with one or more R$^{1AA}$;
each R$^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cycloalkyl)alkyl, (C$_1$-C$_6$)alkyl optionally substituted with up to 5 fluoro, and (C$_1$-C$_6$)alkoxy optionally substituted with up to 5 fluoro;
each R$^{2A}$ is independently selected from the group consisting of hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;
R$^1$, R$^2$, R$^3$, and R$^4$ are each independently selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;
each NR$^{1B}$R$^{1C}$ is independently selected, wherein R$^{1B}$ and R$^{1C}$ are each independently from the group consisting of hydrogen, $C_{1-6}$alkyl, aryl, arylalkyl, cycloalkyl, (cyclolalkyl)alkyl, $(R^{1BB}R^{1CC}N)$alkyl, and $(R^{1BB}R^{1CC}N)C(=O)-$;

each $R^{1D}$ is independently selected from the group consisting of hydroxy, aryl, heteroaryl, heterocyclyl, arylalkyl, cycloalkyl, cycloalkenyl, (cyclolalkyl)alkyl, $(R^{1BB}R^{1CC}N)$alkyl, $(C_1-C_6)$alkyl optionally substituted with up to 5 fluoro, and $(C_1-C_6)$alkoxy optionally substituted with up to 5 fluoro;

each $R^{1BB}R^{1CC}N$ is independently selected, wherein $R^{1BB}$ and $R^{1CC}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl;

X is O (oxygen), S (sulfur), N (nitrogen) or $NR^{11}$; each z is independently 0, 1 or 2;

$R^{11}$ is H (hydrogen) or $C_{1-6}$ alkyl;

$X^2$ is C (carbon), $CR^{12}$, or N (nitrogen);

$R^{12}$ is H (hydrogen) or $C_{1-6}$ alkyl; and each dashed line is an optional double bond.

Examples of methods provided herein include a method of treating neutrophil infiltration, hemorrhagic shock or lung inflammation in an individual, a method for evaluating the inhibition of p67$^{phox}$ protein by performing in vitro testing and evaluating the results, and a method for evaluating the inhibition of p67$^{phox}$ protein by performing in vivo testing and evaluating the results.

In certain embodiments a compound, composition or method as disclosed herein is provided, wherein the compound having the structure of Formula I has the structure of Formula II,

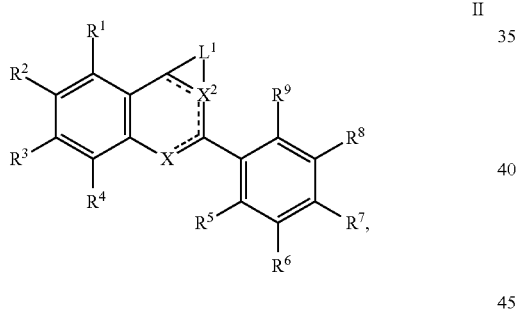

or a pharmaceutically acceptable salt thereof,
wherein:
$R^5$, $R^6$, $R^7$, $R^8$, and $R^9$ are each independently selected from the group consisting of hydrogen, hydroxy, halo, cyano, nitro, $-S(O)_zNR^{1E}R^{1F}$, $-NHS(O)_zNR^{1E}R^{1F}$, $-OC(=O)NR^{1E}R^{1F}$, $-NHC(=O)NR^{1E}R^{1F}$, $-C(=O)NR^{1E}R^{1F}$, $-NR^{1E}R^{1F}$, $-S(O)_zR^{1G}$, $-NHS(O)_zR^{1G}$, $-NHC(=O)R^{1G}$, $-OC(=O)R^{1G}$, $-C(=O)R^{1G}$, $-C(=O)OR^{1G}$, hydroxy($C_1-C_6$)alkyl, aryl, heteroaryl, heterocyclyl, arylalkyl, (cycloalkyl)alkyl, $(C_3-C_7)$cycloalkyl, $(C_1-C_6)$alkyl optionally substituted with up to 5 fluoro, and $(C_1-C_6)$alkoxy optionally substituted with up to 5 fluoro;

each $NR^{1E}R^{1F}$ is independently selected, wherein $R^{1E}$ and $R^{1F}$ are each independently from the group consisting of hydrogen, $C_{1-6}$alkyl, aryl, arylalkyl, cycloalkyl, (cyclolalkyl)alkyl, $(R^{1EE}R^{1FF}N)$alkyl, and $(R^{1EE}R^{1FF}N)C(=O)-$;

each $R^{1G}$ is independently selected from the group consisting of hydroxy, aryl, heteroaryl, heterocyclyl, arylalkyl, cycloalkyl, cycloalkenyl, (cyclolalkyl)alkyl, $(R^{1EE}R^{1FF}N)$alkyl, $(C_1-C_6)$alkyl optionally substituted with up to 5 fluoro, and $(C_1-C_6)$alkoxy optionally substituted with up to 5 fluoro; and each $R^{1EE}R^{1FF}N$ is independently selected, wherein $R^{1EE}$ and $R^{1FF}$ are each independently from the group consisting of hydrogen, $C_{1-6}$alkylOC(=O)—, $C_{1-6}$alkyl, $C_{1-6}$alkylC(=O)—, aryl, arylalkyl, cycloalkyl, and heterocyclyl.

In certain embodiments a compound, composition or method as disclosed herein is provided, wherein the compound having the structure of Formula II has the structure of Formula Ia, Formula Ib, Formula Ic, or Formula Id,

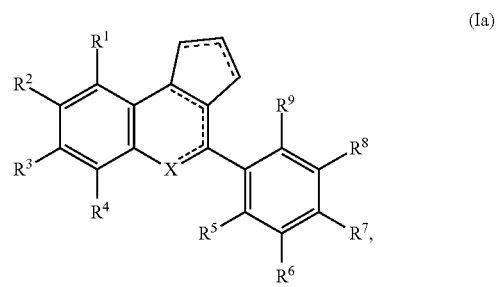

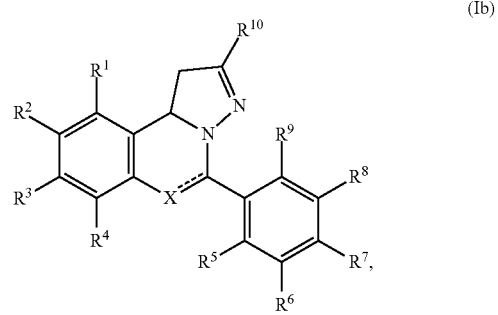

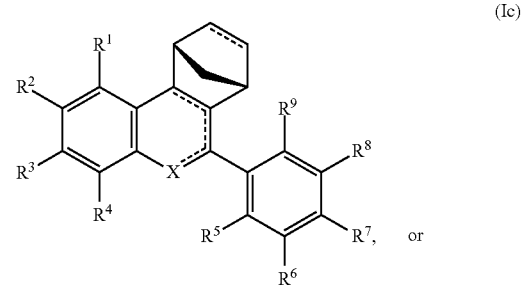

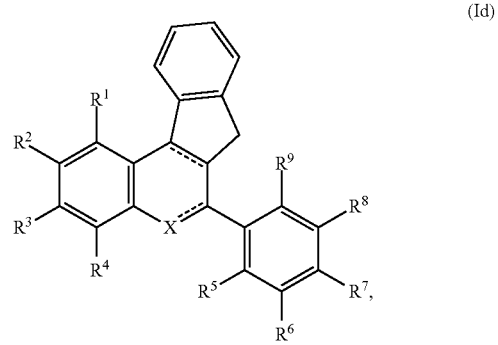

or a pharmaceutically acceptable salt thereof.

In certain embodiments a compound, composition or method as disclosed herein is provided, wherein the compound having the structure of Formula Ia has the structure of Formula Iaa, Iab, or Iac,

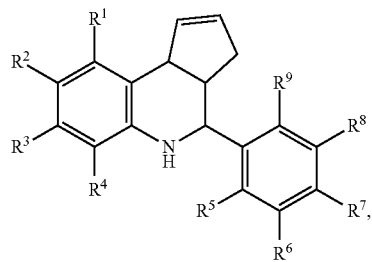

(Iaa)

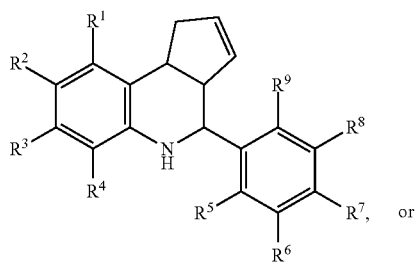

(Iab)

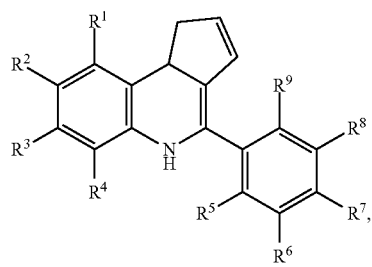

(Iac)

or a pharmaceutically acceptable salt thereof.

In certain embodiments a compound, composition or method as disclosed herein is provided, wherein the compound having the structure of Formula Ib has the structure of Formula Iba,

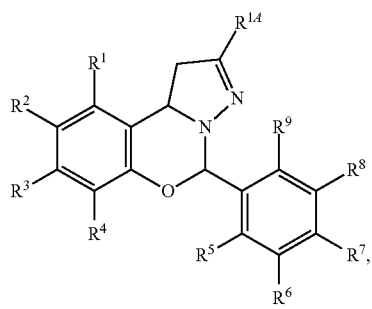

(Iba)

a pharmaceutically acceptable salt thereof, wherein:

$R^{1A}$ is aryl or heteroaryl, said aryl and heteroaryl in the definition of $R^{1A}$ are each optionally substituted with one or more $R^{1AA}$.

In certain embodiments a compound, composition or method as disclosed herein is provided, wherein the compound having the structure of Formula Ic has the structure of Formula Ica or Icb,

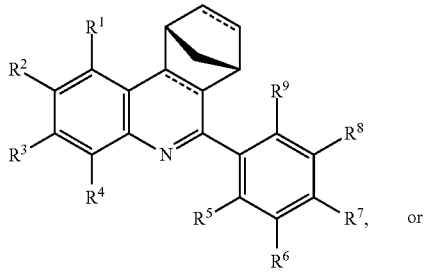

(Ica)

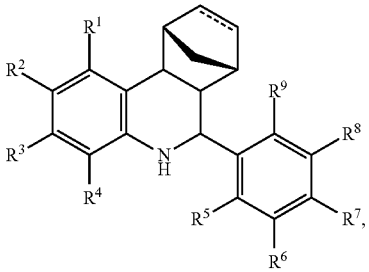

(Icb)

or a pharmaceutically acceptable salt thereof.

In certain embodiments a compound, composition or method as disclosed herein is provided, wherein the compound having the structure of Formula Id has the structure of Formula Ida,

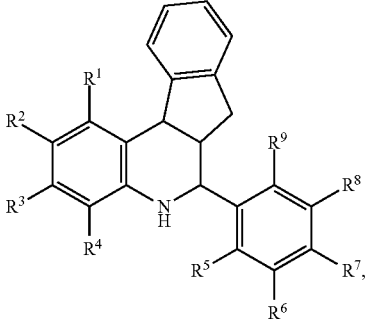

(Ida)

or a pharmaceutically acceptable salt thereof.

In certain embodiments a compound, composition or method as disclosed herein is provided, wherein:

$R^1$, $R^2$, $R^3$, and $R^4$ are each independently selected from the group consisting of hydrogen, hydroxy, halo, cyano, nitro, —S(O)$_z$NR$^{1B}$R$^{1C}$, —C(=O)NR$^{1B}$R$^{1C}$, —NR$^{1B}$R$^{1C}$, —NHS(O)$_z$R$^{1D}$, —NHC(=O)R$^{1D}$, —C(=O)R$^{1D}$, —C(=O)OR$^{1D}$, hydroxy(C$_1$-C$_6$)alkyl, (C$_1$-C$_6$)alkyl optionally substituted with up to 5 fluoro, and (C$_1$-C$_6$)alkoxy optionally substituted with up to 5 fluoro;

each NR$^{1B}$R$^{1C}$ is independently selected, wherein R$^{1B}$ and R$^{1C}$ are each independently from the group consisting of hydrogen, and C$_{1-6}$alkyl; and each R$^{1D}$ is independently selected from the group consisting of (C$_1$-C$_6$)alkyl optionally substituted with up to 5 fluoro, and (C$_1$-C$_6$)alkoxy optionally substituted with up to 5 fluoro.

In certain embodiments a compound, composition or method as disclosed herein is provided,
wherein:
$R^5$, $R^6$, $R^7$, $R^8$, and $R^9$ are each independently selected from the group consisting of hydrogen, halo, nitro, —$NR^{1E}R^{1F}$, ($C_1$-$C_6$)alkyl optionally substituted with up to 5 fluoro, and ($C_1$-$C_6$)alkoxy optionally substituted with up to 5 fluoro; and
each $NR^{1E}R^{1F}$ is independently selected, wherein $R^{1E}$ and $R^{1F}$ are each independently from the group consisting of hydrogen, and $C_{1-6}$alkyl.

In certain embodiments a compound, composition or method as disclosed herein is provided,
wherein:
$L^1$ is selected from the group consisting of —$CH_2$—C($R^1$)=N—, propyl, propenyl, ethoxy, cyclopentyl, cyclopentenyl, and benzyl, each optionally substituted with one or more $R^{1A}$;
each $R^{1A}$ is independently selected from the group consisting of aryl, and heteroaryl,
  said aryl and heteroaryl in the definition of $R^{1A}$ are each optionally substituted with one or more $R^{1AA}$;
each $R^{1AA}$ is independently selected from the group consisting of halo and ($C_1$-$C_6$)alkoxy optionally substituted with up to 5 fluoro;
X is O (oxygen), N (nitrogen) or $NR^{11}$;
$R^{11}$ is H (hydrogen); and
$X^2$ is C (carbon), —CH—, or N (nitrogen).

In certain embodiments a compound, composition or method as disclosed herein is provided,
wherein:
$L^1$ is selected from the group consisting of —$CH_2$—C($R^{10}$)=N—, propyl, propenyl, ethoxy, cyclopentyl, cyclopentenyl, and benzyl, each optionally substituted with one or more $R^{1A}$;
each $R^{1A}$ is independently selected from the group consisting of aryl, and heteroaryl,
  said aryl and heteroaryl in the definition of $R^{1A}$ are each optionally substituted with one or more $R^{1AA}$;
each $R^{1AA}$ is independently selected from the group consisting of halo and ($C_1$-$C_6$)alkoxy optionally substituted with up to 5 fluoro;
$R^1$, $R^2$, $R^3$, and $R^4$ are each independently selected from the group consisting of hydrogen, hydroxy, halo, cyano, nitro, —$S(O)_zNR^{1B}R^{1C}$, —$C(=O)NR^{1B}R^{1C}$, —$NR^{1B}R^{1C}$, —$NHS(O)_zR^{1D}$, —$NHC(=O)R^{1D}$, —$C(=O)R^{1D}$, —$C(=O)OR^{1D}$, hydroxy($C_1$-$C_6$)alkyl, ($C_1$-$C_6$)alkyl optionally substituted with up to 5 fluoro, and ($C_1$-$C_6$)alkoxy optionally substituted with up to 5 fluoro;
each $NR^{1B}R^{1C}$ is independently selected, wherein $R^{1B}$ and $R^{1C}$ are each independently from the group consisting of hydrogen, and $C_{1-6}$alkyl;
each $R^{1D}$ is independently selected from the group consisting of ($C_1$-$C_6$)alkyl optionally substituted with up to 5 fluoro, and ($C_1$-$C_6$)alkoxy optionally substituted with up to 5 fluoro;
$R^5$, $R^6$, $R^7$, $R^8$, and $R^9$ are each independently selected from the group consisting of hydrogen, halo, nitro, —$NR^{1E}R^{1F}$, ($C_1$-$C_6$)alkyl optionally substituted with up to 5 fluoro, and ($C_1$-$C_6$)alkoxy optionally substituted with up to 5 fluoro;
each $NR^{1E}R^{1F}$ is independently selected, wherein $R^{1E}$ and $R^{1F}$ are each independently from the group consisting of hydrogen, and $C_{1-6}$alkyl;

X is O (oxygen), N (nitrogen) or $NR^{11}$;
$R^{11}$ is H (hydrogen); and
$X^2$ is C (carbon), —CH—, or N (nitrogen).

In certain embodiments a compound, composition or method as disclosed herein is provided, wherein the compound having the structure of Formula I has the structure of Formula III,

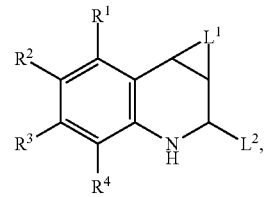

or a pharmaceutically acceptable salt thereof.

In certain embodiments a compound, composition or method as disclosed herein is provided, wherein the compound having the structure of Formula III has the structure of Formula IIIa or Formula IIIb,

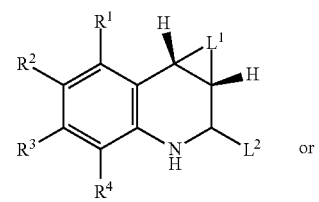

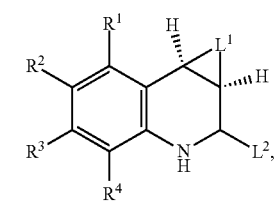

or a pharmaceutically acceptable salt thereof.

In certain embodiments a compound, composition or method as disclosed herein is provided,
wherein:
$R^1$ is hydrogen;
$R^2$ is selected from the group consisting of hydrogen, fluoro, bromo, —$S(O)_zNR^{1B}R^{1C}$, and ($C_2$-$C_6$)alkoxy optionally substituted with up to 5 fluoro;
$R^3$ is hydrogen;
$R^4$ is selected from the group consisting of hydrogen, nitro, —$C(=O)R^{2D}$, and ($C_1$-$C_6$)alkoxy optionally substituted with up to 5 fluoro, wherein $R^2$ or $R^4$ is not hydrogen;
each $NR^{1B}R^{1C}$ is independently selected, wherein $R^{1B}$ and $R^{1C}$ are each independently from the group consisting of hydrogen, and $C_{1-6}$alkyl; and $R^{2D}$ is hydroxy.

In certain embodiments a compound, composition or method as disclosed herein is provided,
wherein:
$L^1$ is selected from the group consisting of —$CH_2$—C($R^{10}$)=N—, propyl, propenyl, ethoxy, cyclopentyl, cyclopentenyl, and benzyl, each optionally substituted with one or more $R^{1A}$;
each $R^{1A}$ is independently selected from the group consisting of aryl, and heteroaryl, said aryl and heteroaryl in the definition of $R^{1A}$ are each optionally substituted with one or more $R^{1AA}$;
each $R^{1AA}$ is independently selected from the group consisting of halo and $(C_1-C_6)$alkoxy optionally substituted with up to 5 fluoro;
$R^1$ is hydrogen;
$R^2$ is selected from the group consisting of hydrogen, fluoro, bromo, —S(O)$_z$NR$^{1B}$R$^{1C}$, and $(C_2-C_6)$alkoxy optionally substituted with up to 5 fluoro;
$R^3$ is hydrogen;
$R^4$ is selected from the group consisting of hydrogen, nitro, —C(=O)R$^{2D}$, and $(C_1-C_6)$alkoxy optionally substituted with up to 5 fluoro, wherein $R^2$ or $R^4$ is not hydrogen;
each NR$^{1B}$R$^{1C}$ is independently selected, wherein $R^{1B}$ and $R^{1C}$ are each independently from the group consisting of hydrogen, and $C_{1-6}$alkyl;
$R^{2D}$ is hydroxy;
$R^5$ is selected from the group consisting of hydrogen, hydroxy and halo;
$R^6$ is selected from the group consisting of hydrogen, halo, nitro, and $(C_1-C_6)$alkoxy optionally substituted with up to 5 fluoro;
$R^7$ is selected from the group consisting of hydrogen and nitro;
$R^8$ is hydrogen;
$R^9$ is hydrogen;
X is O (oxygen), N (nitrogen) or NR$^{11}$;
$R^{11}$ is H (hydrogen); and
$X^2$ is C (carbon), —CH—, or N (nitrogen).
In certain embodiments a compound, composition or method as disclosed herein is provided,
wherein:
$L^1$ is selected from the group consisting of —CH$_2$—C(R$^{10}$)=N—, propyl, propenyl, ethoxy, cyclopentyl, cyclopentenyl, and benzyl, each optionally substituted with one or more $R^{1A}$;
each $R^{1A}$ is independently selected from the group consisting of aryl, and heteroaryl,
said aryl and heteroaryl in the definition of $R^{1A}$ are each optionally substituted with one or more $R^{1AA}$;
each $R^{1AA}$ is independently selected from the group consisting of halo and $(C_1-C_6)$alkoxy optionally substituted with up to 5 fluoro;
$R^1$ is hydrogen;
$R^2$ is selected from the group consisting of hydrogen, fluoro, bromo, —S(O)$_z$NR$^{1B}$R$^{1C}$, and $(C_1-C_6)$alkoxy optionally substituted with up to 5 fluoro;
$R^3$ is hydrogen;
$R^4$ is selected from the group consisting of hydrogen, nitro, —C(=O)R$^{1D}$, and $(C_1-C_6)$alkoxy optionally substituted with up to 5 fluoro, wherein $R^2$ or $R^4$ is not hydrogen;
each NR$^{1B}$R$^{1C}$ is independently selected, wherein $R^{1B}$ and $R^{1C}$ are each independently from the group consisting of hydrogen, and $C_{1-6}$alkyl;
$R^{1D}$ is hydroxy;
$R^5$ is selected from the group consisting of hydrogen, hydroxy and fluoro;
$R^6$ is selected from the group consisting of hydrogen, fluoro, and $(C_1-C_6)$alkoxy optionally substituted with up to 5 fluoro, wherein $R^5$ or $R^6$ is not hydrogen;
$R^7$ is hydrogen;
$R^8$ is hydrogen;
$R^9$ is hydrogen;

X is O (oxygen), N (nitrogen) or NR$^{11}$;
$R^{11}$ is H (hydrogen); and
$X^2$ is C (carbon), —CH—, or N (nitrogen).
In certain embodiments a compound, composition or method as disclosed herein is provided,
wherein:
$R^1$ is hydrogen;
$R^2$ is selected from the group consisting of fluoro, bromo, —S(O)$_z$NR$^{1B}$R$^{1C}$, and $(C_2-C_6)$alkoxy optionally substituted with up to 5 fluoro;
$R^3$ is hydrogen;
$R^4$ is selected from the group consisting of hydrogen, nitro, —C(=O)R$^{1D}$, and $(C_1-C_6)$alkoxy optionally substituted with up to 5 fluoro;
each NR$^{1B}$R$^{1C}$ is independently selected, wherein $R^{1B}$ and $R^{1C}$ are each independently from the group consisting of hydrogen, and $C_{1-6}$alkyl; and
$R^{1D}$ is hydroxy.
In certain embodiments a compound, composition or method as disclosed herein is provided,
wherein:
$L^1$ is selected from the group consisting of —CH$_2$—C(R$^{10}$)=N—, propyl, propenyl, ethoxy, cyclopentyl, cyclopentenyl, and benzyl, each optionally substituted with one or more $R^{1A}$;
each $R^{1A}$ is independently selected from the group consisting of aryl, and heteroaryl,
said aryl and heteroaryl in the definition of $R^{1A}$ are each optionally substituted with one or more $R^{1AA}$;
each $R^{1AA}$ is independently selected from the group consisting of halo and $(C_1-C_6)$alkoxy optionally substituted with up to 5 fluoro;
$R^1$ is hydrogen;
$R^2$ is selected from the group consisting of fluoro, bromo, —S(O)$_z$NR$^{1B}$R$^{1C}$, and $(C_2-C_6)$alkoxy optionally substituted with up to 5 fluoro;
$R^3$ is hydrogen;
$R^4$ is selected from the group consisting of hydrogen, nitro, —C(=O)R$^{1D}$, and $(C_1-C_6)$alkoxy optionally substituted with up to 5 fluoro;
each NR$^{1B}$R$^{1C}$ is independently selected, wherein $R^{1B}$ and $R^{1C}$ are each independently from the group consisting of hydrogen, and $C_{1-6}$alkyl;
$R^{1D}$ is hydroxy;
$R^5$ is selected from the group consisting of hydrogen, hydroxy and fluoro;
$R^6$ is selected from the group consisting of hydrogen, fluoro, and $(C_1-C_6)$alkoxy optionally substituted with up to 5 fluoro;
$R^7$ is selected from the group consisting of hydrogen and nitro;
$R^8$ is hydrogen;
$R^9$ is hydrogen, wherein one or more of $R^5$, $R^6$, or $R^7$ is not hydrogen or methyl;
X is O (oxygen), N (nitrogen) or NR$^{11}$;
$R^{11}$ is H (hydrogen); and
$X^2$ is C (carbon), —CH—, or N (nitrogen).
In certain embodiments a compound, composition or method as disclosed herein is provided,
wherein:
$R^1$ is hydrogen;
$R^2$ is selected from the group consisting of hydrogen, fluoro, bromo, —S(O)$_z$NR$^{1B}$R$^{1C}$, and $(C_1-C_6)$alkoxy optionally substituted with up to 5 fluoro;
$R^3$ is hydrogen;
$R^4$ is selected from the group consisting of hydrogen, nitro, —C(=O)R$^{1D}$, and $(C_1-C_6)$alkoxy optionally substituted with up to 5 fluoro, wherein $R^2$ or $R^4$ is not hydrogen;

$R^{1B}$ and $R^{1C}$ are each independently from the group consisting of hydrogen, and $C_{1-6}$alkyl; and $R^{1D}$ is hydroxy.

In certain embodiments a compound, composition or method as disclosed herein is provided, wherein:

$L^1$ is selected from the group consisting of —CH$_2$—C($R^{10}$)=N—, propyl, propenyl, ethoxy, cyclopentyl, cyclopentenyl, and benzyl, each optionally substituted with one or more $R^{14}$;

each $R^{14}$ is independently selected from the group consisting of aryl, and heteroaryl,
  said aryl and heteroaryl in the definition of $R^{14}$ are each optionally substituted with one or more $R^{14A}$;

each $R^{14A}$ is independently selected from the group consisting of halo and $(C_1-C_6)$alkoxy optionally substituted with up to 5 fluoro;

$R^1$ is hydrogen;

$R^2$ is selected from the group consisting of hydrogen, fluoro, bromo, —S(O)$_z$NR$^{1B}$R$^{1C}$, and $(C_1-C_6)$alkoxy optionally substituted with up to 5 fluoro;

$R^3$ is hydrogen;

$R^4$ is selected from the group consisting of hydrogen, nitro, —C(=O)R$^{1D}$, and $(C_1-C_6)$alkoxy optionally substituted with up to 5 fluoro, wherein $R^2$ or $R^4$ is not hydrogen;

$R^{1B}$ and $R^{1C}$ are each independently from the group consisting of hydrogen, and $C_{1-6}$alkyl;

$R^{1D}$ is hydroxy;

$R^5$ is selected from the group consisting of hydrogen, hydroxy and fluoro;

$R^6$ is selected from the group consisting of fluoro, and $(C_2-C_6)$alkoxy optionally substituted with up to 5 fluoro;

$R^7$ is hydrogen;

$R^8$ is hydrogen;

$R^9$ is hydrogen;

X is O (oxygen), N (nitrogen) or NR$^{11}$;

$R^{11}$ is H (hydrogen); and $X^2$ is C (carbon), —CH—, or N (nitrogen).

In certain embodiments a compound, composition or method as disclosed herein is provided including a compound having the structure:

29
-continued
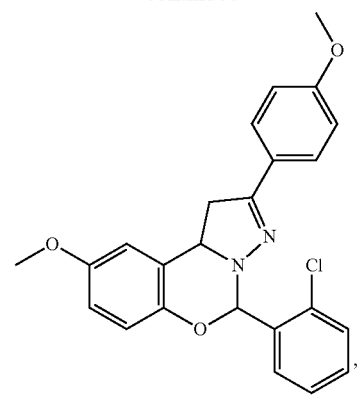
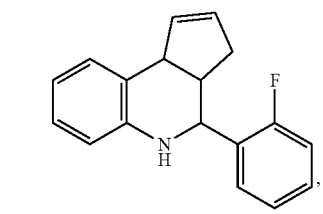
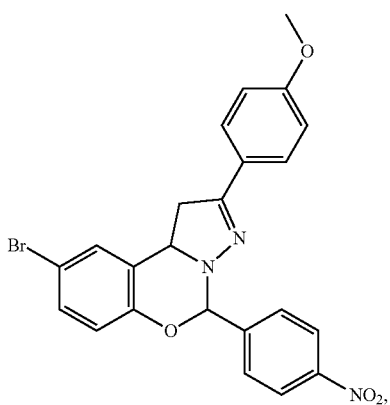
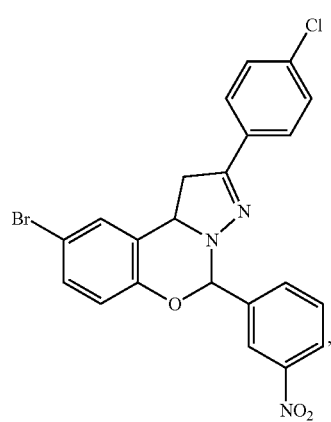
30
-continued
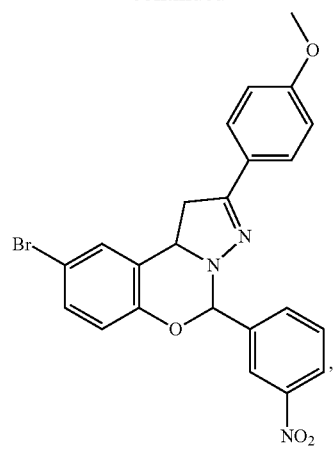
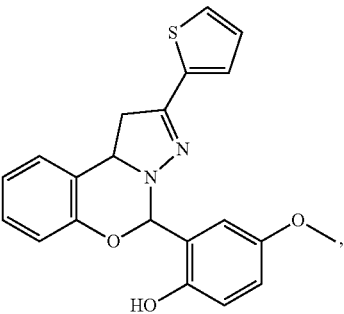
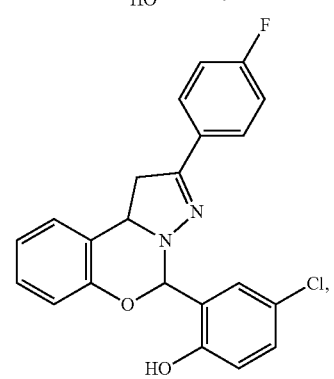
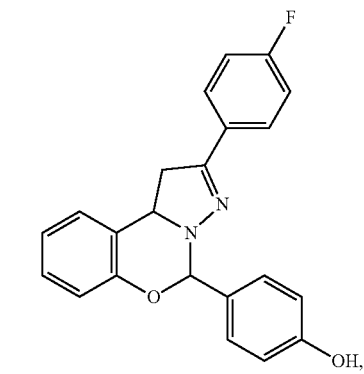
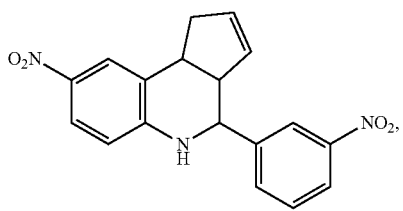

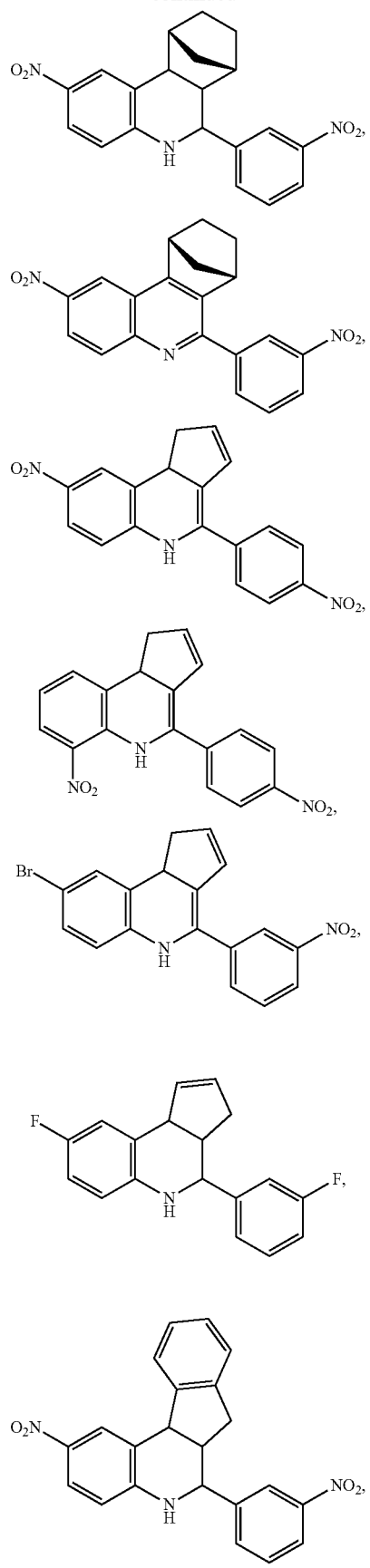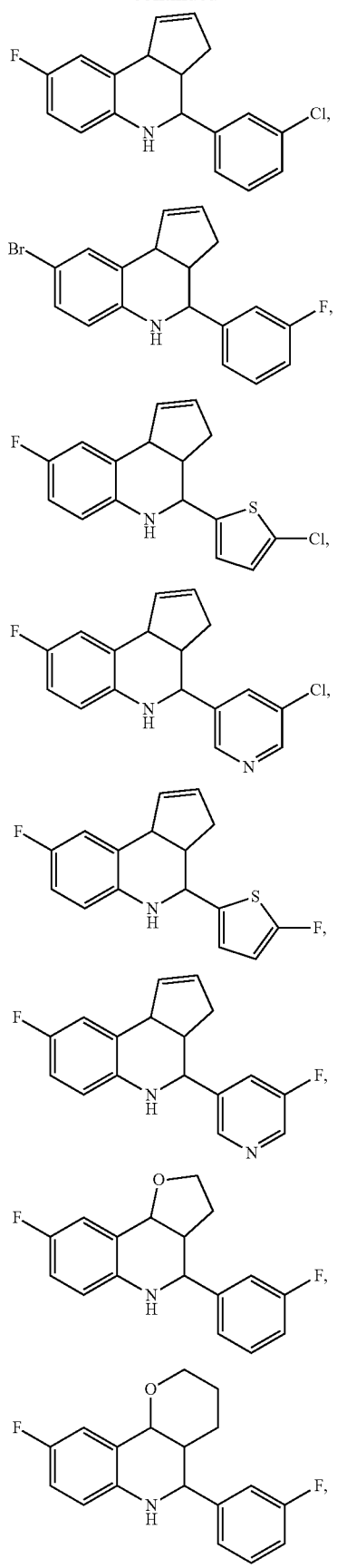

-continued

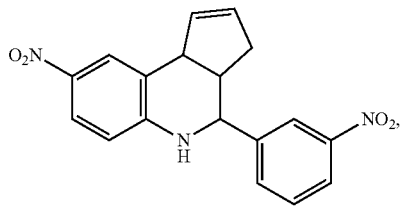

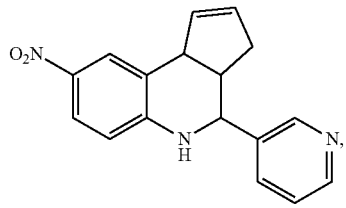

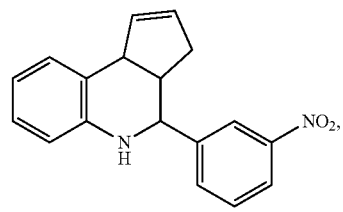

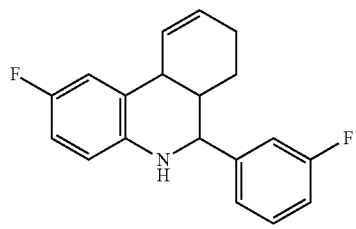

or a pharmaceutically acceptable salt thereof.

In certain embodiments a compound, composition or method as disclosed herein is provided including a compound having the structure:

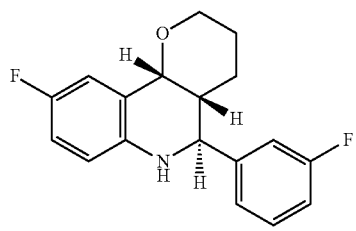

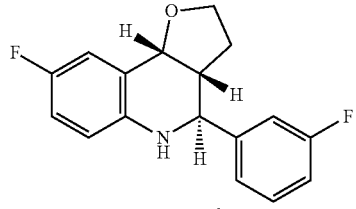

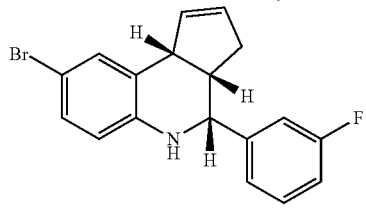

-continued

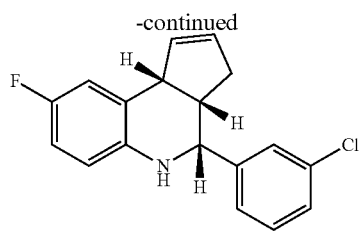

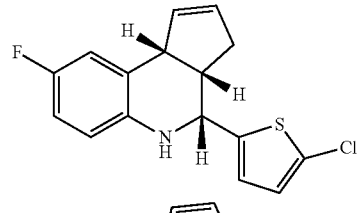

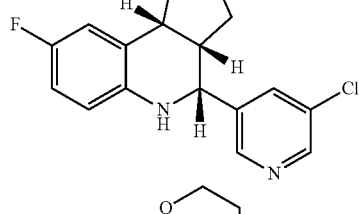

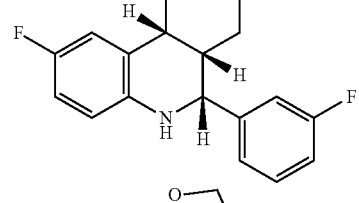

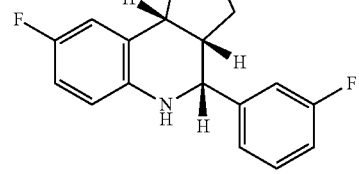

or a pharmaceutically acceptable salt thereof.

In certain embodiments a compound, composition or method as disclosed herein is provided wherein the compound is not:

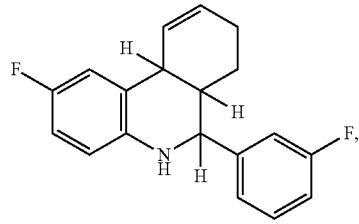 [SMILES: Fc1cccc(C2Nc3ccc(F)cc3C3C=CCCC32)c1]

or a pharmaceutically acceptable salt thereof.

In certain embodiments a compound, composition or method as disclosed herein is provided wherein L is $C_3$ alkenyl.

DEFINITIONS

Unless specific definitions are provided, the nomenclatures utilized in connection with, and the laboratory procedures and techniques of, analytical chemistry, synthetic organic chemistry, and medicinal and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, and delivery, and treatment of patients.

As used herein, the following terms are defined with the following meanings, unless expressly stated otherwise.

The term "alkyl" refers to a branched or unbranched fully saturated acyclic aliphatic hydrocarbon group. An alkyl may be branched or straight chain. Alkyls may be substituted or unsubstituted. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "alkenyl" used herein refers to a straight or branched chain aliphatic hydrocarbon of from two to twenty carbon atoms containing at least one carbon-carbon double bond including, but not limited to, 1-propenyl, 2-propenyl, 2-methyl-1-propenyl, 1-butenyl, 2-butenyl, and the like. In certain embodiments, an alkenyl comprises 2 to 20 carbon atoms (whenever it appears herein, a numerical range such as "2 to 20" refers to each integer in the given range; e.g., "2 to 20 carbon atoms" means that an alkenyl group may comprise only 2 carbon atoms, 3 carbon atoms, etc., up to and including 20 carbon atoms, although the term "alkenyl" also includes instances where no numerical range of carbon atoms is designated). An alkenyl may be designated as "$C_2$-$C_6$ alkenyl" or similar designations. By way of example only, "$C_2$-$C_4$ alkenyl" indicates an alkenyl having two, three, or four carbon atoms, e.g., the alkenyl is selected from ethenyl, propenyl, and butenyl.

The term "cycloalkyl" used herein refers to saturated aliphatic ring system having three to twenty carbon atoms. A cycloalkyl refers to monocyclic and polycyclic saturated aliphatic ring system including, but not limited to, cyclopropyl, cyclopentyl, cyclohexyl, cycloheptyl, bicyclo[4.4.0]decanyl, bicyclo[2.2.1]heptanyl, adamantyl, norbornyl, and the like. In certain embodiments, a cycloalkyl comprises 3 to 20 carbon atoms (whenever it appears herein, a numerical range such as "3 to 20" refers to each integer in the given range; e.g., "3 to 20 carbon atoms" means that a cycloalkyl group may comprise only 3 carbon atoms, etc., up to and including 20 carbon atoms, although the term "cycloalkyl" also includes instances where no numerical range of carbon atoms is designated). A cycloalkyl may be designated as "$C_3$-$C_7$ cycloalkyl" or similar designations. By way of example only, "$C_3$-$C_6$ cycloalkyl" indicates a cycloalkyl having two, three, four, five or six carbon atoms, e.g., the cycloalkyl is selected from cyclopropyl, cyclobutyl, cyclopentyl, and cyclohexyl.

The term "cycloalkenyl" used herein refers to aliphatic ring system having three to twenty carbon atoms having at least one carbon-carbon double bond in the ring. A cycloalkenyl refers to monocyclic and polycyclic unsaturated aliphatic ring system including, but are not limited to, cyclopropenyl, cyclopentenyl, cyclohexenyl, cycloheptenyl, bicyclo[3.1.0]hexyl, norbornylenyl, 1,1'-bicyclopentenyl, and the like. In certain embodiments, a cycloalkenyl comprises 3 to 20 carbon atoms (whenever it appears herein, a numerical range such as "3 to 20" refers to each integer in the given range; e.g., "3 to 20 carbon atoms" means that a cycloalkenyl group may comprise only 3 carbon atoms, etc., up to and including 20 carbon atoms, although the term "cycloalkenyl" also includes instances where no numerical range of carbon atoms is designated). A cycloalkenyl may be designated as "$C_3$-$C_7$ cycloalkenyl" or similar designations. By way of example only, "$C_3$-$C_6$ cycloalkenyl" indicates an alkenyl having two, three, four, five or six carbon atoms, e.g., the cycloalkyl is selected from cyclopropenyl, cyclobutenyl, cyclopentenyl, and cyclohexenyl.

The term "alkoxy" used herein refers to straight or branched chain alkyl covalently bonded to oxygen where the "alkoxy" is attached to the parent molecule through at least an oxygen linkage. Where an "alkoxy" substituent requires two points of attachment to the rest of the molecule the "alkoxy" is attached to the parent molecule through an oxygen linkage and a carbon linkage. Examples of alkoxy groups include, but are not limited to, methoxy, ethoxy, propoxy, isopropoxy, butoxy, n-butoxy, sec-butoxy, t-butoxy and the like. An alkoxy may be designated as "$C_1$-$C_6$ alkoxy" or similar designations. By way of example only, "$C_1$-$C_4$ alkoxy" indicates an alkyl having one, two, three, or four carbon atoms, e.g., the alkoxy is selected from methoxy, ethoxy, propoxy, iso-propoxy, butoxy, iso-butoxy, sec-butoxy, and tert-butoxy.

The term "heteroalkyl" refers to a group comprising at least one alkyl or alkenyl, and one or two heteroatoms. Where a "heteroalkyl" substituent requires two points of attachment to the rest of the molecule the "heteroalkyl" is attached to the parent molecule through a heteroatom linkage and a carbon linkage, a first carbon linkage and a second carbon linkage, or a first heteroatom linkage and a second heteroatom linkage. Examples of heteroalkyls include, but are not limited to, —CH$_2$OCH$_2$CH$_2$—, —CH$_2$OCH$_2$—, —CH$_2$CH$_2$OCH$_2$CH$_2$—, —CH$_2$OCH═CH—, —CH═CHOCH═CH—, —OCH$_2$O—, —CH$_2$NHCH$_2$CH$_2$—, —CH$_2$NHCH$_2$—, —CH$_2$CH$_2$NHCH$_2$CH$_2$—, —NHCH═CH—, —NHCH$_2$CH$_2$—, —N═CHCH$_2$—, —CH$_2$NHCH═CH—, —CH═CHNHCH═CH—, —NHCH$_2$NH—, and the like.

The term "heterocyclic" or "heterocyclyl" used herein refers to a cyclic ring system radical having at least one non-aromatic ring in which one or more ring atoms are not carbon, namely heteroatom. Monocyclic "heterocyclic" or "heterocyclyl" moieties are non-aromatic. Bicyclic "heterocyclic" or "heterocyclyl" moieties include one non-aromatic ring wherein at least one heteroatom is present in a ring. Tricyclic "heterocyclic" or "heterocyclyl" moieties include at least one non-aromatic ring wherein at least one heteroatom is present in a ring. Examples of heterocyclic groups include, but are not limited to, piperidinyl, piperazinyl, morpholinyl, tetrahydrofuranyl, dioxolanyl, tetrahydropyranyl, pyrrolidinyl, and the like.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same as one another, or some or all of the two or more heteroatoms may each be different from the others.

The term "aryl" refers to an aromatic group wherein each of the atoms forming the ring is a carbon atom. Examples of aryl groups include, but are not limited to phenyl, and naphthalenyl. In certain embodiments, a phenyl group is substituted at one or more positions. Examples of aryl groups comprising substitutions include, but are not limited to, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, hydroxynaphthyl, hydroxymethylphenyl, (trifluoromethyl)phenyl, and 4-morpholin-4-ylphenyl.

The term "heteroaryl" refers to an aromatic mono-, bi- or tricyclic ring system wherein at least one atom forming the aromatic ring system is a heteroatom. Heteroaryl rings may be formed by three, four, five, six, seven, eight, nine, or more than nine atoms. Heteroaryl groups may be optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$-alkoxy, $C_{1-6}$-alkyl, $C_{1-6}$-hydroxyalkyl, $C_{1-6}$-aminoalkyl, $C_{1-6}$-alkylamino, alkylsulfenyl, alkylsulfinyl, alkylsulfonyl, sulfamoyl, or trifluoromethyl. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl. Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline.

The term "arylalkyl" refers to a group comprising an aryl group bound to an alkyl group. Examples of arylalkyl groups include, but are not limited to, benzyl, phenethyl, phenpropyl, phenbutyl, and the like. In some embodiments, arylalkyls may be substituted or unsubstituted, and can be substituted on either the aryl or alkyl portion or on both. Where an "arylalkyl" substituent requires two points of attachment to the rest of the molecule the "arylalkyl" can be attached to the parent molecule through a carbon linkage in the aryl group and a carbon linkage in the alkyl group.

The term "heteroarylalkyl" used herein refers to one or more heteroaryl groups appended to an alkyl radical. Examples of heteroarylalkyl include, but are not limited to, pyridylmethyl, furanylmethyl, thiopheneylethyl, and the like. In some embodiments, heteroarylalkyls may be substituted or unsubstituted, and can be substituted on either the heteroaryl or alkyl portion or on both. Where an "heteroarylalkyl" substituent requires two points of attachment to the rest of the molecule the "heteroarylalkyl" can be attached to the parent molecule through a carbon linkage in the heteroaryl group and a carbon linkage in the alkyl group.

The term "heterocyclylalkyl" used herein refers to one or more heterocyclyl groups appended to an alkyl radical. Examples of heterocyclylalkyl include, but are not limited to, piperidinylmethyl, piperidinylethyl, morpholinylmethyl, morpholinylethyl, and the like.

The term "(cycloalkyl)alkyl" used herein refers to one or more cycloalkyl groups appended to an alkyl radical. Examples of (cycloalkyl)alkyl include, but are not limited to, cyclohexylmethyl, cyclohexylethyl, cyclopentylmethyl, cyclopentylethyl, and the like. In some embodiments, (cycloalkyl)alkyl may be substituted or unsubstituted.

Unless otherwise indicated, the term "optionally substituted," refers to a group in which none, one, or more than one of the hydrogen atoms has been replaced with one or more group(s) individually and independently selected from: alkyl, alkenyl, cycloalkenyl, cycloalkyl, aryl, arylalkyl, heteroaryl, heterocyclyl, hydroxy, alkoxy, cyano, halo, oxo, thiocarbonyl, ester, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, and amino, including mono- and di-substituted amino groups, and the protected derivatives of amino groups. Such protective derivatives (and protecting groups that may form such protective derivatives) are known to those of skill in the art and may be found in references such as Greene and Wuts, above. When the group contains a nitrogen, or a sulfur, an oxo as a substituent also includes oxides, for example pyridine-N-oxide, thiopyran sulfoxide and thiopyran-S,S-dioxide. In embodiments in which two or more hydrogen atoms have been substituted, the substituent groups may together form a ring.

The substituent "R" appearing by itself and without a number designation refers to a substituent selected from alkyl, cycloalkyl, aryl, heteroaryl (bonded through a ring carbon) and heterocyclyl (bonded through a ring carbon).

The term "O-carboxy" refers to the group consisting of formula RC(=O)O—.

The term "C-carboxy" refers to the group consisting of formula —C(=O)OR.

The term "cyano" refers to the group consisting of formula —CN.

The term "isocyanato" refers to the group consisting of formula —N=C=O.

The term "thiocyanato" refers to the group consisting of formula —CNS.

The term "isothiocyanato" refers to the group consisting of formula —N=C=S.

The term "sulfonyl" refers to the group consisting of formula —S(=O)—R.

The term "S-sulfonamido" refers to the group consisting of formula —S(=O)$_2$NR.

The term "N-sulfonamido" refers to the group consisting of formula RS(=O)$_2$NH—.

The term "O-carbamyl" refers to the group consisting of formula —OC(=O)—NR.

The term "N-carbamyl" refers to the group consisting of formula ROC(=O)NH—.

The term "O-thiocarbamyl" refers to the group consisting of formula —OC(=S)—NR.

The term "N-thiocarbamyl" refers to the group consisting of formula ROC(=S)NH—.

The term "C-amido" refers to the group consisting of formula —C(=O)—NR$_2$.

The term "N-amido" refers to the group consisting of formula RC(=O)NH—.

The term "oxo" refers to the group consisting of formula =O.

The term "ester" refers to a chemical moiety with formula —(R)$_n$—C(=O)OR', where R and R' are independently selected from alkyl, cycloalkyl, aryl, heteroaryl (bonded through a ring carbon) and non-aromatic heterocycle (bonded through a ring carbon), where n is 0 or 1.

The term "amino" refers to a chemical moiety with formula —NHR'R", where R' and R" are each independently selected from hydrogen, alkyl, cycloalkyl, aryl, heteroaryl (bonded through a ring carbon) and heteroalicyclic (bonded through a ring carbon).

The term "stereoisomers" as used herein means isomers that possess identical constitution, but which differ in the arrangement of their atoms in space. Including, for example, all enantiomers, diastereomers, geometric isomers, and atropisomers.

Wherever a substituent as depicted as a di-radical (i.e., has two points of attachment to the rest of the molecule), it is to be understood that the substituent can be attached in any directional configuration unless otherwise indicated. Thus, for example, a substituent depicted as -AE- or

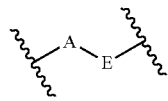

includes the substituent being oriented such that the A is attached at the leftmost attachment point of the molecule as well as attached at the rightmost attachment point of the molecule.

It is to be understood that certain radical naming conventions can include either a mono-radical or a di-radical, depending on the context. For example, where a substituent requires two points of attachment to the rest of the molecule, it is understood that the substituent is a di-radical. A substituent identified as alkyl, that requires two points of attachment, includes di-radicals such as —CH$_2$—, —CH$_2$CH$_2$—, —CH$_2$CH(CH$_3$)CH$_2$—, and the like; a substituent depicted as alkoxy that requires two points of attachment, includes di-radicals such as —OCH$_2$—, —OCH$_2$CH$_2$—, —OCH$_2$CH(CH$_3$)CH$_2$—, and the like: and a substituent identified as arylalkyl that requires two points of attachment, includes di-radicals such as,

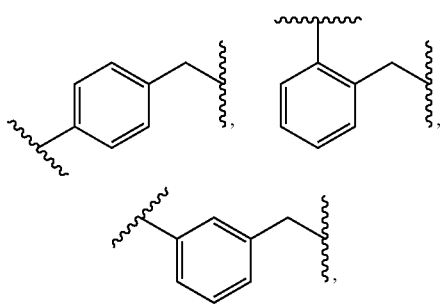

and the like.

Throughout the specification, groups and substituents thereof can be chosen by one skilled in the field to provide stable moieties and compounds.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "therapeutically effective amount" refers to an amount of a pharmaceutical agent sufficient to achieve a desired therapeutic effect.

The term "pharmaceutically acceptable" refers to a formulation of a compound that does not significantly abrogate the biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially purified fraction is a composition wherein the object species comprises at least about 50 percent (on a molar basis) of all species present. In certain embodiments, a substantially pure composition will comprise more than about 80%, 85%, 90%, 95%, or 99% of all species present in the composition. In certain embodiments, the object species is purified to essential homogeneity (contaminant species cannot be detected in the composition by conventional detection methods) wherein the composition consists essentially of a single species.

Certain Compounds

Certain compounds that modulate p67$^{phox}$ protein and/or bind to p67$^{phox}$ protein play a role in health. In certain embodiments, compounds are useful for treating diseases or conditions as provided elsewhere herein.

One of skill in the art will recognize that analogous synthesis schemes may be used to synthesize similar compounds. One of skill will recognize that compounds of the present embodiments may be synthesized using other synthesis schemes. In certain embodiments, a salt corresponding to any of the compounds provided herein is provided.

In certain embodiments, a salt corresponding to a compound as disclosed and described herein is provided. In certain embodiments, a salt is obtained by reacting a compound with an acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as choline, dicyclohexylamine, N-methyl-D-glucamine, tris(hydroxymethyl)methylamine, 4-(2-hydroxyethyl)-morpholine, 1-(2-hydroxyethyl)-pyrrolidine, ethanolamine and salts with amino acids such as arginine, lysine, and the like. In certain embodiments, a salt is obtained by reacting a free acid form of a compound as disclosed and described herein with multiple molar equivalents of a base, such as bis-sodium, bis-ethanolamine, and the like.

In certain embodiments, a salt corresponding to a compound of the present embodiments is selected from acetate, ammonium, benzenesulfonate, benzoate, bicarbonate, bisulfate, bitartrate, borate, bromide, calcium edetate, camsylate, carbonate, chloride, cholinate, clavulanate, citrate, dihydrochloride, diphosphate, edetate, edisylate, estolate, esylate, fumarate, gluceptate, gluconate, glutamate, glycollylarsanilate, hexylresorcinate, hydrabanine, hydrobromide, hydrochloride, hydroxynaphthoate, iodide, isethionate, lactate, lactobionate, laurate, magnesium, malate, maleate, mandelate, mucate, napsylate, nitrate, N-methylglucamine, oxalate, pamoate (embonate), palmitate, pantothenate, phosphate, polygalacturonate, potassium, salicylate, sodium, stearate, subaceatate, succinate, sulfate, tannate, tartrate, teoclate, tosylate, triethiodide, tromethamine, trimethylammonium, and valerate salts.

Certain Assays

Also provided herein are methods of screening compounds for $p67^{phox}$ protein inhibition. These methods can include methods of evaluating inhibitory properties of the compounds provided herein. In certain embodiments, the methods can comprise contacting $p67^{phox}$ protein with a compound provided herein, and evaluating the level of $p67^{phox}$ protein inhibition.

In certain embodiments, the methods can comprise a cell-free assay as described herein or otherwise known in the art. For example, in certain embodiments, the method comprises microscale thermophoresis as described herein or otherwise known in the art. In certain embodiments, the method comprises a cell-free superoxide production assay as described herein or otherwise known in the art.

In certain embodiments, the methods can comprise an in vitro assay on whole cells as described herein or otherwise known in the art. For example, in certain embodiments, the method comprises flow cytometry to measure ROS inhibition as described herein or otherwise known in the art. In certain embodiments, the method comprises nitroblue tetrazolium (NBT) assay to measure ROS production as described herein or otherwise known in the art. In certain embodiments, the method comprises a xanthin/xanthine oxidase assay as described herein or otherwise known in the art. In certain embodiments, the method comprises a chemiluminscense assay as described herein or otherwise known in the art.

In certain embodiments, the methods can comprise an in vivo assay as described herein or otherwise known in the art. For example, in certain embodiments, the method comprises treating an animal with a compound provided herein, and evaluating the effects of treating the animal with the compound. In certain embodiments, the method comprises using an animal model for hemorrhagic shock, such as acute lung injury as described herein or otherwise known in the art. In certain embodiments, the method comprises using an animal model for neutrophil infiltration, hemorrhagic shock, inflammatory bowel disease, or lung inflammation.

The methods provided herein can be performed in vitro or in vivo as will be understood in the art. Examples of in vitro and in vivo methods are provided herein. The results of the methods of evaluating the inhibitory properties of the compounds provided herein can be reported in terms understood in the art including, for example, $IC_{50}$, $EC_{50}$, $K_i$, or other standard terms known in the art. Thus, the evaluation methods provided herein can include evaluating the results where evaluating the results includes determining the inhibitory properties of the compound(s) being tested. In some embodiments evaluating the results also includes comparing the inhibitory properties of a compound being tested to the inhibitory properties of one or more reference compounds. Such a reference compound can be, for example, compound 100, Phox-I2, or Phox-I2 or other compound described herein.

Certain Pharmaceutical Agents

In certain embodiments, at least one compound as disclosed and described herein, or pharmaceutically acceptable salt, ester, amide, and/or prodrug thereof, either alone or combined with one or more pharmaceutically acceptable carriers, forms a pharmaceutical agent. Techniques for formulation and administration of compounds of the present embodiments may be found for example, in "Remington's Pharmaceutical Sciences," Mack Publishing Co., Easton, Pa., 18th edition, 1990, which is incorporated herein by reference in its entirety.

In certain embodiments, a pharmaceutical agent comprising one or more compounds of the present embodiments is prepared using known techniques, including, but not limited to mixing, dissolving, granulating, dragee-making, levigating, emulsifying, encapsulating, entrapping or tabletting processes.

In certain embodiments, a pharmaceutical agent comprising one or more compounds of the present embodiments is a liquid (e.g., a suspension, elixir and/or solution). In certain of such embodiments, a liquid pharmaceutical agent comprising one or more compounds of the present embodiments is prepared using ingredients known in the art, including, but not limited to, water, glycols, oils, alcohols, flavoring agents, preservatives, and coloring agents.

In certain embodiments, a pharmaceutical agent comprising one or more compounds of the present embodiments is a solid (e.g., a powder, tablet, and/or capsule). In certain of such embodiments, a solid pharmaceutical agent comprising one or more compounds of the present embodiments is prepared using ingredients known in the art, including, but not limited to, starches, sugars, diluents, granulating agents, lubricants, binders, and disintegrating agents.

In certain embodiments, a pharmaceutical agent comprising one or more compounds of the present embodiments is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical agent comprising one or more compounds of the present embodiments comprises a delivery system. Examples of delivery systems include, but are not limited to, liposomes and emulsions. Certain delivery systems are useful for preparing certain pharmaceutical agents including those comprising hydrophobic compounds. In certain embodiments, certain organic solvents such as dimethylsulfoxide are used.

In certain embodiments, a pharmaceutical agent comprising one or more compounds of the present embodiments comprises one or more tissue-specific delivery molecules designed to deliver the pharmaceutical agent to specific tissues or cell types. For example, in certain embodiments, pharmaceutical agents include liposomes coated with a tissue-specific antibody.

In certain embodiments, a pharmaceutical agent comprising one or more compounds of the present embodiments comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical agent comprising one or more compounds of the present embodiments comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical agent of the present embodiments may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical agent comprising one or more compounds of the present embodiments comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical agent comprising one or more compounds of the present embodiments is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical agents may be injected directly in the area of desired effect (e.g., in the renal or cardiac area).

In certain embodiments, a pharmaceutical agent comprising one or more compounds of the present embodiments is administered in the form of a dosage unit (e.g., tablet, capsule, bolus, etc.). In certain embodiments, such dosage units comprise a compound as disclosed and described herein in a dose from about 1 µg/kg of body weight to about 50 mg/kg of body weight. In certain embodiments, such dosage units comprise a compound as disclosed and described herein in a dose from about 2 µg/kg of body weight to about 25 mg/kg of body weight. In certain embodiments, such dosage units comprise a compound as disclosed and described herein in a dose from about 10 µg/kg of body weight to about 5 mg/kg of body weight. In certain embodiments, pharmaceutical agents are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical agent.

In certain embodiments, a pharmaceutical agent comprising a compound of the present embodiments is prepared for oral administration. In certain of such embodiments, a pharmaceutical agent is formulated by combining one or more compounds of the present embodiments with one or more pharmaceutically acceptable carriers. Certain of such carriers enable compounds of the present embodiments to be formulated as tablets, pills, dragees, capsules, liquids, gels, syrups, slurries, suspensions and the like, for oral ingestion by a patient. In certain embodiments, pharmaceutical agents for oral use are obtained by mixing one or more compounds of the present embodiments and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical agents are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical agents for oral administration are push-fit capsules made of gelatin. Certain of such push-fit capsules comprise one or more compounds of the present embodiments in admixture with one or more filler such as lactose, binders such as starches, and/or lubricants such as talc or magnesium stearate and, optionally, stabilizers. In certain embodiments, pharmaceutical agents for oral administration are soft, sealed capsules made of gelatin and a plasticizer, such as glycerol or sorbitol. In certain soft capsules, one or more compounds of the present embodiments are be dissolved or suspended in suitable liquids, such as fatty oils, liquid paraffin, or liquid polyethylene glycols. In addition, stabilizers may be added.

In certain embodiments, pharmaceutical agents are prepared for buccal administration. Certain of such pharmaceutical agents are tablets or lozenges formulated in conventional manner.

In certain embodiments, a pharmaceutical agent is prepared for administration by injection (e.g., intravenous, subcutaneous, intramuscular, etc.). In certain of such embodiments, a pharmaceutical agent comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical agents for injection are presented in unit dosage form, e.g., in ampoules or in multi-dose containers. Certain pharmaceutical agents for injection are suspensions, solutions or emulsions in oily or aqueous vehicles, and may contain formulatory agents such as suspending, stabilizing and/or dispersing agents. Certain solvents suitable for use in pharmaceutical agents for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical agent is prepared for transmucosal administration. In certain of such embodiments penetrants appropriate to the barrier to be permeated are used in the formulation. Such penetrants are generally known in the art.

In certain embodiments, a pharmaceutical agent is prepared for administration by inhalation. Certain of such pharmaceutical agents for inhalation are prepared in the form of an aerosol spray in a pressurized pack or a nebulizer. Certain of such pharmaceutical agents comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the present embodiments and a suitable powder base such as lactose or starch.

In certain embodiments, a pharmaceutical agent is prepared for rectal administration, such as a suppositories or retention enema. Certain of such pharmaceutical agents comprise known ingredients, such as cocoa butter and/or other glycerides.

In certain embodiments, a pharmaceutical agent is prepared for topical administration. Certain of such pharmaceutical agents comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present embodiments can be chosen in view of a particular patient's condition. (See e.g., Fingl et al. 1975, in "The Pharmacological Basis of Therapeutics", Ch. 1 p. 1, which is incorporated herein by reference in its entirety). In certain embodiments, a pharmaceutical agent is administered as a single dose. In certain embodiments, a pharmaceutical agent is administered as a series of two or more doses administered over one or more days.

In certain embodiments, a pharmaceutical agent of the present embodiments is administered to a patient between about 0.1% and 500%, 5% and 200%, 10% and 100%, 15% and 85%, 25% and 75%, or 40% and 60% of an established human dosage. Where no human dosage is established, a suitable human dosage may be inferred from $ED_{50}$ or $ID_{50}$ values, or other appropriate values derived from in vitro or in vivo studies.

In certain embodiments, a daily dosage regimen for a patient comprises an oral dose of between 0.1 mg and 2000 mg, 5 mg and 1500 mg, 10 mg and 1000 mg, 20 mg and 500 mg, 30 mg and 200 mg, or 40 mg and 100 mg of a compound of the present embodiments. In certain embodiments, a daily dosage regimen is administered as a single daily dose. In certain embodiments, a daily dosage regimen is administered as two, three, four, or more than four doses.

In certain embodiments, a pharmaceutical agent of the present embodiments is administered by continuous intravenous infusion. In certain of such embodiments, from 0.1 mg to 500 mg of a composition of the present embodiments is administered per day.

In certain embodiments, a pharmaceutical agent of the present embodiments is administered for a period of continuous therapy. For example, a pharmaceutical agent of the present embodiments may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present embodiments at an amount sufficient to achieve a desired effect. In certain of such embodiments the plasma concentration is maintained above the minimal effective concentration (MEC). In certain embodiments, pharmaceutical agents of the present embodiments are administered with a dosage regimen designed to maintain a concentration above the MEC for 10-90% of the time, between 30-90% of the time, or between 50-90% of the time.

In certain embodiments in which a pharmaceutical agent is administered locally, the dosage regimen is adjusted to achieve a desired local concentration of a compound of the present embodiments.

In certain embodiments, a pharmaceutical agent may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the present embodiments formulated in a compatible pharmaceutical carrier may also be prepared, placed in an appropriate container, and labeled for treatment of an indicated condition.

In certain embodiments, a pharmaceutical agent is in powder form for constitution with a suitable vehicle, e.g., sterile pyrogen-free water, before use.

Methods of Treatment

Based on the teachings provided herein, the compounds provided herein can be used in methods of treating or relieving the symptoms of diseases such as neutrophil infiltration, hemorrhagic shock, inflammatory bowel disease, or lung inflammation. In many embodiments, the compounds as described herein can be administered for a period of about 1 day to about 7 days, or about 1 week to about 2 weeks, or about 2 weeks to about 3 weeks, or about 3 weeks to about 4 weeks, or about 1 month to about 2 months, or about 3 months to about 4 months, or about 4 months to about 6 months, or about 6 months to about 8 months, or about 8 months to about 12 months, or at least one year, and may be administered over longer periods of time. The $p67^{phox}$ protein inhibitor compounds as described herein can be administered 5 times per day, 4 times per day, 3 times per day or 2 times per day. In other embodiments, the $p67^{phox}$ protein inhibitor compound is administered as a continuous infusion.

In many embodiments, an compounds as described herein of the embodiments can be administered orally.

In connection with the above-described methods for the treatment of neutrophil infiltration, hemorrhagic shock, inflammatory bowel disease, or lung inflammation in a patient, a compound as described herein may be administered to the patient at a dosage from about 0.01 mg to about 100 mg/kg patient bodyweight per day, in 1 to 5 divided doses per day. In some embodiments, the compounds as described herein can be administered at a dosage of about 0.5 mg to about 75 mg/kg patient bodyweight per day, in 1 to 5 divided doses per day.

The amount of active ingredient that may be combined with carrier materials to produce a dosage form can vary depending on the host to be treated and the particular mode of administration. A typical pharmaceutical preparation can contain from about 5% to about 95% active ingredient (w/w). In other embodiments, the pharmaceutical preparation can contain from about 20% to about 80% active ingredient.

Those of skill will readily appreciate that dose levels can vary as a function of the specific compound, the severity of the symptoms and the susceptibility of the subject to side effects. Preferred dosages for a given compound as described herein can be readily determinable by those of skill in the art by a variety of means.

In certain embodiments, multiple doses of $p67^{phox}$ protein inhibitor compound are administered. For example, an $p67^{phox}$ protein inhibitor compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Certain Synthesis Methods

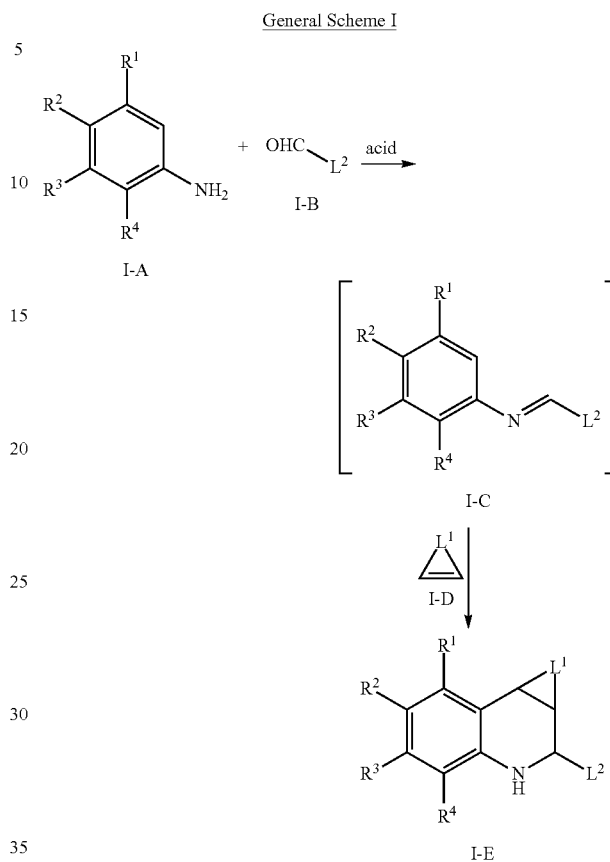

General Scheme I

The process of General Scheme I describes the general synthesis of compounds of general structure I-E, wherein $R^1$, $R^2$, $R^3$, and $R^4$ are defined as disclosed and described herein; $L^1$ is defined as disclosed and described herein; and $L^2$ is defined as disclosed and described herein. Reaction of a compound of general Formula I-A and a compound of general Formula I-B in the presence of an acid such as trifluoroacetic acid (TFA) or $VCl_3$ and an organic solvent such as acetonitrile provides an imine intermediate I-C which can then be reacted with a compound of general Formula I-D to provide the desired compound of general Formula I-E. Alternatively, a compound of general Formula I-A, general Formula I-B and general Formula I-D can be reacted together in the presence of an acid such as trifluoroacetic acid (TFA) or $VCl_3$ and an organic solvent such as acetonitrile to provide the desired compound of general Formula I-E.

General Procedure I-I

A mixture of aniline (I-A; 5 mmol), aldehyde (I-B; 5 mmol) and alkene (I-D; 2-5 eq.) in acetonitrile (10-15 mL) were treated with trifluoroacetic acid (1.1 eq) or $VCl_3$ (0.2 eq) at room temperature. The mixture was stirred at room temperature until completion of the reaction. The mixture was concentrated on a rotary evaporator to provide a residue. The residue was dissolved in ethyl acetate and transferred into a separatory funnel. The organic mixture was washed with water, saturated sodium bicarbonate and brine. The organic layer was collected and dried over anhydrous sodium sulfate. The solvent was concentrated on a rotary evaporator. The residue obtained after concentration was purified on a column of silica gel using 5-25% ethyl acetate hexane to provide the desired compounds of general Formula I-E.

The following compounds listed in Table 1 were prepared according to General Procedure I-I modified using the appropriate chemical reagents to obtain the desired compounds. The structure of the compounds listed in Table 1 were confirmed by $^1$H-NMR spectroscopy and LCMS.

TABLE 1

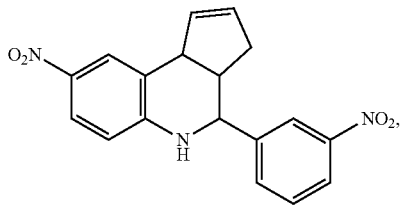 [SMILES: O=[N+]([O-])c1cccc(C2Nc3ccc([N+](=O)[O-])cc3C3C=CCC32)c1]

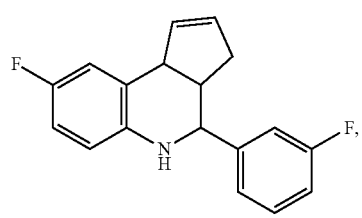 [SMILES: Fc1cccc(C2Nc3ccc(F)cc3C3C=CCC32)c1]

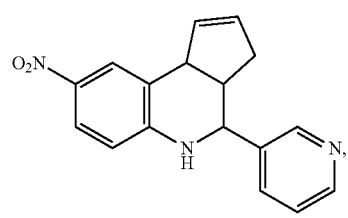 [SMILES: O=[N+]([O-])c1ccc2c(c1)C1C=CCC1C(c1cccnc1)N2]

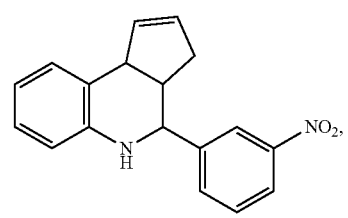 [SMILES: O=[N+]([O-])c1cccc(C2Nc3ccccc3C3C=CCC32)c1]

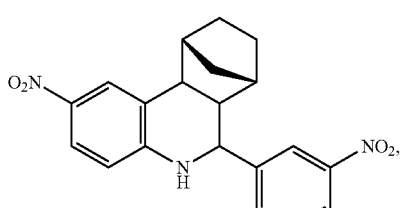

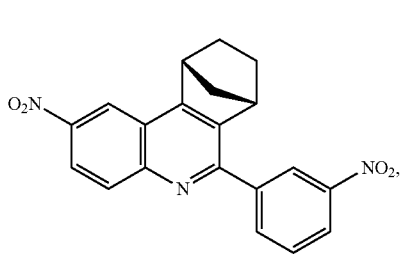 [SMILES: O=[N+]([O-])c1cccc(-c2nc3ccc([N+](=O)[O-])cc3c3c2[C@H]2CC[C@@H]3C2)c1]

TABLE 1-continued

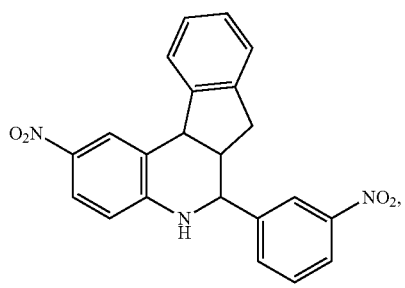 [SMILES: O=[N+]([O-])c1cccc(C2Nc3ccc([N+](=O)[O-])cc3C3c4ccccc4CC23)c1]

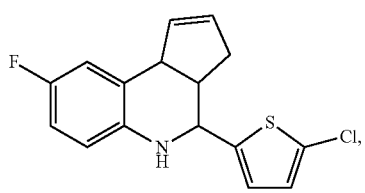 [SMILES: Fc1ccc2c(c1)C1C=CCC1C(c1ccc(Cl)s1)N2]

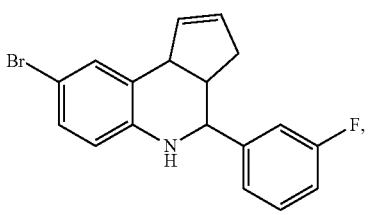 [SMILES: Fc1cccc(C2Nc3ccc(Br)cc3C3C=CCC32)c1]

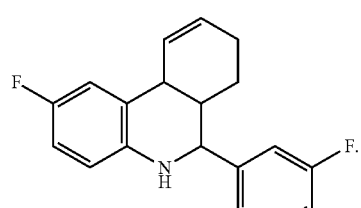

The following compounds listed in Table 2 can be prepared according to General Procedure I-I modified using the appropriate chemical reagents to obtain the desired compounds.

TABLE 2

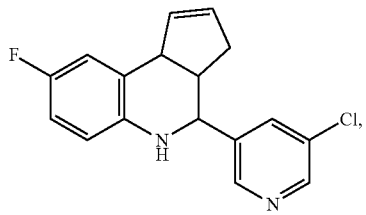 [SMILES: Fc1ccc2c(c1)C1C=CCC1C(c1cncc(Cl)c1)N2]

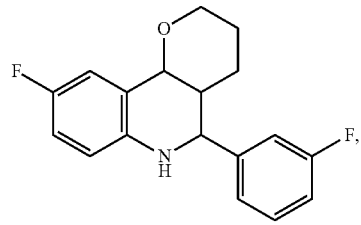 [SMILES: Fc1cccc(C2Nc3ccc(F)cc3C3OCCCC23)c1]

TABLE 2-continued

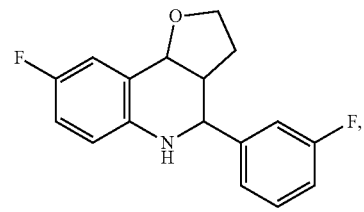 [SMILES: Fc1cccc(C2Nc3ccc(F)cc3C3OCCC23)c1]

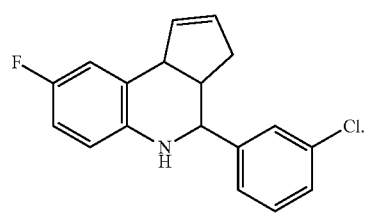 [SMILES: Fc1ccc2c(c1)C1C=CCC1C(c1cccc(Cl)c1)N2]

The following compounds listed in Table 3 were prepared according to General Procedure I-I modified using the appropriate chemical reagents to obtain the desired compounds. The structure of the compounds listed in Table 3 were confirmed by ¹H-NMR spectroscopy and LCMS.

TABLE 3

| Compound Number | Structure |
| --- | --- |
| 101 | 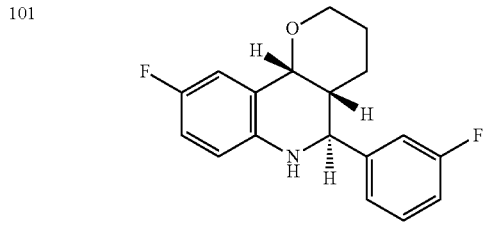 |
| 102 | 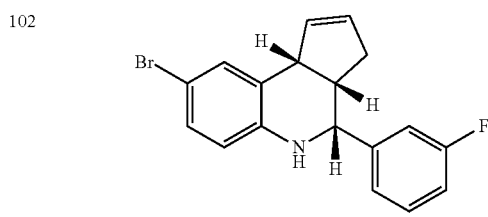 |
| 103 | 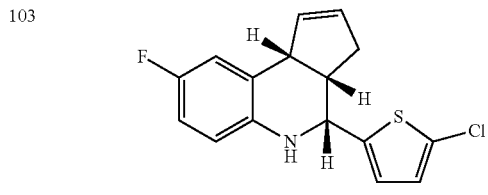 |
| 104 | 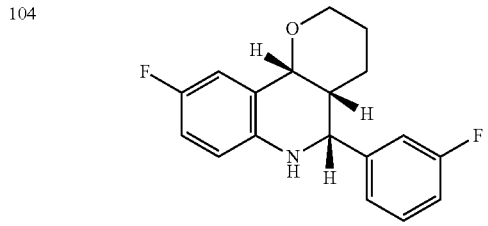 |

TABLE 3-continued

| Compound Number | Structure |
| --- | --- |
| 105 | 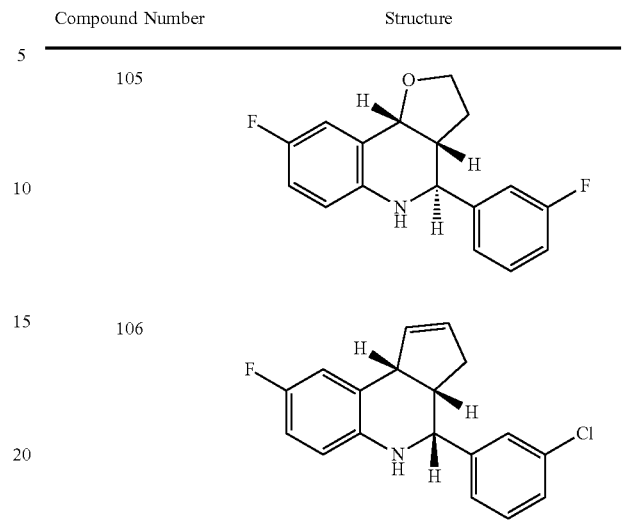 |
| 106 | 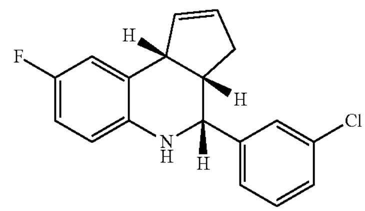 [SMILES: Fc1ccc2c(c1)[C@@H]1C=CC[C@@H]1[C@H](c1cccc(Cl)c1)N2] |
| 107 | 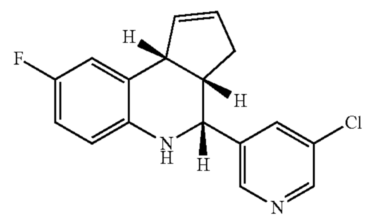 [SMILES: Fc1ccc2c(c1)[C@@H]1C=CC[C@@H]1[C@H](c1cncc(Cl)c1)N2] |
| 108 | 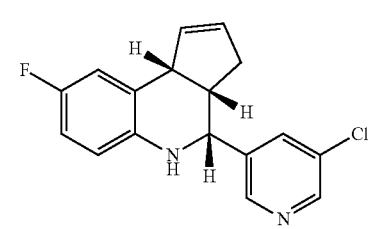<br>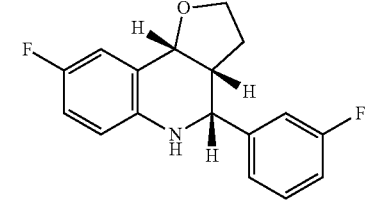 [SMILES: Fc1cccc([C@@H]2Nc3ccc(F)cc3[C@@H]3OCC[C@H]23)c1] |

General Scheme II

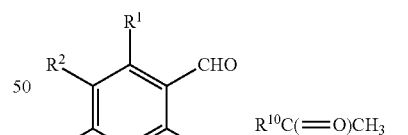

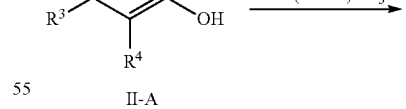

II-A

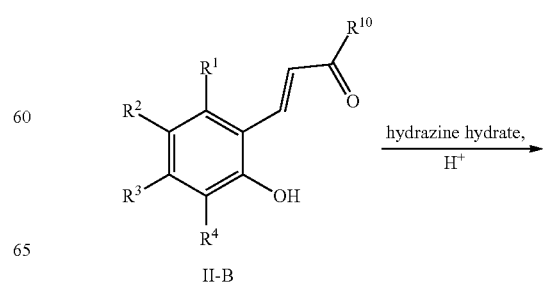

II-B

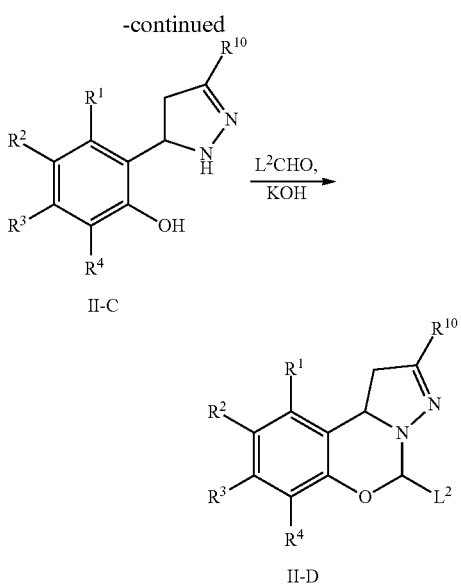

II-C

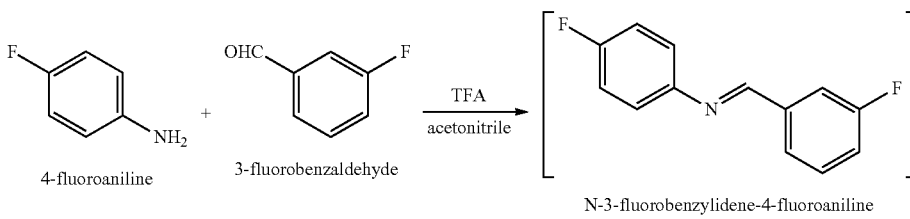

II-D

General Scheme II provides compounds of general structure II-D, wherein $R^1$, $R^2$, $R^3$, $R^4$, and $R^{10}$ are defined as disclosed and described herein; and $L^2$ is defined as disclosed and described herein. Reaction of a compound of general Formula II-A and $R^{10}C(\!=\!O)CH_3$ in the presence of an acid or a base can provide an α,β unsaturated ketone II-B which can then be reacted with hydrazine hydrate, for example under acidic conditions, to provide the a compound of general Formula II-C. Reaction of a compound of a compound of general Formula II-C and $L^2CHO$ in the presence of an acid or a base, for example KOH, can provide the desired compound of general Formula II-D. Compounds of general Formula II-D can be synthesized using methods known to those of skill in the art, for example according to procedures of Orlov et al., "Substituted 1,10b-dihydro-5H-pyrazolo[1,5-c]-1,3-benzoxazines," *Chem. Heterocycl. Compd.*, 1991, Volume 27, Number 8, Pages 910-914 and Svetlik et al., "Synthesis of some pyrazolo[1,5-c][1,3]benzoxazines and a new 5H-pyrazolo[1,5-c][1,3,2]benzoxazaphosphorine ring system," *J. Heterocycl. Chem.*, September/October 2005, Volume 42, Issue 6, pages 1143-1147.

EXAMPLES

The following examples are set forth merely to assist in understanding the embodiments and should not be construed as limiting the embodiments described and claimed herein in any way. Variations of the invention, including the substitution of all equivalents now known or later developed, which would be within the purview of those skilled in the art, and changes in formulation or minor changes in experimental design, are to be considered to fall within the scope of the embodiments incorporated herein.

Example 1

Scheme I-I

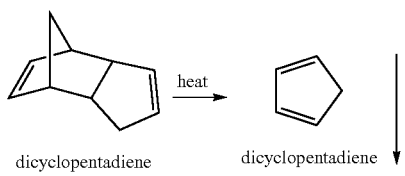

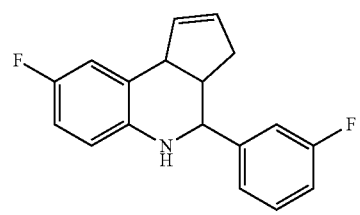

100

Method I-A:

The reaction of 4-fluoroaniline and 3-fluorobenzaldehyde in TFA and acetonitrile provided the N-3-fluorobenzylidene-4-fluoroaniline. The cyclopentadiene was separately prepared from its dimer dicyclopentadiene. The dimer was heated at 180° C. to give monomer, which was reacted with N-3-fluorobenzylidene-4-fluoroaniline in acetonitrile in presence of TFA to provide the desired difluoro compound 100.

Example 2

Experimental Procedures

Protein Purification, Mutagenesis, Microscale Thermophoresis—

The p67$^{phox}$ protein was expressed in BL21(DE3) bacteria (Stratagene) using the pET30-HIS p67(1-212) plasmid. Protein was purified using the QIAexpress Ni-NTA kit (Qiagen) or the GST Bind Resin Chromatography Kit (Novagen) for RacV12 and RacWT proteins. Mutagenesis was carried out using the Quick Change Lightening Site Directed Mutagenesis Kit (Stratagene).

Proteins were labeled for microscale thermophoresis using the Monolith NT Protein Labeling Kit Red (Nano Temper Technologies) as recommended by the manufacturer. Binding reactions were carried out using the Monolith NT.115 (Nano Temper Technologies). Binding data was analyzed using Graphpad Prizm to estimate Kd values. The arbitrary fluorescence value from the thermophoresis plots for the smallest compound titration was subtracted from every other data point (Delta depletion) prior to normalization to a Vmax of 100. In thermophoresis plots where there was no binding, a curve could not be fit and therefore no Vmax could be assigned. In these instances the highest delta depletion value was set to 100 and all data were normalized accordingly.

Cell Culture—

HL-60 cells were propagated in RPMI 1640 medium containing 10% heat inactivated fetal bovine serum, 2 mM L-glutamine, 100 U/mL penicillin/streptomycin at 37° C. in air containing 5% $CO_2$. For differentiation, HL-60 cells were cultured in 1.3% dimethyl sulfoxide (DMSO) as previously described (Servant, G., et al. (1999) Mol Biol Cell 10, 1163-1178, hereby incorporated by reference in its entirety). Primary murine neutrophils were isolated from C57Bl/6 mouse bone marrow according to a published protocol (Filippi et al., (2004) Nat Immunol 5, 744-751, hereby incorporated by reference in its entirety) using a discontinuous Percoll (Pharmacia) gradient and were utilized immediately in experiments. Human neutrophils were obtained from fresh blood (IRB #2010-1855, Cincinnati Children's Hospital medical Center) following a well established protocol using density gradient separation from whole blood (Oh et al. (2008) J Vis Exp., 17, pii: 745, hereby incorporated by reference in its entirety).

Chemicals and Synthesis—

PMA, apocynin, $H_2O_2$, DPI chloride, DTT, HRP, glucose oxidase, xanthine, xanthine oxidase were purchased from Sigma Aldrich.

Immunoblot Analysis—

Whole-cell lysates were prepared by cell extraction using lysis buffer containing 20 mM Tris-HCl (pH 7.6), 100 mM NaCl, 10 mM $MgCl_2$, 1% Triton X-100, 0.2% sodium deoxycholate, 1 mM phenylmethylsulfonyl fluoride, 10 μg/mL of leupeptin, 1 μg/mL of aprotinin, and 1 mM dithiothreitol for 30 min. Equal amounts of protein, as determined by Bradford assay, were resolved by SDS-PAGE. Specific proteins were detected by standard 9 immunoblotting procedures using the following primary antibodies: (Cell Signaling, 1:500 dilution) phospho-PAK1 (Ser144)/PAK2 (Ser141), (Sigma-Aldrich 1:500) β-Actin.

Flow Cytometry—

Cells ($5\times10^5$) were harvested and processed for Annexin V/7AAD staining according to manufacturer's protocol (Becton Dickinson). Flow cytometry data were acquired on a FACS Canto bench-top flow cytometer (Becton Dickinson) and the cell cycle distributions were determined by an BrdU incorporation assay using Flo-Jo software (Bosco et al (2010) Blood 115, 3320-3328, hereby incorporated by reference in its entirety). For ROS production assay, primary murine neutrophils or dHL60 cells were incubated with compound for 2 hours prior to addition of H2-DCFDA according to manufacturer's instructions (Molecular Probes). Cells were then stimulated with 10 μM fMLP (Sigma), 1 mM $CaCl_2$, and 1.5 mM $MgCl_2$ for 15 minutes prior to wash and FACS analysis for mean fluorescence intensity. Non-fMLP stimulated control values were subtracted from all samples before normalization to fMLP-stimulated, vehicle control treated sample in order to display percent ROS inhibition.

F-Actin Immunofluorescence—

Cells were pretreated with compound for 40 minutes prior to wash, and resuspended in HBSS with compound. Cells were allowed to adhere to fibronectin (Sigma Aldrich) coated glass coverslips (15 min) and then stimulated with 100 nM fMLP (3 min). Coverslips were then fixed with 3.7% paraformaldehyde (Sigma Aldrich) and then staining for Factin was performed with rhodamine phalloidin per the manufacturer's instructions (Molecular Probes).

Nitroblue Tetrazolium (NBT) Assay—

Primary neutrophils from mouse bone marrow were subjected to fMLP stimulation in the presence or absence of various chemicals for 5 min. Cells were stained for NBT activity as previously described in the incorporated materials of Filippi et al. (2004) to reveal relative ROS production.

Luminol Chemiluminescence Assay—

Human neutrophils ($2\times10^5$) were stimulated in HBSS supplemented with 0.1% BSA, 1 mM Ca2+, 1 mM Mg2+ and with fMLP (10M), PMA (300 nM) or glucose oxidase (200 mU/ml) for 30 min in the presence of 10 μM [8-amino-5-chloro-7-phenylpyrido[3,4-d]pyridazine-1,4(2H,3H)dione] (L012).

Chemiluminescence was measured using GloMax®-96 Microplate Luminometer (Promega) (Tarpey et al., (2004) Am J Physiol Regul Integr Comp Physiol 286: R431-R444, hereby incorporated by reference in its entirety). The generation of hydrogen peroxide by the xanthine/xanthine oxidase was performed in PBS supplemented with xanthine oxidase (0.004 U), HRP (0.005 $U \cdot mL^{-1}$) and L012, following the protocol described in Wind et al., (2010) Br J Pharmacol. 161, 885-898, hereby incorporated by reference in its entirety. The reaction was started by the addition of xanthine (0.5 mM).

Amaxa Transfection of Primary Neutrophils—

Primary mouse neutrophils were suspended in 100 μl NucleofectorR solution with 10 μg plasmid pCDNA3-NOX4 encoding NOX4 or mock vector. Cells were transfected using a Cell Line V NucleofactorTMR kit (Amaxa Biosystem, Amaxa Inc.) and the Nucleofector™ program Y-001. Cells were recovered at 37° C. for 2 hours and subjected to the luminol chemiluminescence assay using 10 μM L012 and HRP (0.005 $U \cdot mL^{-1}$) to record ROS produced by NOX4 expression.

Example 3

Phox-I1 Binds to p67$^{phox}$ Target

To test the ability of compounds identified by preliminary screening to bind to the p67$^{phox}$ protein in the N-terminal 200 amino acid region involved in Rac1-GTP interaction, microscale thermophoresis was employed. This technology probes for fluorescent changes in the hydration shell of molecules in order to measure protein-protein or protein small molecule interactions with high sensitivity in near-native conditions.

One of the compounds identified by preliminary screening is shown below, and identified throughout this disclosure as "Phox-I1".

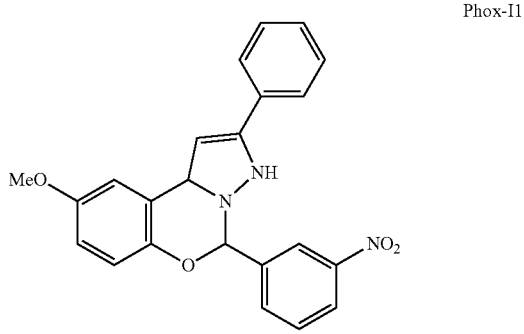 [SMILES: COc1ccc2c(c1)C1C=C(c3ccccc3)NN1C(c1cccc([N+](=O)[O-])c1)O2]

Phox-I1

Figure 1B:
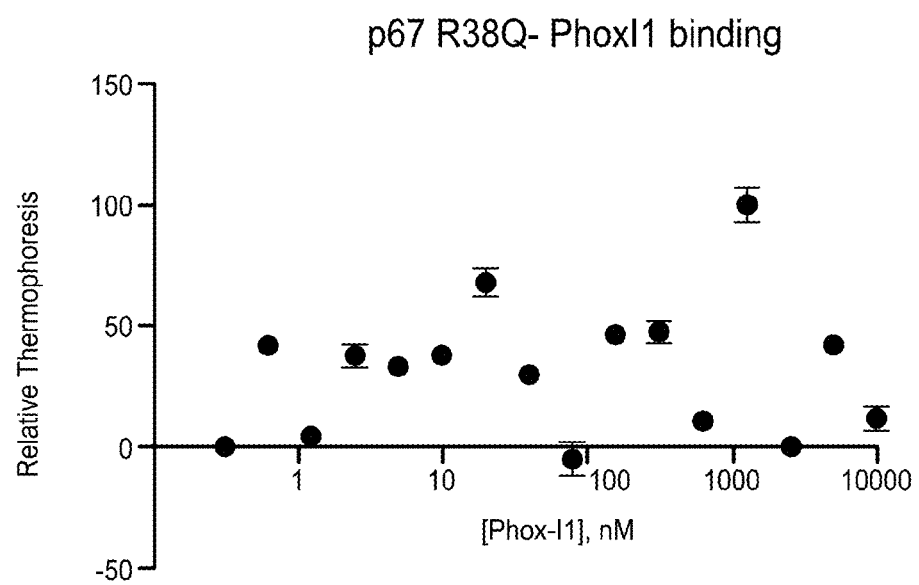
Figure 1C:
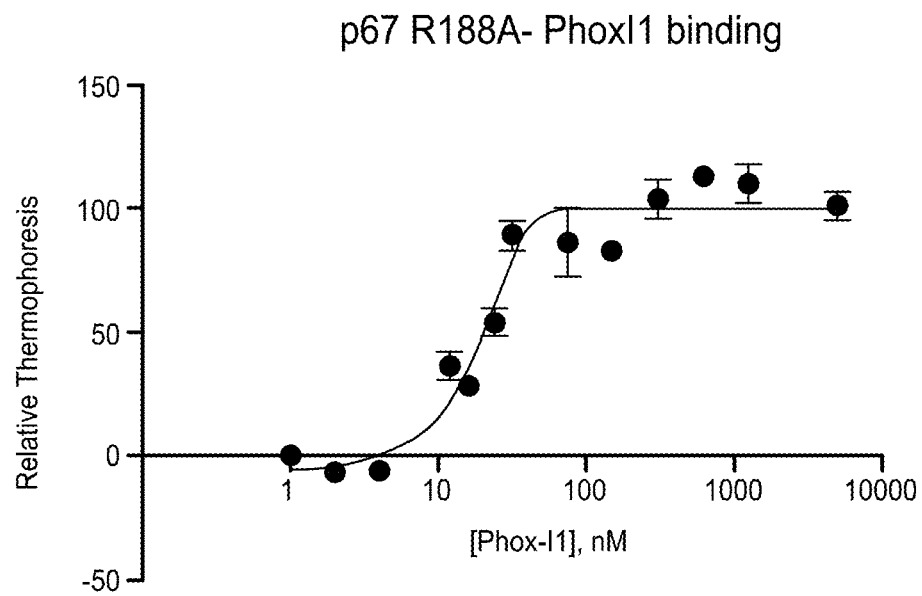
Figure 1D:
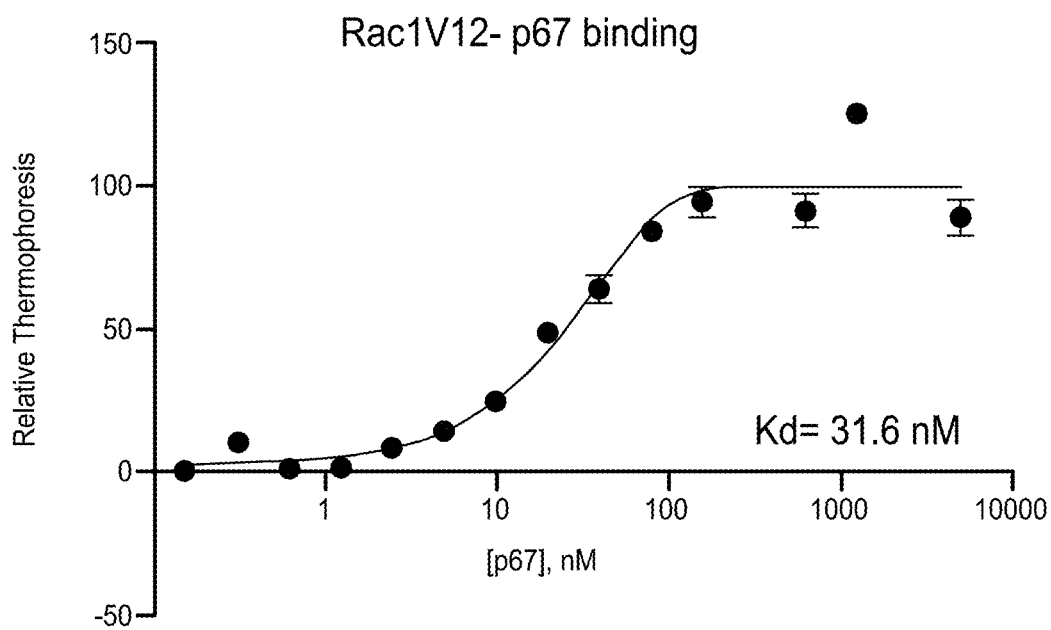
Figure 1E:
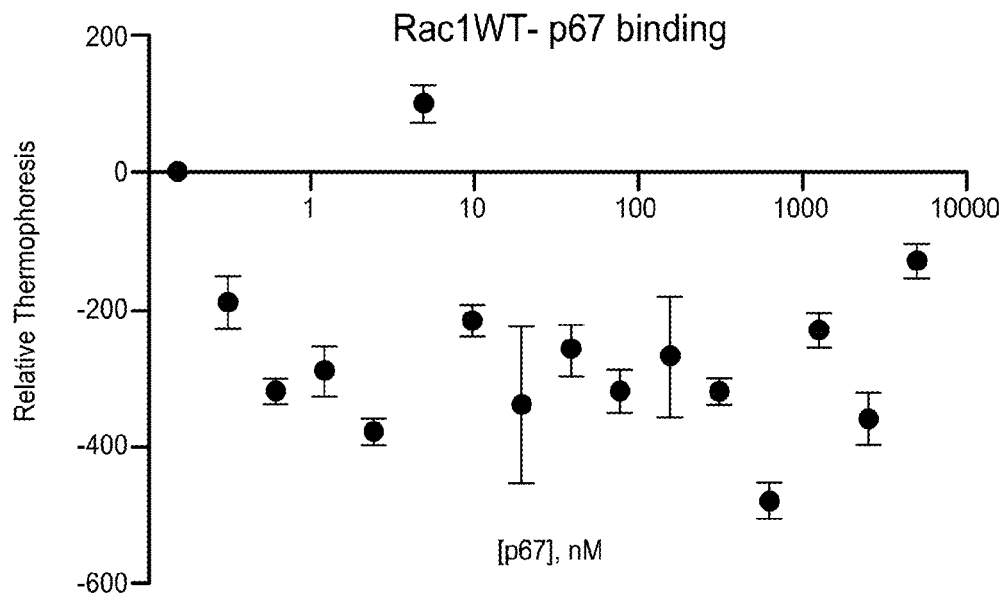
Figure 1F:
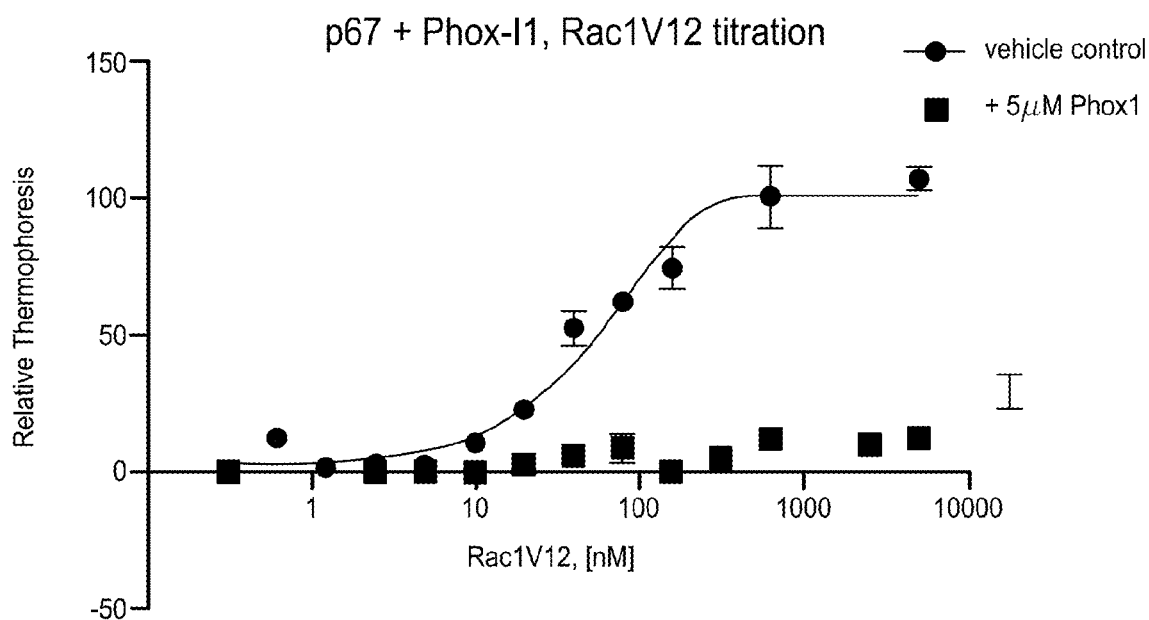
Figure 1G:
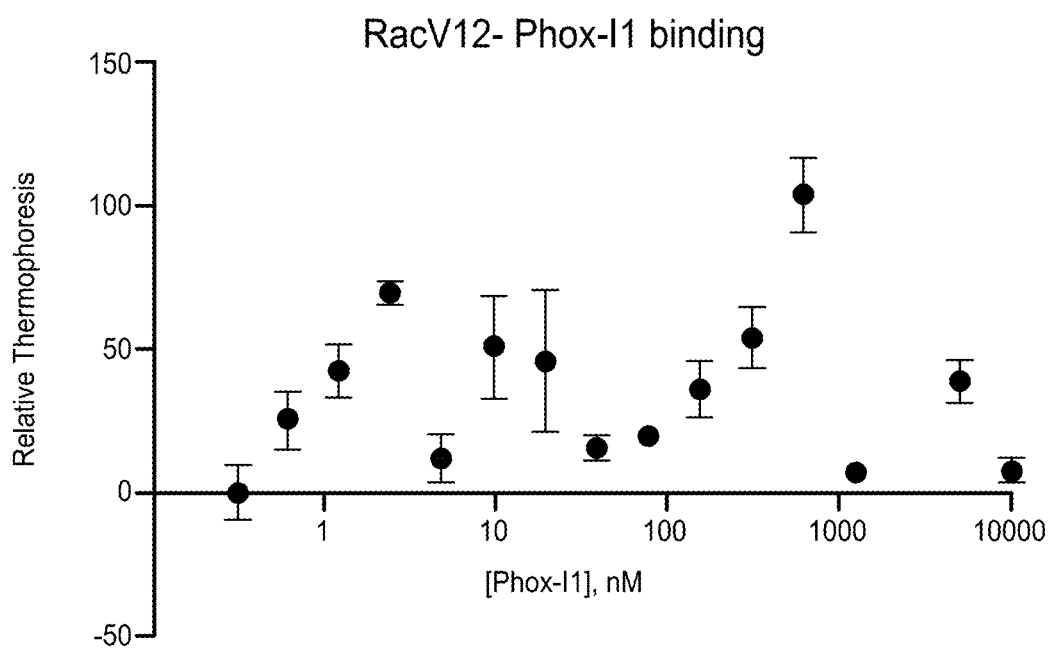

The p67$^{phox}$ N-terminus showed binding activity to the Phox-I1 compound in titration assays, yielding a Kd value of ~100 nM (FIG. 1A). Mutagenesis of R38 residue of p67$^{phox}$, which is critical for Rac1-GTP binding, disrupted the binding ability of Phox-I1 to p67$^{phox}$ (FIG. 1B). As a positive control, a mutant made at residue R188 of p67$^{phox}$, outside of the region critical for interaction with Rac1-GTP, retained the binding activity to Phox-I1 (FIG. 1C). To demonstrate the ability of Phox-I1 to compete with active Rac1 for the binding pocket of p67$^{phox}$, the high-affinity binding activity of the constitutively active Rac1V12 mutant with p67$^{phox}$ was first validated by microscale thermophoresis (FIG. 1D). Rac1-GDP was unable to bind to p67$^{phox}$ in this assay and thus showed specificity of this interaction for the active Rac1 (FIG. 1E). Next, to perform a competition binding, p67$^{phox}$ protein was first incubated with either 5 µM Phox-I1 or an equal volume of vehicle control for 15 min prior to titration of purified Rac1V12 protein. The disruption of p67$^{phox}$ binding to Rac1V12 by Phox-I1, but not vehicle control, was evident (FIG. 1F). Furthermore, as a control for specificity, Rac1V12 protein was incubated with various concentrations of Phox-I1, but no detectable binding was observed (FIG. 1G). Thus, Phox-I1 binding to p67$^{phox}$ is specific and not due to nonspecific effects, such as aggregation. These results indicate that the lead p67$^{phox}$ inhibitor Phox-I1 can bind to the Rac1 interactive site of p67$^{phox}$ specifically and interfere with Rac1-GTP interaction with p67$^{phox}$.

Example 4

Phox-I1 is Active in Suppressing ROS Production in Neutrophils

Figure 2A:
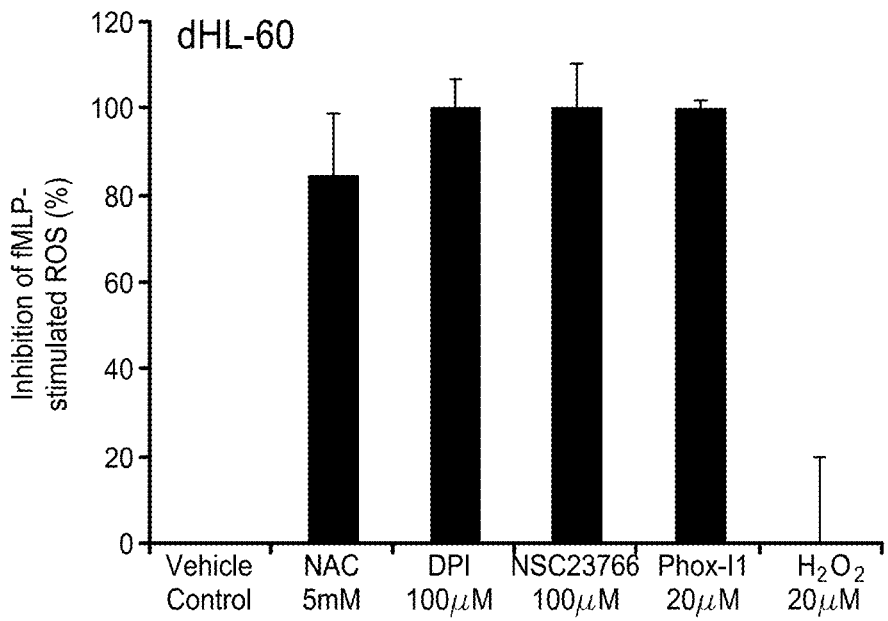
FIGS. 2A-F set forth the experimental results demonstrating that fMLP-stimulated ROS production is abrogated by Phox-I1 in human HL-60 cells and primary murine neutrophils. (A) Ability of Phox-I1 to inhibit ROS production in fMLP-stimulated differentiated HL-60 cells as compared to standard ROS inhibitors was assessed by H2-DCFDA staining and FACS analysis. Levels of ROS production in non-fMLP treated controls were subtracted from all samples, data was then normalized to fMLP-stimulated vehicle treated control. (B) Experiment described in A was repeated with primary murine neutrophils. (C) As described in A, HL-60 cells were treated with various concentrations of Phox-I1 and an IC50 curve was generated. (D) Dose response of fMLP-induced ROS production to Phox-I1 by primary human neutrophils. Levels of ROS production in non-fMLP or fMLP-stimulated human neutrophils were assayed by the luminol chemiluminescence method in increasing concentrations of Phox-I1. Data was normalized to fMLP-stimulated vehicle treated control. (E) Effect of Phox-I on glucose oxidase-generated ROS. (F) Effect of Phox-I1 on PMA induced ROS production in human neutrophils assayed by the luminol chemiluminescence method.
Figure 2B:
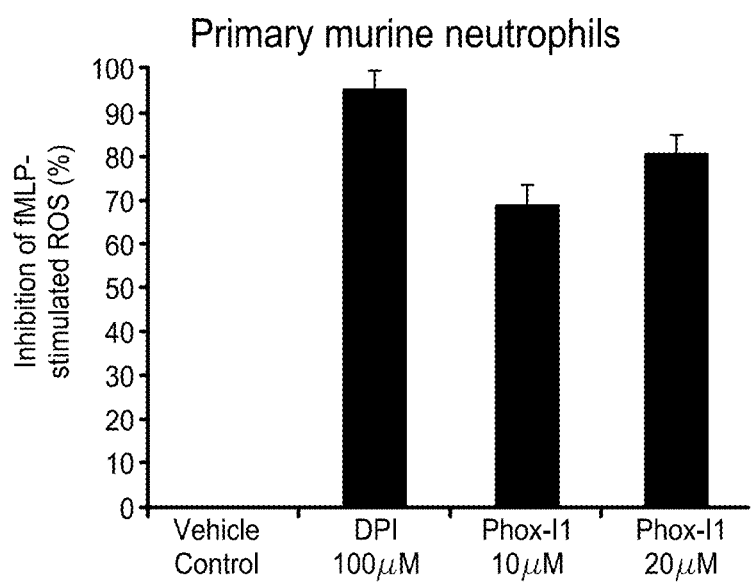
Figure 2C:
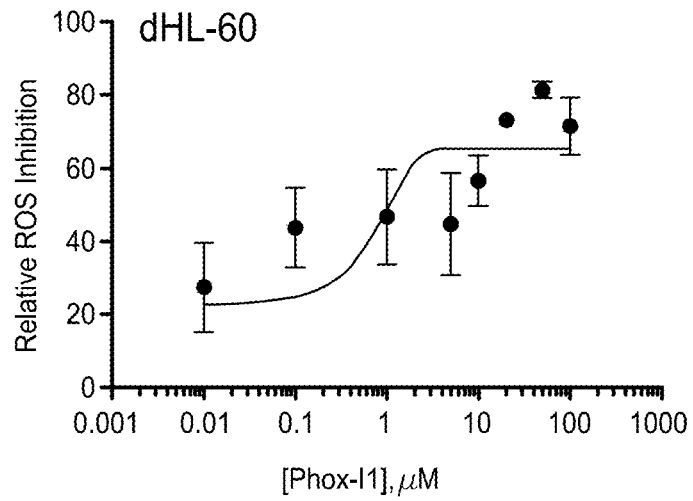

To validate the hits from preliminary screening in cells, several cellular functional assays were performed using different cell types to measure the effect of compounds on inhibition of ROS production. ROS levels were first analyzed by fluorescence-activated cell sorting (FACS) in HL-60 pre-incubated with compounds for 2 hr prior to stimulation of ROS production. The p67$^{phox}$ inhibitor, Phox-I1, was tested against NAC (a ROS scavenger), DPI (a broad range inhibitor of NADPH oxidase), and NSC23766 (a Rac-GTP inhibitor; FIG. 2A). Phox-I1, at 20 µM, was able to attenuate ROS production similarly to 100 µM DPI or 100 µM NSC23766 and slightly more efficiently than 5 mM NAC. $H_2O_2$ added to the cells was included as a positive control for ROS measurement. Second, to test the capacity of Phox-I1 to inhibit ROS production in a primary cell context, primary murine neutrophils isolated from mouse bone marrow were treated with increasing concentrations of Phox-I1 and the efficacy of inhibition of fMLP-stimulated ROS production was analyzed. DPI treatment was included as a positive control for inhibition of ROS production (FIG. 2B). Both 10 µM and 20 µM concentrations of Phox-I1 were able to inhibit ROS production nearly as well as DPI at 100 µM concentration. Next, to ascertain the optimal effective dose for ROS inhibition in cells, a dose titration series of Phox-I1 was administered to dHL-60 cells (FIG. 2C). Optimal cellular response to this compound was achieved at doses of 10 µM with an $IC_{50}$ of ~3 µM.

Figure 2D:
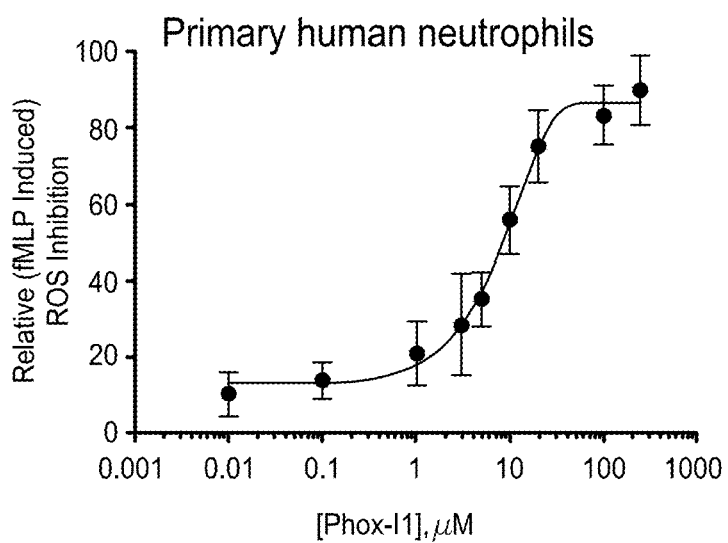
Figure 2E:
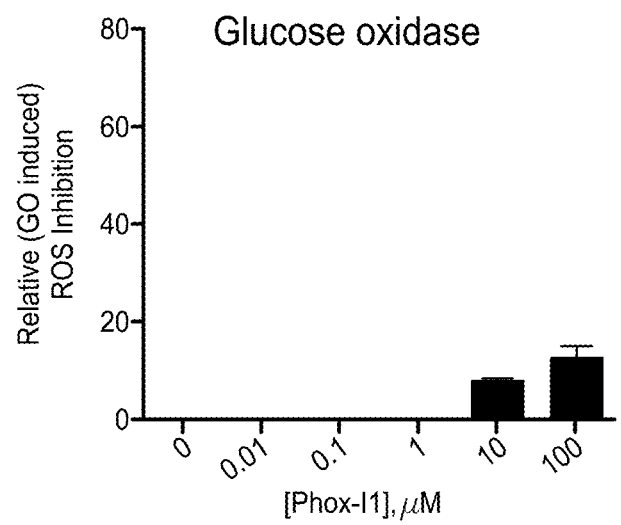
Figure 2F:
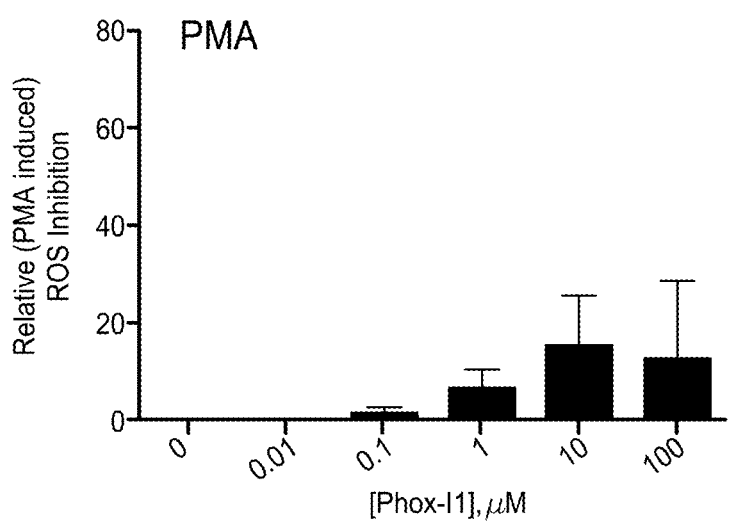

In addition to using the 2'-7'-dichlorodihydrofluorescein diacetate (DCFDA)-based FACS analysis of ROS generation in primary murine neutrophils, the efficacy of Phox-I1 was validated in primary human neutrophils by the luminol chemiluminescence assay. As shown in FIG. 2D, Phox-I1 was able to suppress fMLP-induced ROS production in human neutrophils dose-dependently, with an $IC_{50}$ ~8 µM, based on a one-site competition model. Further, Phox-I1 did not affect the exogenous glucose oxidase-produced ROS (FIG. 2E) or the PMA-induced ROS production that is mediated through a PIP3-independent pathway (FIG. 2F), demonstrating that the fMLP-Rac-p67$^{phox}$ axis may mediate a pathway for NOX2 activation independently from the PMA pathway. These data indicate that Phox-I1 can efficiently inhibit ROS production in the µM range in both human and murine neutrophils.

Example 5

Structure-Activity Relationship Analysis of Phox-I1 Structural Analogs

Figures 1, 3A:
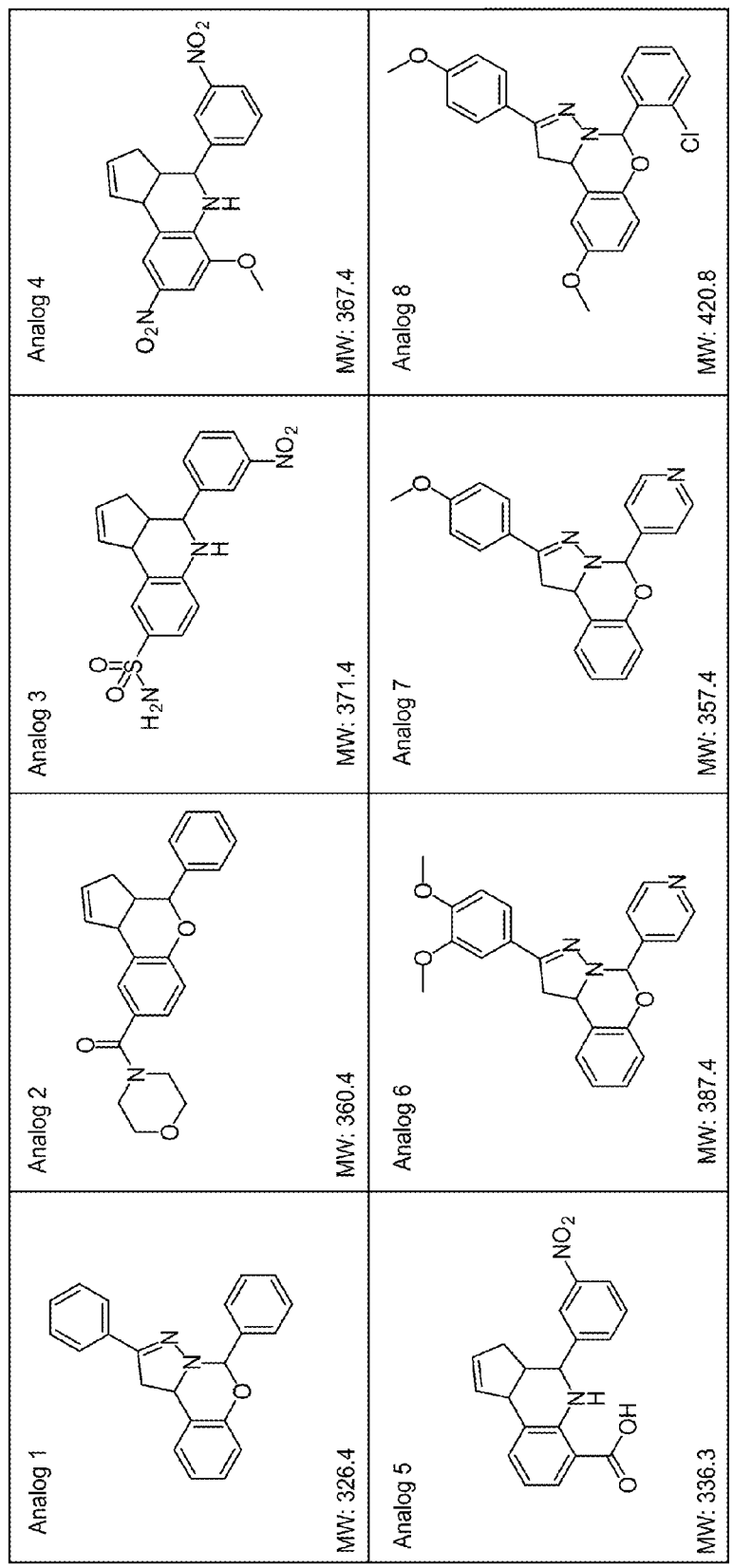
FIGS. 3A-H set forth experimental results demonstrating that Phox-I1-analog analysis yields compounds with improved or similar cellular ROS inhibitory activity. (A) List of analogs derived from a search of the UCDDC and ZINC compound libraries for Phox-I1-like structures with medicinal chemistry features. (B) H2-DCFDA staining in fMLP-stimulated dHL-60 cells treated with Phox-I1 analogs. Analog 4, 10 and 16 (Phox-I2) all display improved ROS inhibition over Phox1. (C) Freshly isolated primary murine neutrophils were stimulated with fMLP to initiate ROS production, cells were then treated with DMSO control, DPI, Phox-I1, or Phox-I2 and a Nitroblue tetrazolium (NBT) assay was performed and imaged (left panel). Blue stain is superoxide anion, pink stain is neutrophil nucleus. Cells displaying ROS production were quantified from the images and non-fMLP treated ROS levels were subtracted prior to normalization to vehicle control treated sample (right panel). (D) Using microscale thermophoresis, $p67^{phox}$ protein binds Phox-I2 with high affinity. (E) IC50 for Phox-I2 was assayed by H2-DCFDA ROS production method in dHL-60 cells. (F) Phox-I2 dosage response of ROS production in human neutrophils assayed by luminol chemiluminescence. (G) As a negative control, Analog 13 was unable to bind $p67^{phox}$. (H) Analog 13 showed no cellular ROS inhibitory activity in HL-60 cells.
Figures 2, 3A:
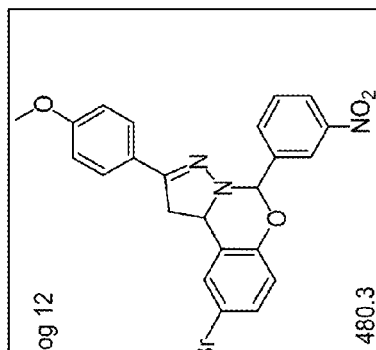
Figure 3B:
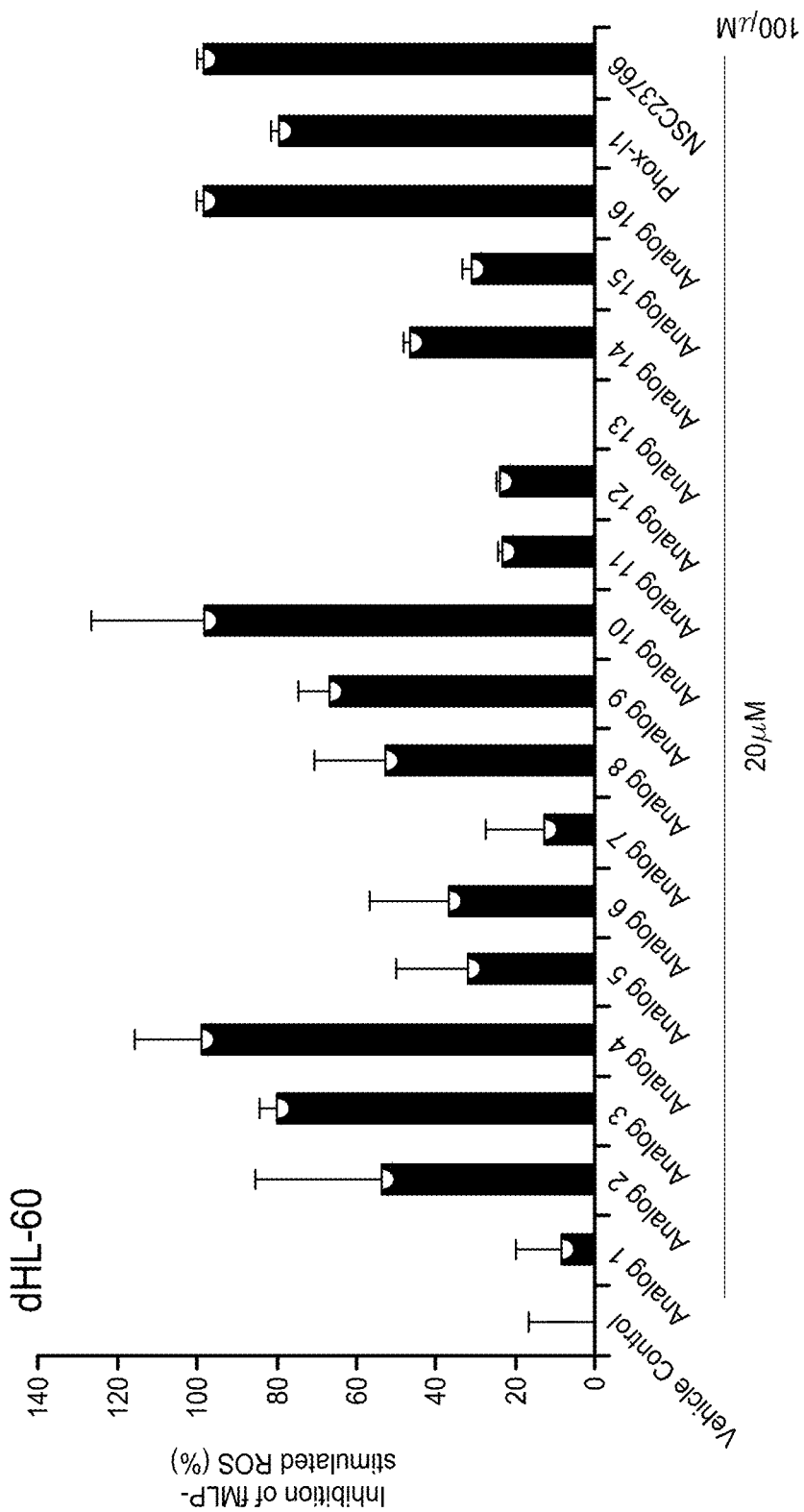

As discussed previously, the preliminary screen led to the identification of Phox-I1 as a lead inhibitor of p67$^{phox}$. To develop a preliminary understanding of the structure-activity relationships (SAR) in these classes, a substructure search of the University of Cincinnati Drug Discovery Core chemical library was conducted. Thirty-five compounds from this search were visually screened in an attempt to explore the structural space with the goals of (1) retaining or improving activity, (2) improving solubility, and/or (3) seeking a replacement of the nitro groups. Toward that end, 16 compounds bearing more polar functional groups and with replacement or altered positions of the nitro groups were selected for further screening (FIG. 3A). To validate the relative potency of the compounds identified in the analog screen, a cellular functional assay of ROS inhibition was performed in differentiated HL-60 cells. Cells were pre-incubated with analogs from FIG. 3A for 2 hr prior to stimulation of ROS production and analysis of ROS levels by FACS (FIG. 3B). Comparing with cells treated with vehicle control, analogs 4, 10, 16, and Phox-I1 displayed the greatest inhibition of ROS production, whereas analogs 1, 7, 11, 12, and 13 showed little or no inhibition of ROS production. Based on the ROS inhibitory activity displayed by analog 16, analog 16 was termed a second-generation lead inhibitor, Phox-I2.

Figure 3C:
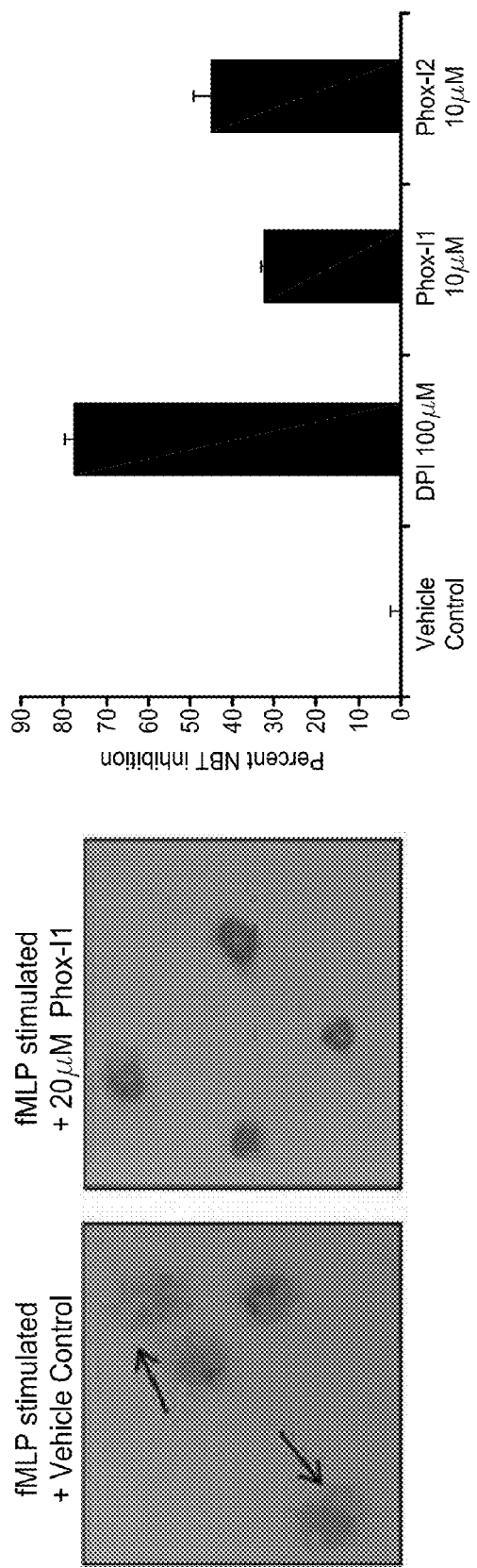

To complement the DCFDA based FACS analysis and the luminol chemiluminescence method, nitroblue tetrazolium (NBT) assays were performed in fMLP-activated primary murine neutrophils (FIG. 3C). These experiments revealed that a 10 µM dose of Phox-I1 resulted in a significant blockade of superoxide production, which was heightened by similar treatment with Phox-I2. Both Phox-I1 and Phox-I2 were more effective at a lower dose than were the working concentration of DPI, which was included as a positive control for ROS inhibition. Thus, the results of these combined assay methods demonstrated that the inhibitors could effectively inhibit ROS production by neutrophils.

Figure 3D:
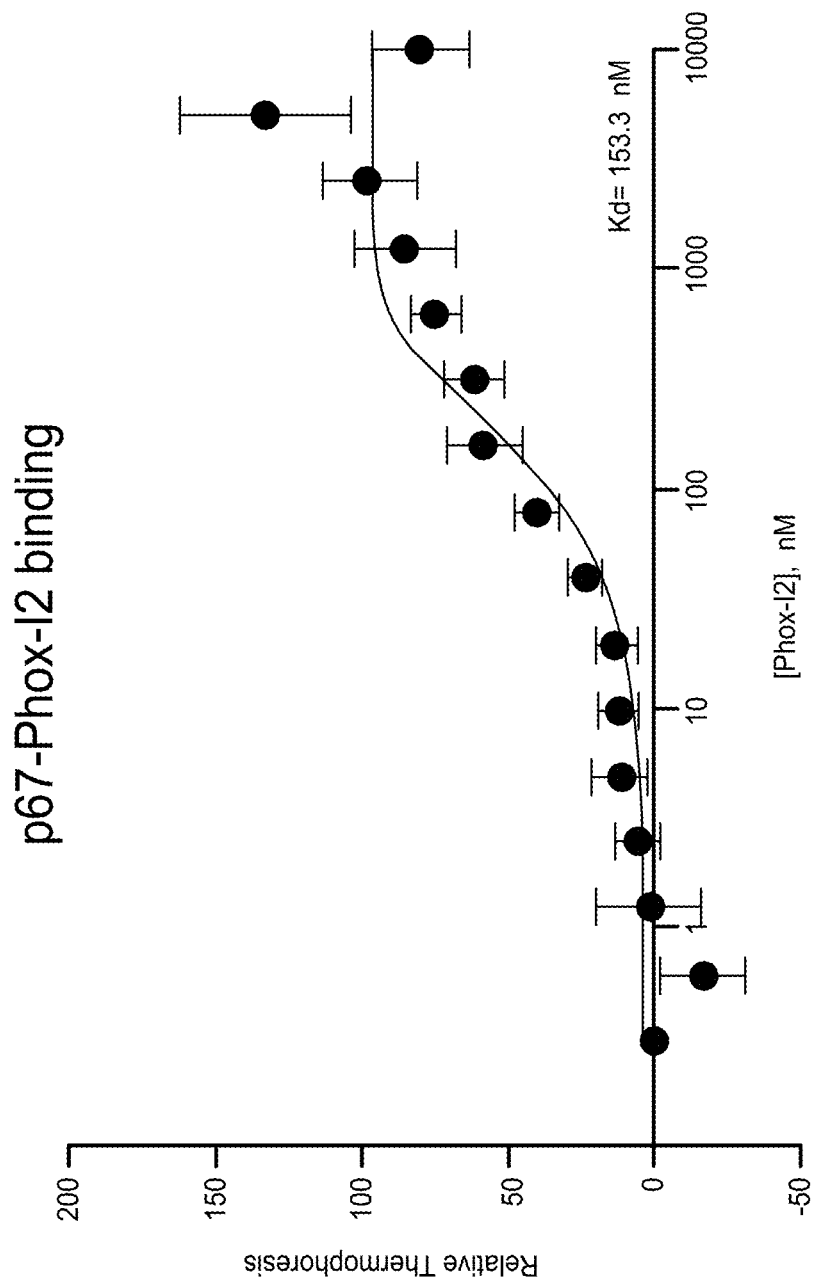
Figure 3E:
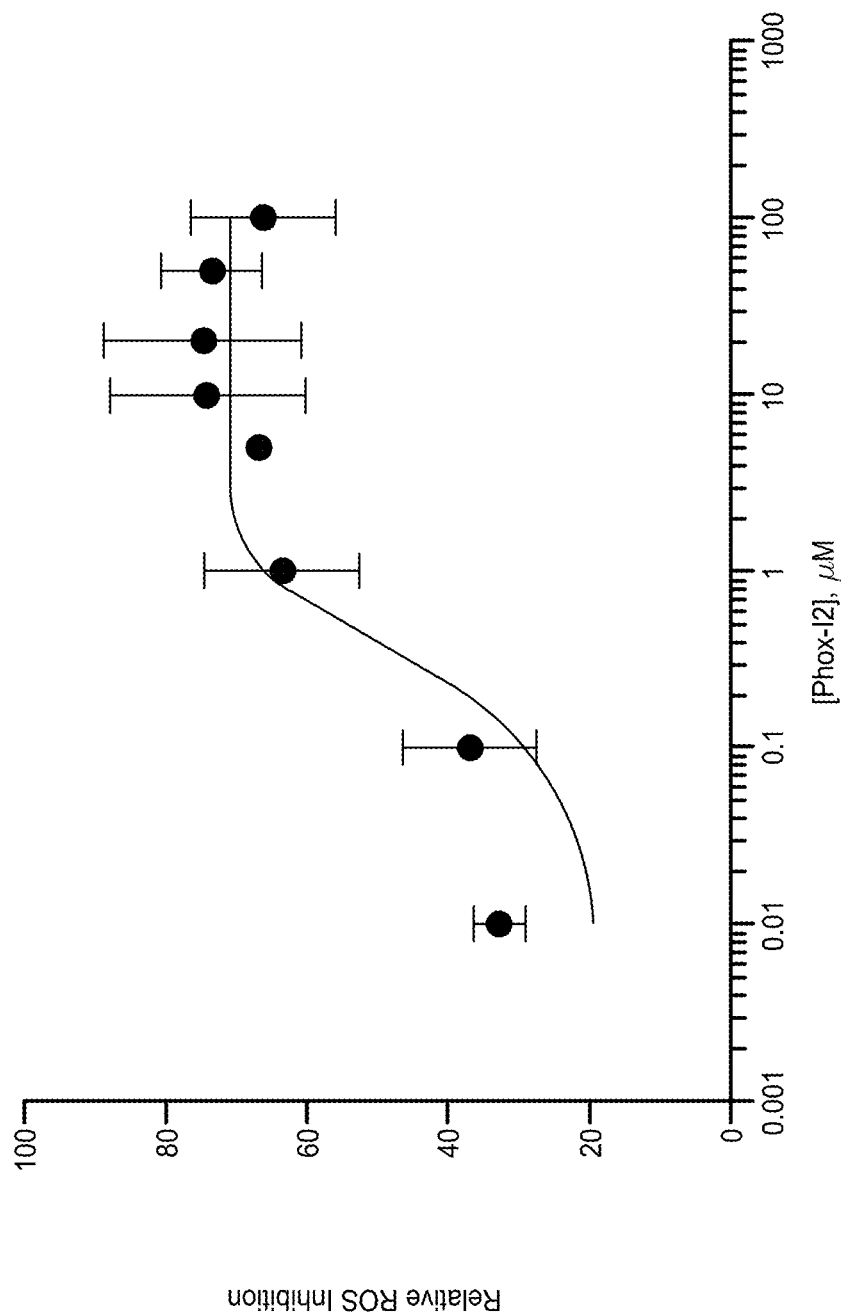
Figure 3F:
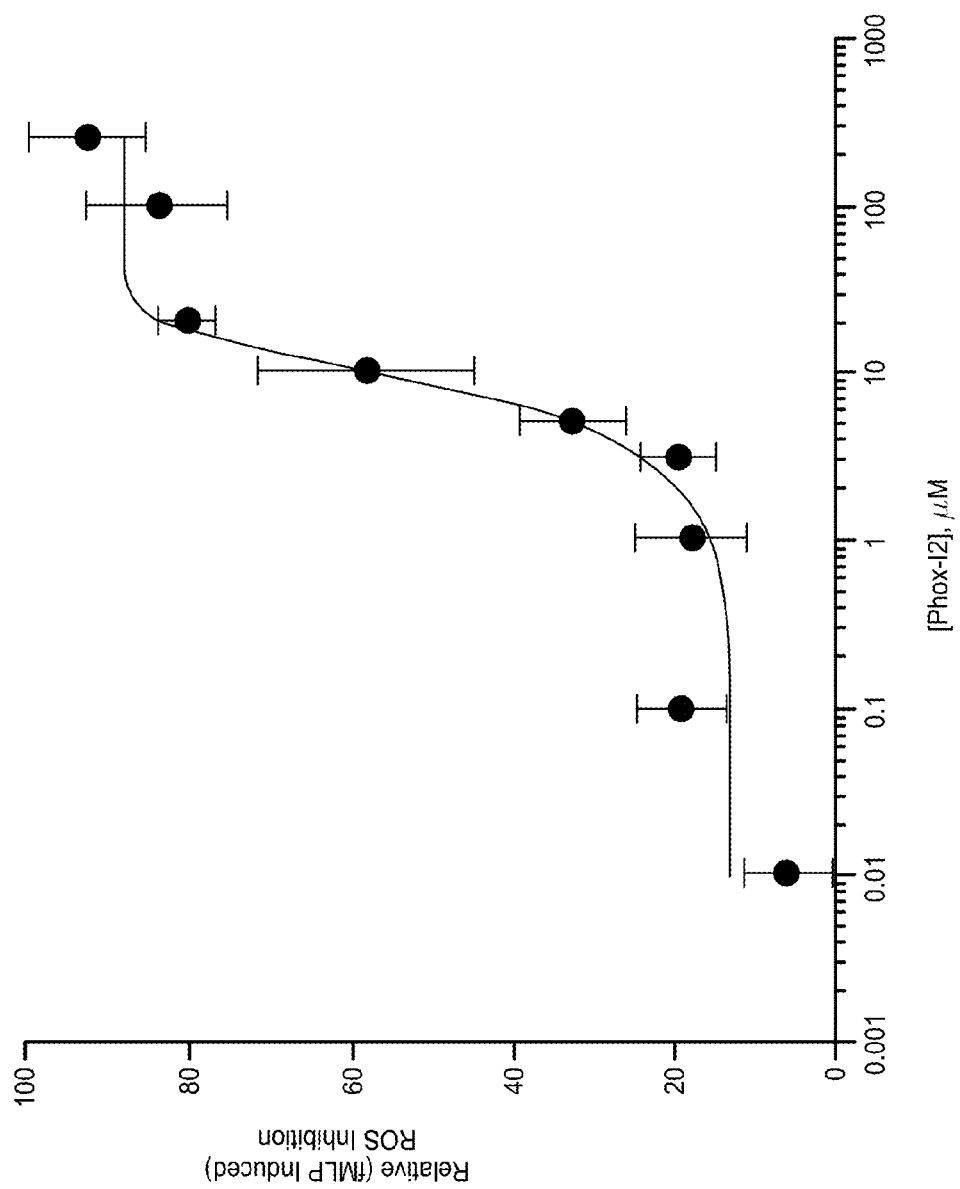
Figure 3G:
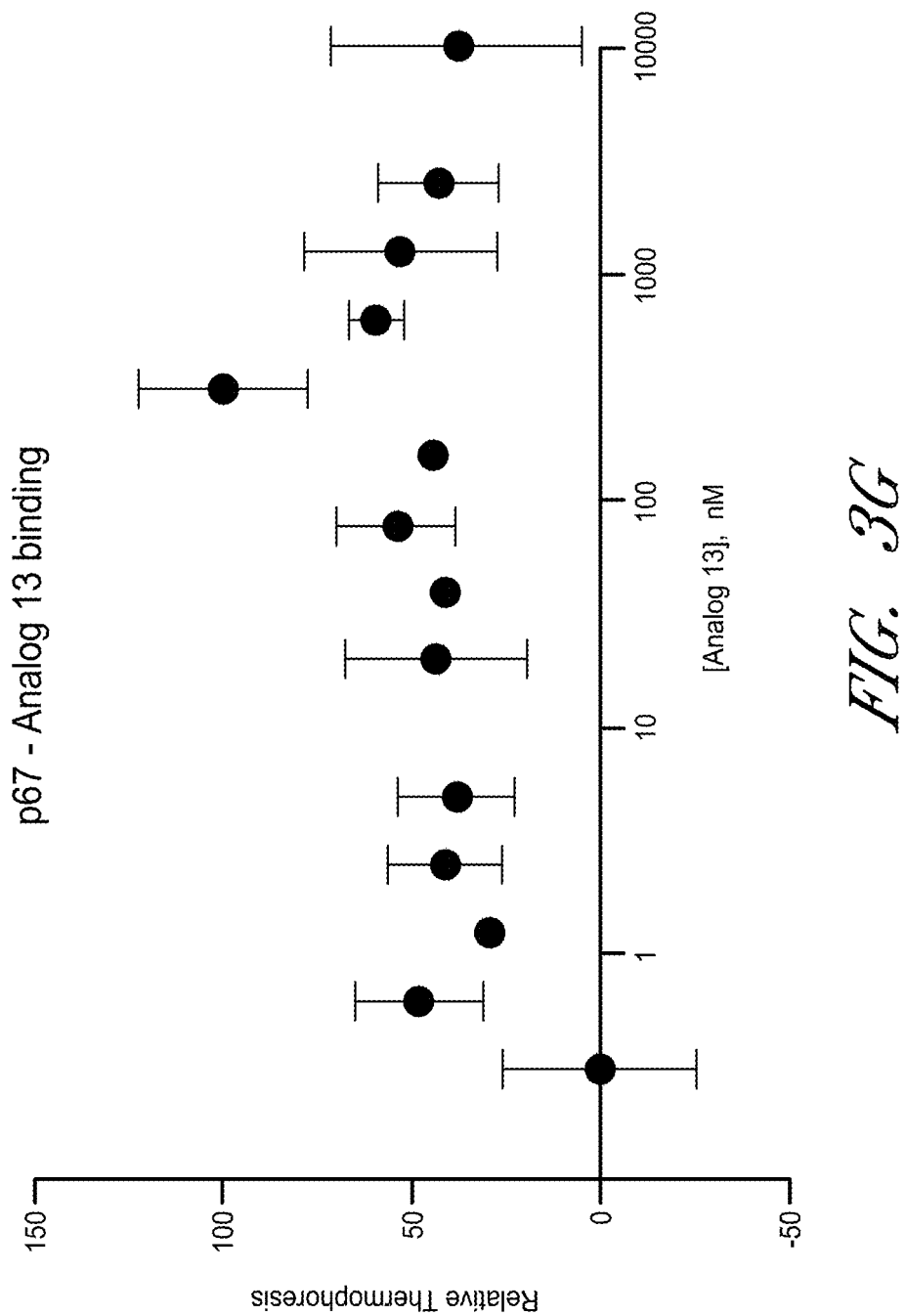
Figure 3H:
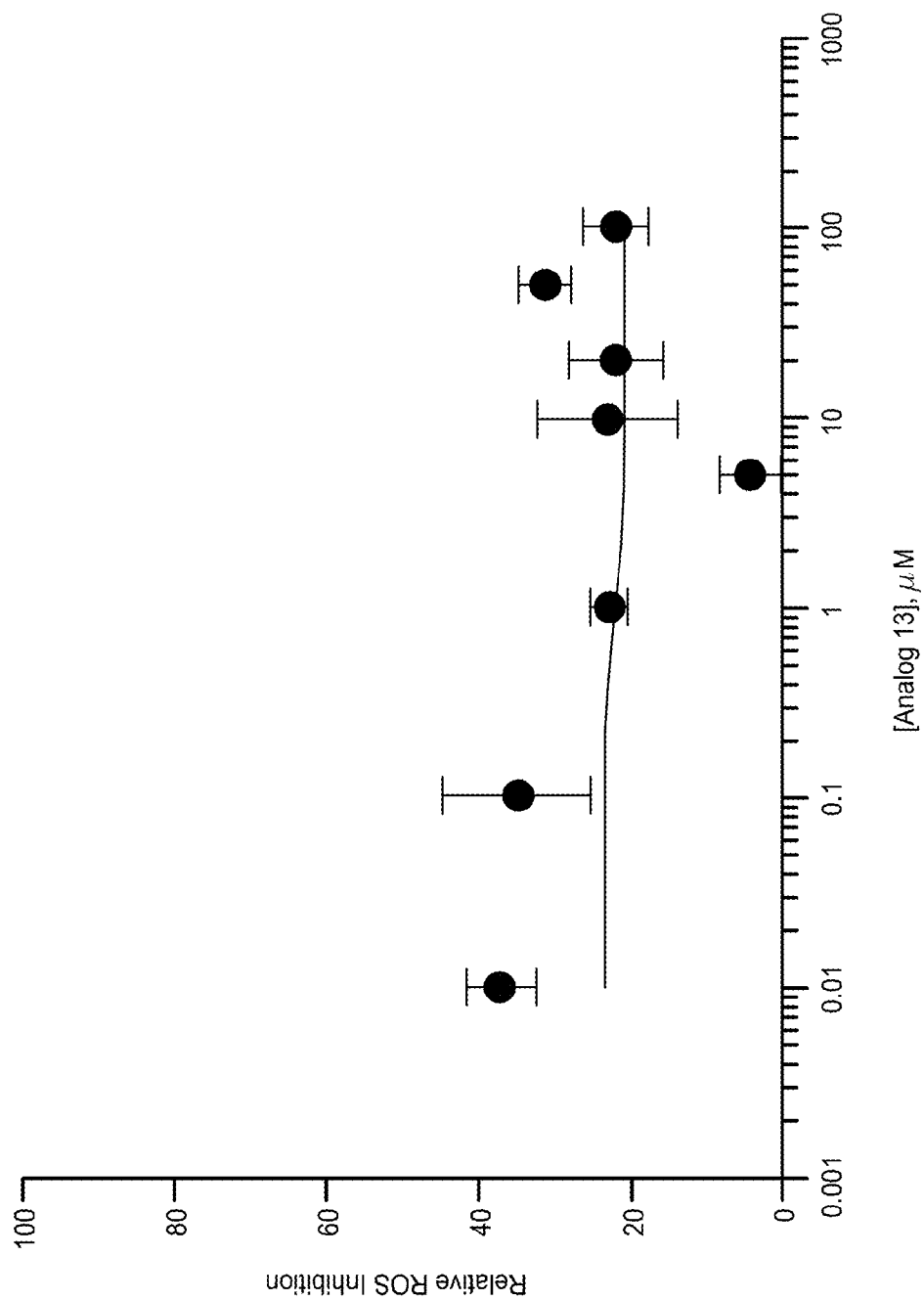

Next, the biochemical binding activity of Phox-I2 to $p67^{phox}$ protein was confirmed with a titration series of Phox-I2 using microscale thermophoresis (FIG. 3D). Phox-I1, Phox-I2 displayed a high-affinity binding to the $p67^{phox}$ target with an approximate Kd of ~150 nM. Additionally, the dose-dependent potency of Phox-I2 was assessed in dHL-60 cells by the DCFDA assay, which revealed an $IC_{50}$ ~1 µM (FIG. 3E), and in primary human neutrophils by the luminol chemiluminescence assay, yielding an $IC_{50}$ ~6 µM (FIG. 3F). As shown in FIG. 2D, Phox-I1 was able to suppress fMLP induced ROS production in human neutrophils in a dose-dependent 1 manner.

Example 6

Specificity of Phox-I1 and Phox-I2 in Cells

Figure 4A:
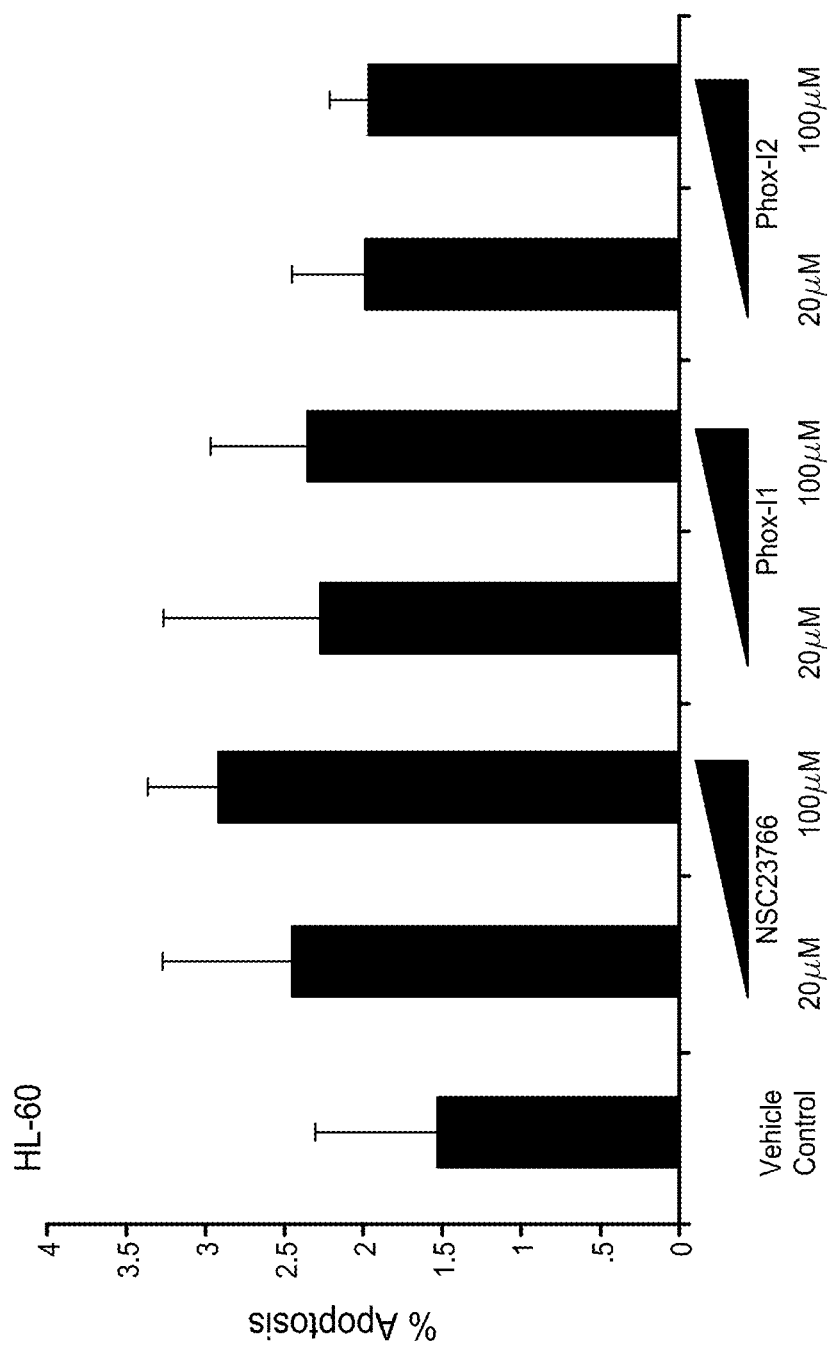

In order to determine potency and cytotoxicity of Phox-I1 and Phox-I2, the levels of apoptosis were assessed in undifferentiated HL-60 cells treated with 20 or 100 µM Phox-I1, Phox-I2, or NSC23766 by FACS analysis for Annexin V (FIG. 4A). There was no detectable effect on cell apoptosis by NSC23766, Phox-I1, or Phox-I2 at either concentration as compared to the untreated control, indicating that these compounds have minimal cytotoxicity in the dosage range of maximal ROS inhibition.

Figure 4B:
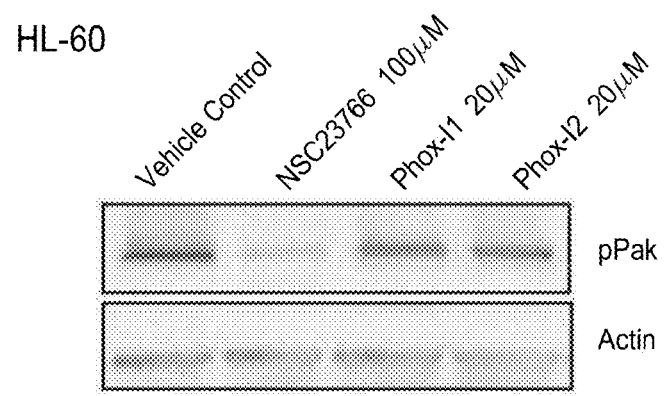

To analyze the biochemical specificity of these lead inhibitors on the effector pathways of active Rac1, undifferentiated HL-60 cells were treated with Phox-I1, Phox-I2, or NSC23766 for 18 hr. Immunoblot of the cell lysates was performed to probe the activity of Pak, a Rac effector other than $p67^{phox}$ (FIG. 4B). The phosphorylated Pak levels were abrogated by treatment with the Rac inhibitor NSC23766 but not Phox-I1 or Phox-I2, suggesting that Phox-I1 and Phox-I2 compounds are specific for the $p67^{phox}$ signaling arm of Rac-GTP, as opposed to Rac-GTP signaling in general, as is evidenced by NSC23766 treatment.

Another method of addressing Rac-signaling specificity in neutrophils is by monitoring their ability to polarize actin to the leading edge upon fMLP stimulation. Neither Phox-I1, Phox-I2, nor an analog 13 (all at 10 µM), were able to block the Rac-mediated dynamic process of F-actin polarization to the leading edge of primary murine neutrophils as observed by F-actin immunofluorescence imaging (FIG. 4C, left panel). F-actin polarization was evident in about 80% of each treatment group of cells as in the control, untreated cells (FIG. 4C, right panel). In contrast, Nocodazole (200 nM), a microtubule disrupting agent that was used as a positive control for disruption of the cytoskeleton, treated cells showed drastic reduction of polarized cells from 80% to ~20%. These data demonstrate that the Phox-I1 and Phox-I2 $p67^{phox}$ targeting agents do not affect Rac-mediated F-actin assembly.

Figure 6:
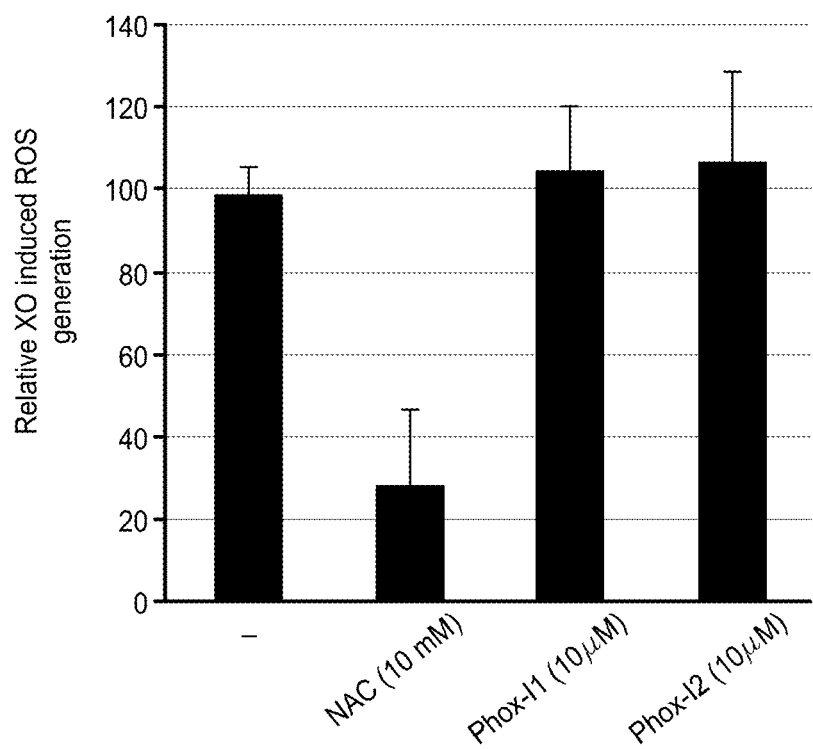
FIG. 6 is a graph showing that Phox-I1 and Phox-I2 do not affect xanthine oxidase mediated ROS production.

To test if the inhibitors are specific for the NOX2 enzyme, a xanthine/xanthine oxidase assay was performed. Specifically, vehicle, NAC (10 mM), Phox-I2 (10 µM) or Phox-I2 (10 µM) was added to the assay, and incubated for 30 min at room temperature. The results were calculated by taking superoxide production in the absence of inhibitors as 100 and value obtained with NAC, Phox-I1 or Phox-I2 was expressed as relative %. The data shown in FIG. 6 represent those from three separate experiments. These data demonstrate that Phox-I1 or Phox-I2 does not affect xanthine oxidase-mediated ROS production.

Figure 4D:
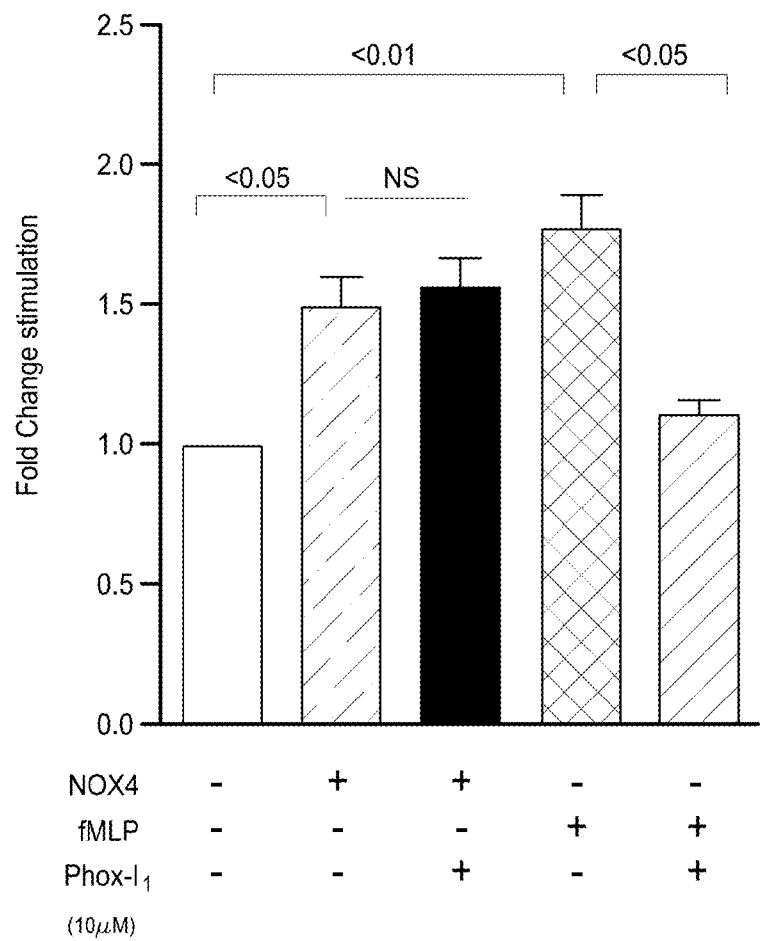
Figure 4E:
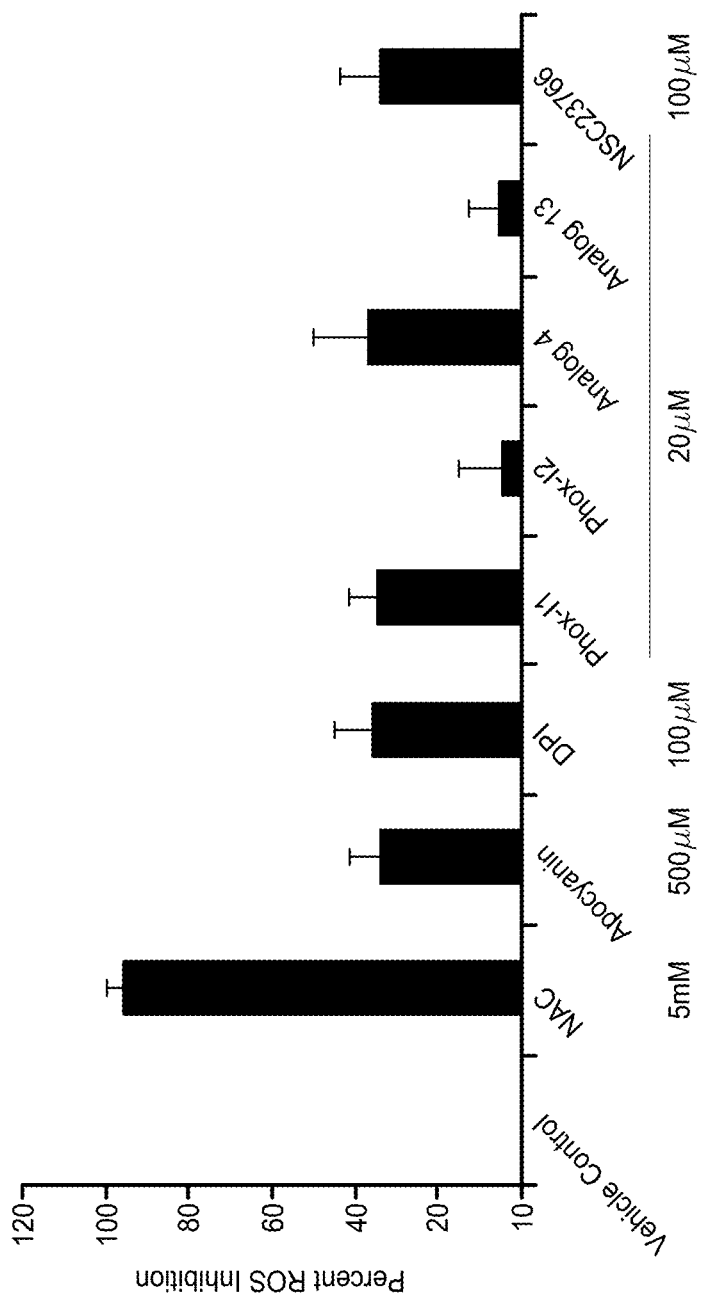

Phox-I1 was then applied to primary murine neutrophils expressing the constitutively active NOX4. As shown in FIG. 4D, expression of NOX4 cDNA in neutrophils by nucleofection resulted in an elevated ROS production that is unresponsive to Phox-I1 treatment, in contrast to the fMLP-induced NOX2-mediated ROS response as assayed using a luminescence assay of L012 in the presence of HRP. To further rule out that Phox-I1 and Phox-12 may simply act as scavengers of ROS, dHL-60 cells were pre-stimulated with fMLP for 30 min prior to treatment with Phox-I1 or Phox-I2. Unlike the ROS scavenger NAC, Phox-I1 and Phox-I2 do not affect the levels of superoxide that have already been produced, similarly to apocyanin, DPI, and NSC23766 (FIG. 4E). Therefore, these $p67^{phox}$ inhibitors do not display antioxidant activity and are specific, consistent with their lack of inhibitory effect on glucose oxidase-induced ROS, as shown previously in FIG. 2E.

Figure 4F:
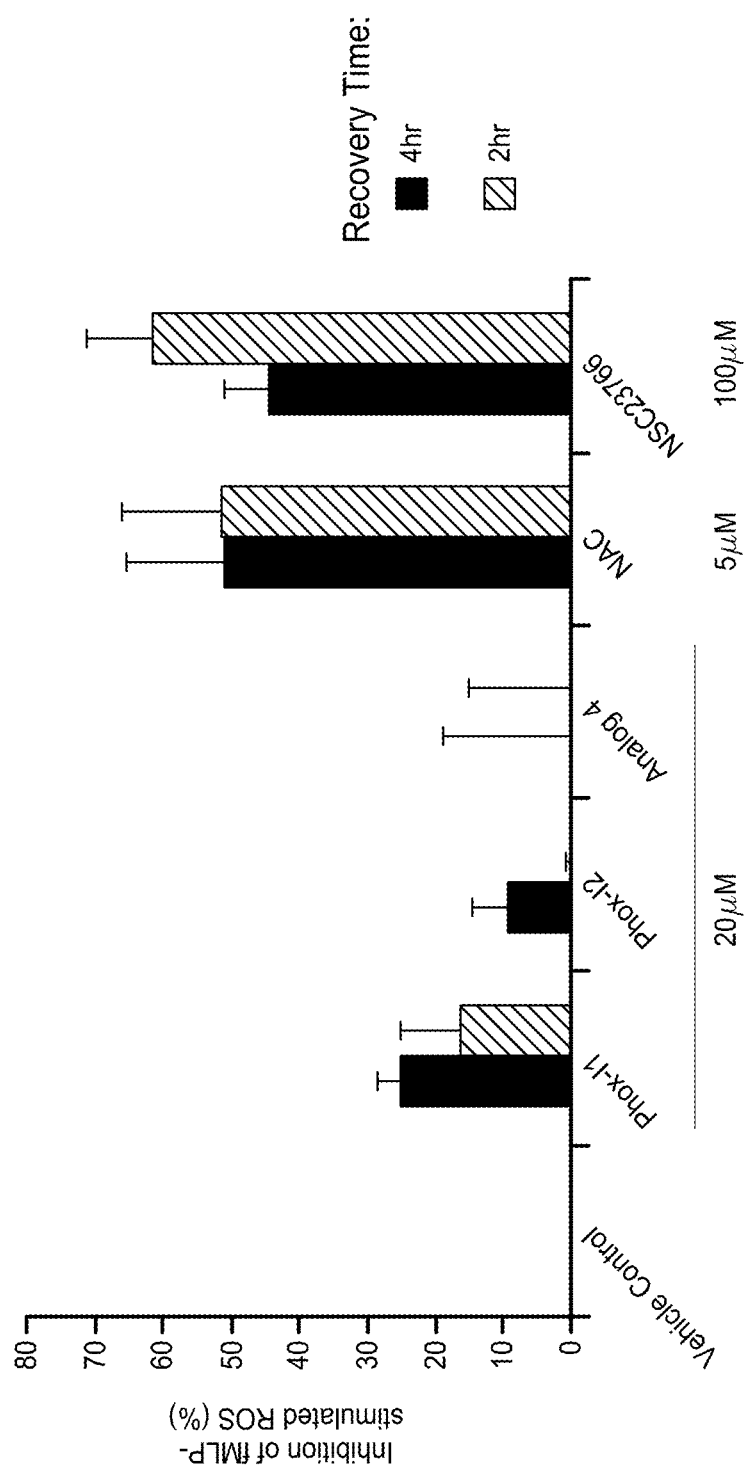

Next, a stability experiment was performed to determine the duration of effectiveness of the compound in suppressing neutrophils. To analyze the relative affinities of these compounds for the $p67^{phox}$ target in cells, DCFDA ROS production assays were performed in dHL-60 cells treated with compound for 2 hr followed by wash and recovery for 4 hr or 2 hr in normal media prior to ROS production analysis. Although Phox-I1 ROS inhibitory activity was still evident 4 hr or 2 hr after washing the cells, Phox-I2 and analog 4 did not display effective ROS inhibition following removal of the compounds at the dosage tested (FIG. 4F). In comparison, the tested dosages of NAC and NSC23766 both retained the ability to inhibit ROS production following a wash of the cells.

Figure 4G:
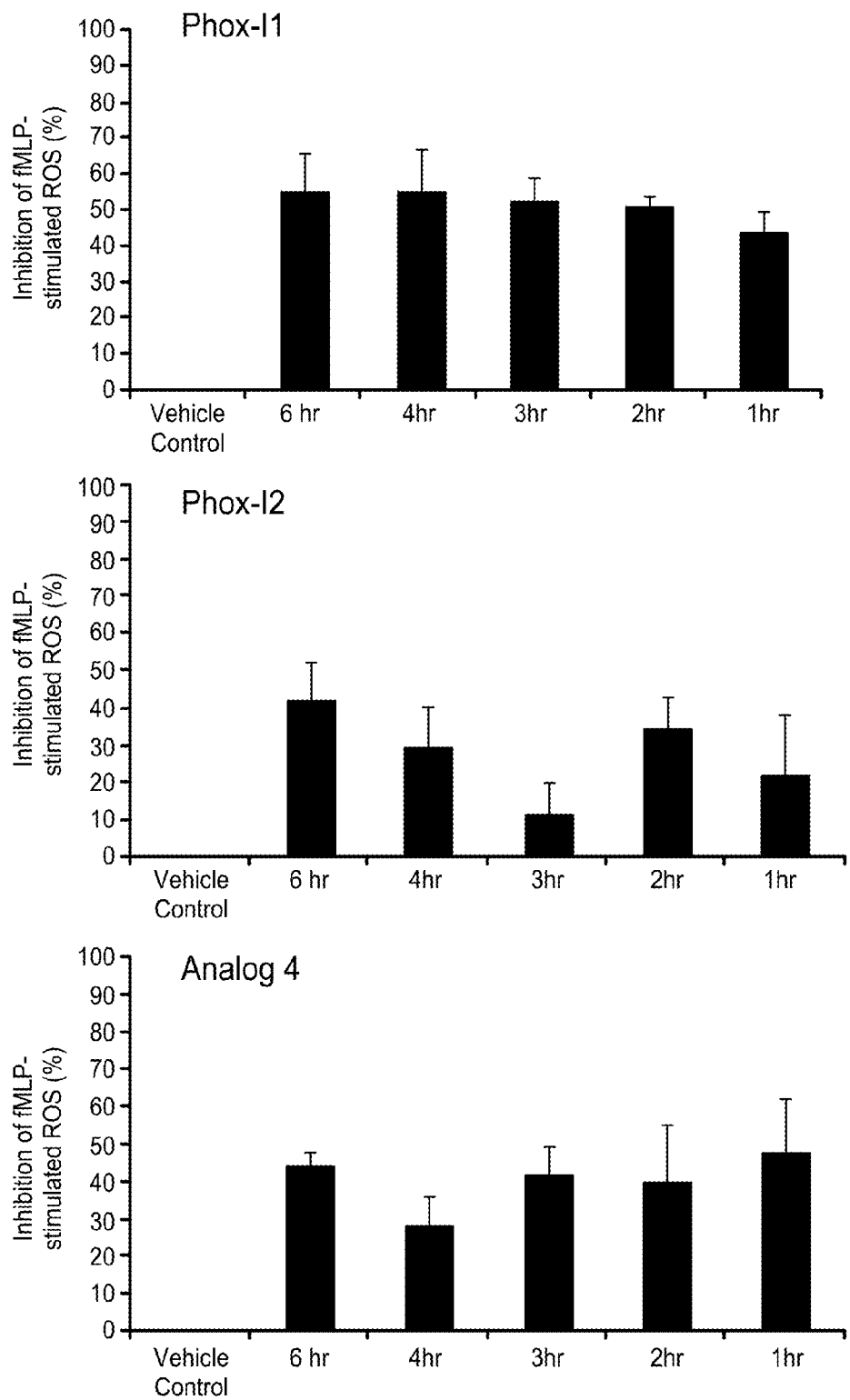

To assess the relative stability of these compounds in culture over time, DCFDA ROS assays were performed in dHL-60 cells following the indicated time of exposure to the compound. None of the compounds were effective at inhibiting ROS production after 18 hr exposure in culture. Phox-I1 seemed to be the most stable in culture over time, displaying no significant change in efficacy in a 6 hr treatment window, whereas Phox-I2 and analog 4 retained some efficacies over 6 hr of treatment with more varied capacity to inhibit ROS (FIG. 4G). These data demonstrate that Phox-I1 and its derivatives display high biochemical and cellular activities in culture with a turnover time of >2-4 hr, indicating that their inhibitory effect is not short-lived, and a continuous supply can achieve maximum effectiveness in overnight culture conditions.

Example 7

Structure-Activity Relationship Analysis of Phox-I2

Figure 5A:
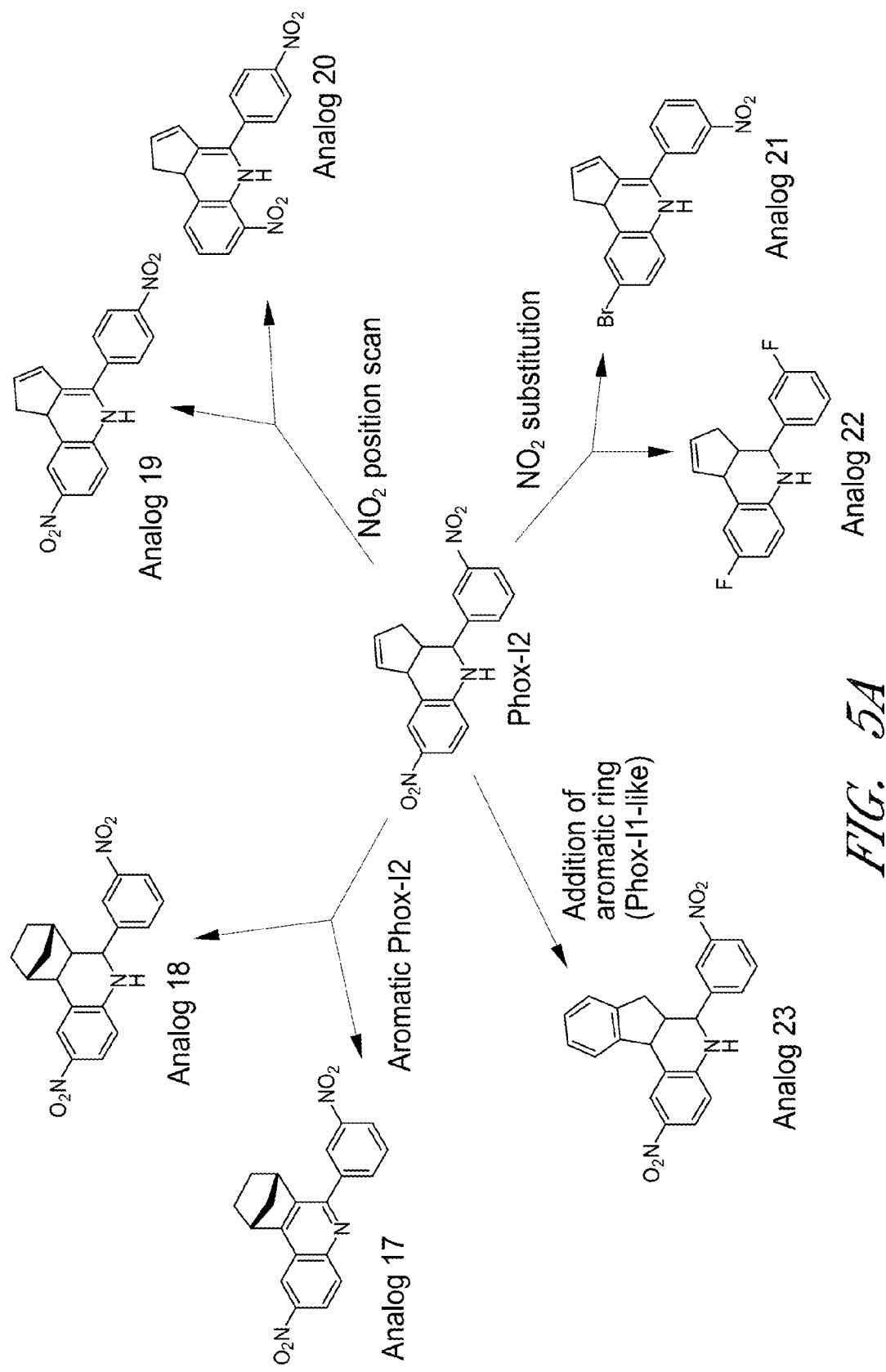
FIGS. 5A-C set forth medicinal chemistry variation of Phox-I2. (A) Compounds with similar structures to Phox-I2 were synthesized and broken down into 4 different categories; 1. NO2 position scan, 2. NO2 substitution, 3. Addition of an aromatic ring (rendering it similar to Phox1), 4. Aromatic Phox2. (B) DCFDA FACS analysis was performed using differentiated HL-60 cells treated for 2 hours with compounds from A prior to stimulation with fMLP. (C) Freshly isolated primary murine neutrophils were stimulated with fMLP to initiate ROS production, cells were then treated with DMSO control, DPI, Phox-I2, Analogs 20, 21, 22, 23. A Nitroblue tetrazolium assay was performed and imaged in order to quantitate superoxide inhibition. Non-fMLP treated ROS levels were subtracted prior to normalization to vehicle control treated sample.
Figure 5B:
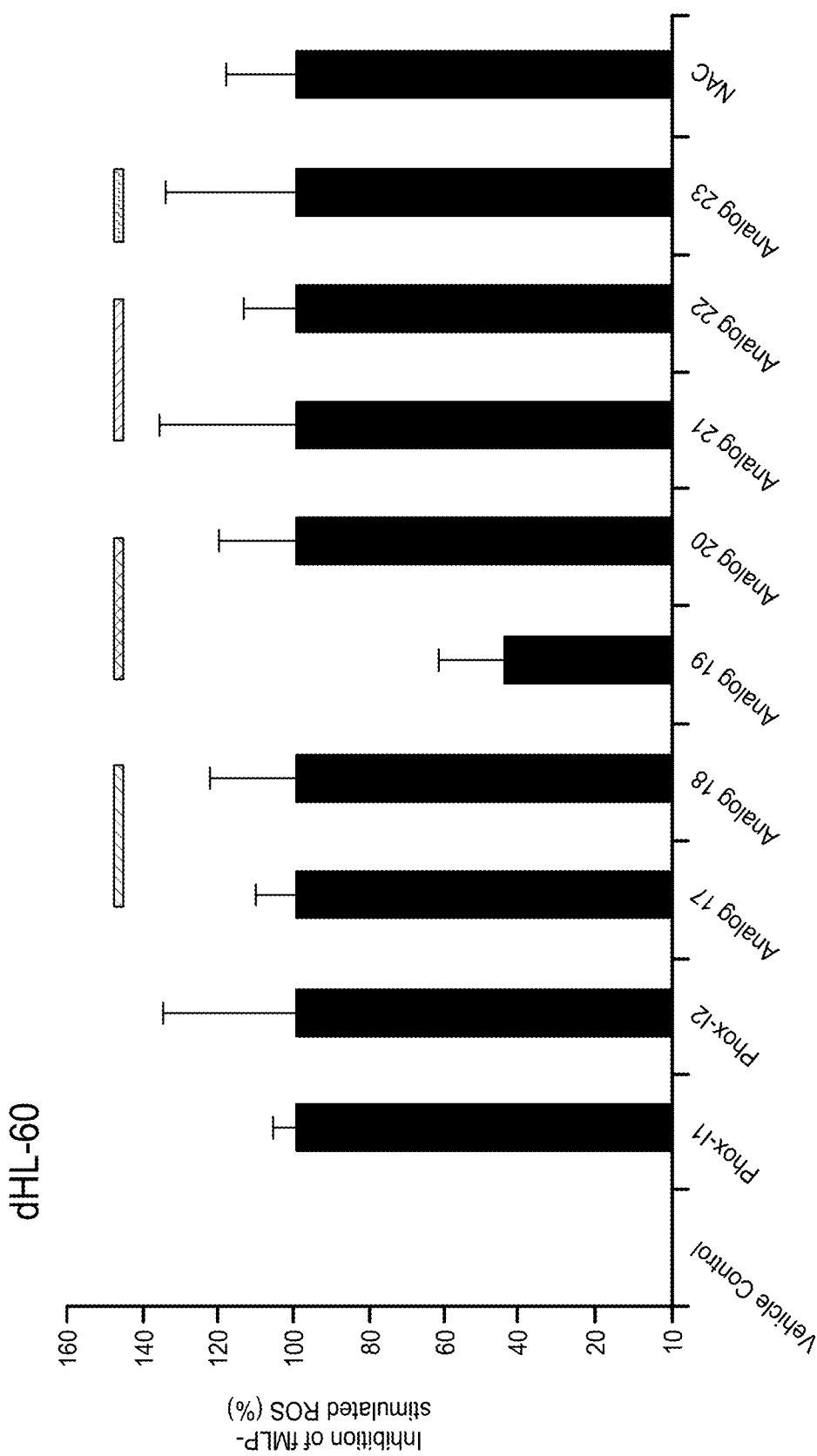

To further define the structure-activity relationship of Phox-I2, medicinal chemistry synthesis of analogs of Phox- I2 was performed to rationalize the key components of the structure for cellular activity. Compounds with similar structures to Phox-I2 through replacement of each nitro group, or addition of an extra aromatic ring to make the compound more "Phox-I1 like," were synthesized. Specifically, based on the Phox-I2 structure, seven compounds of four different categories, as shown in FIG. 5A, were produced. When the ROS inhibitory activities of these compounds were tested by DCFDA FACS analysis in differentiated HL-60 cells, all compounds displayed activity (FIG. 5B).

Figure 5C:
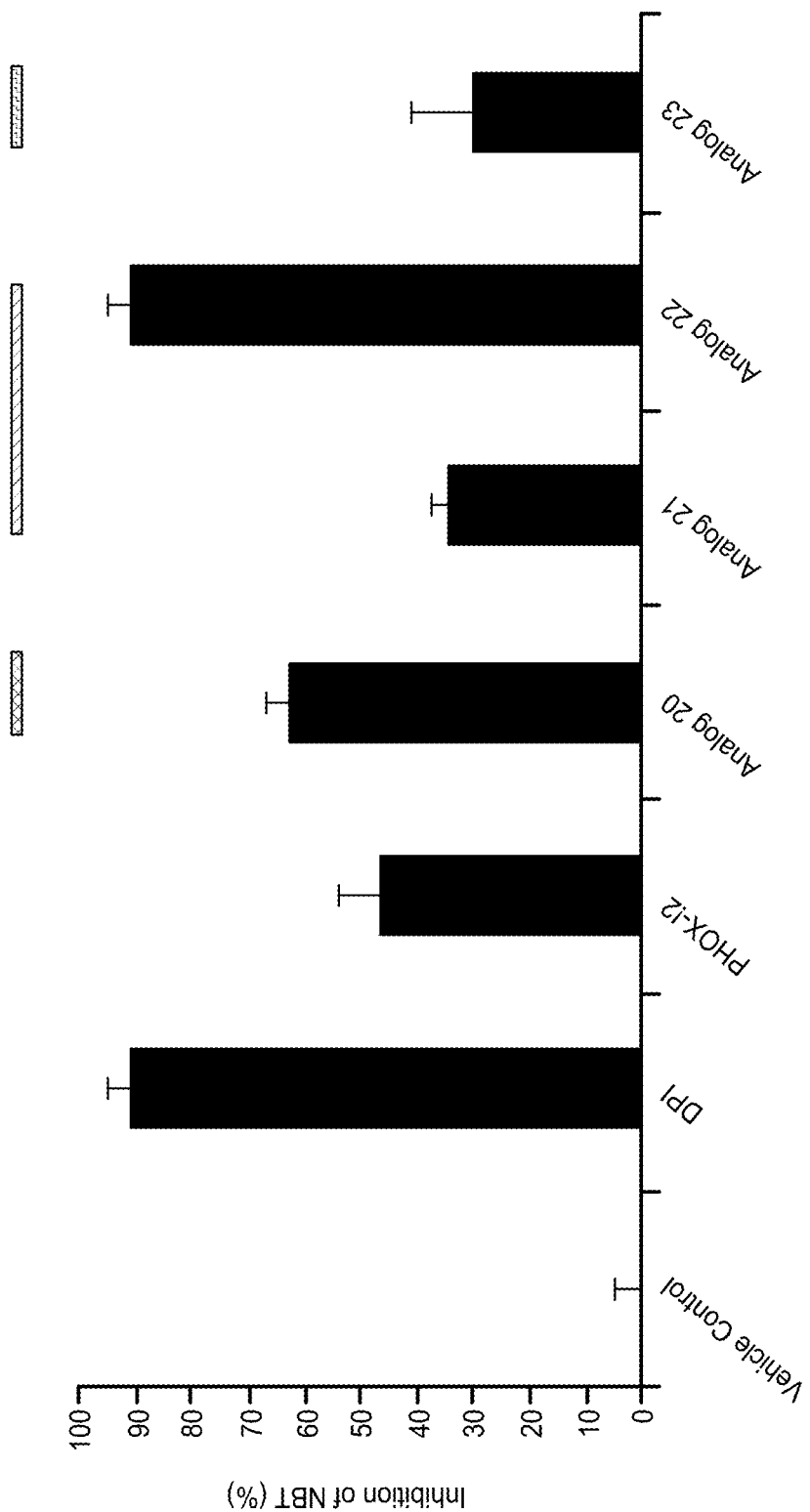

Thus, it is possible to replace the nitro group and retain activity (as shown by analog 22, also referred to herein as compound 100). To confirm this, the NBT assay was performed in primary murine neutrophils where many of the analogs displayed partial activity, with analog 22 (fluorine groups replacing the outermost nitro groups) exhibiting profound superoxide inhibition (FIG. 5C). These studies further define SAR of Phox-I2 structure.

Example 8

Cell-Free Superoxide Production Assays

In order to complement the in silico and cellular results, Phox-I1 and Phox-I2 were tested in cell-free superoxide production assays. Phox-I2 was added to p67 phox (50 nM) in a total volume of 200 µl, and incubated for 30 min at room temperature. A mixture of solubilized macrophage membrane (5 nM cytochrome b 558 heme), p47 phox (50 nM), and Rac1 GMPPNP (nonprenylated) (50 nm), were added. Lithium dodecyl sulfate (LiDS) was added at 130 µM and incubated for 90 sec at room temperature. NADPH was then added (238 µM) and superoxide production measured. In this system, a turnover of 58.88 mol superoxide/sec/mol cytochrome b558 heme was measured. The results were calculated by taking superoxide production in the absence of Phox-I2 as 100% and values obtained with Phox-I2 were expressed as % inhibition. The mean data represent those from six separate experiments.

Figure 7:
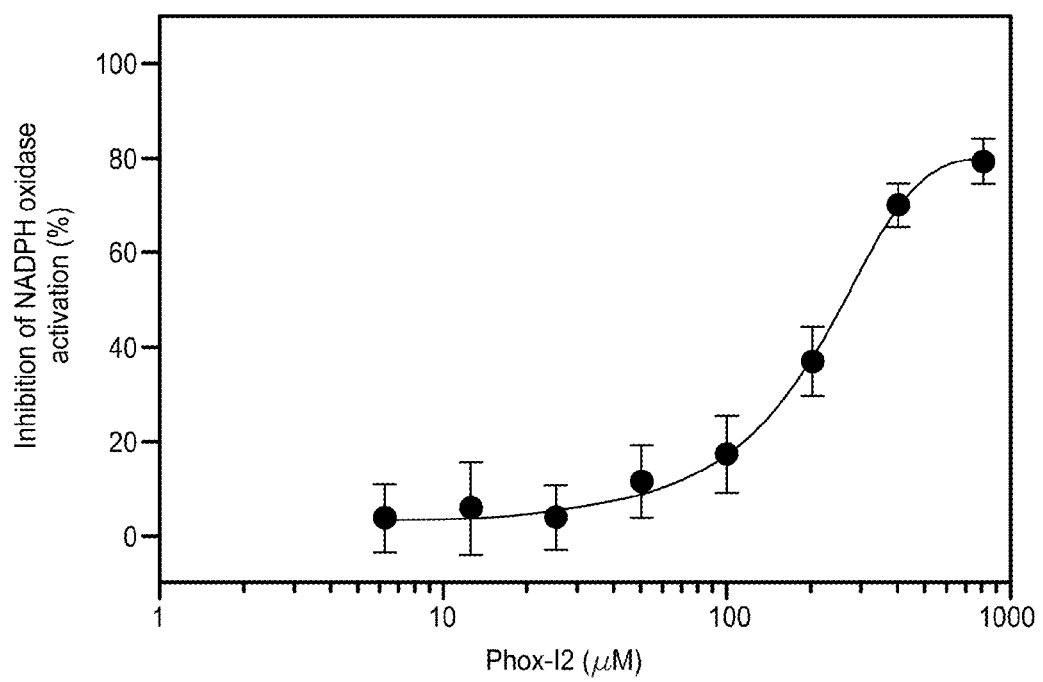
FIG. 7 is a graph showing dose-dependent inhibition of reconstituted NOX2 activity by Phox-I2.

As set forth in FIG. 7, Phox-I2 was able to dose-dependently inhibit Rac1-GMPPNP induced superoxide burst under the reconstitution conditions, consistent with the mode of action proposed for the inhibitor.

Example 9 p67$^{phox}$ Protein Inhibitor Suppresses ROS-Mediated Lipid Oxidation in Vivo and Reduces Lung Inflammation One life-threatening consequence of hemorrhagic shock is acute lung injury (ALI), which is associated with infiltration of neutrophils and release of ROS. A model of LPS-induced ALI was used in mice to test efficacy of the difluoro compound 100 in vivo.

Figure 8A:
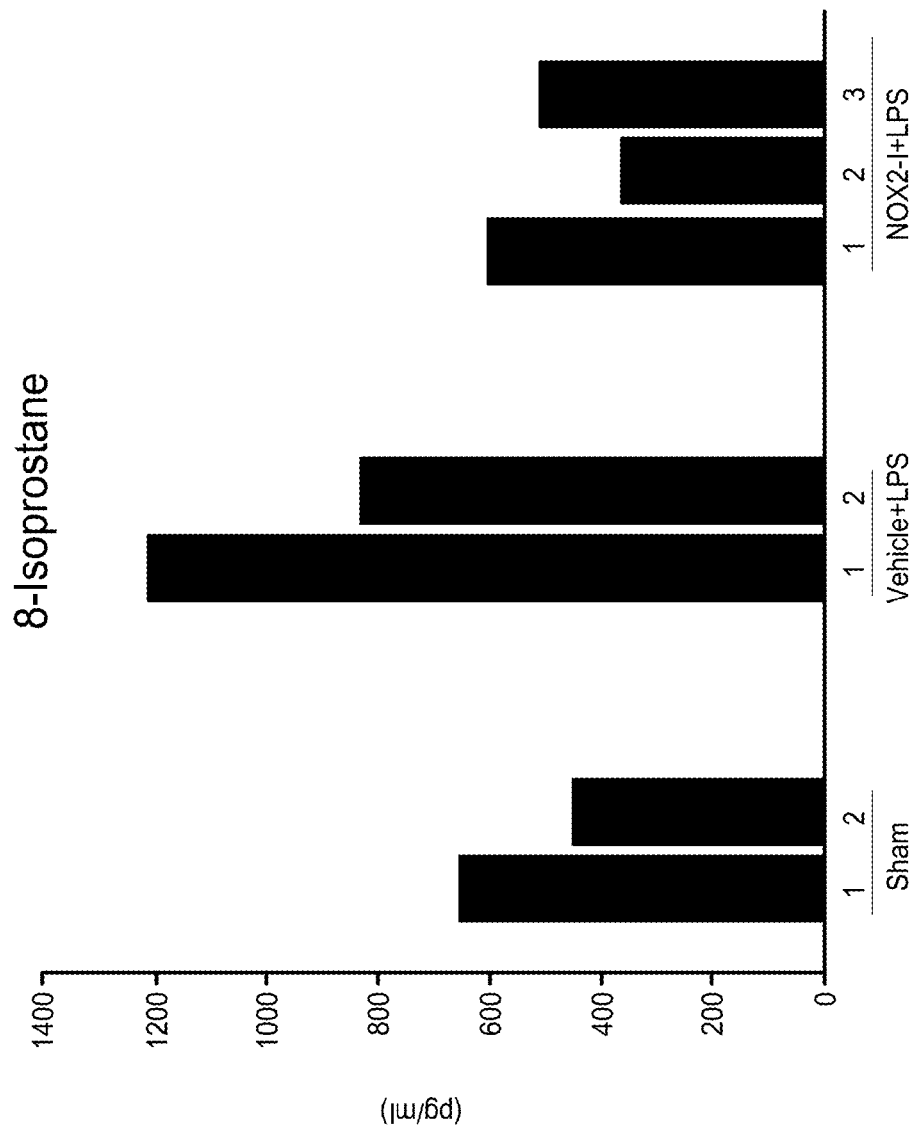
FIG. 8. Treatment with compound 100 suppresses lipid oxidation in lung tissues. Mice were challenged with LPS or vehicle via intratracheal administration and treated or not with compound 100 (indicated as "NOX2-I"; 5 mg/kg, 3 injections every 8 hours). (A) Isoprostane, as an indication of ROS production, was measured in lung homogenates 24 hours following LPS challenge by ELISA. (B) Lung histology was performed 24 hours after LPS challenge. (n=3 mice per group). Representative images of histology are shown.

Mice (N=3 per group) were treated with LPS (100 ng in 80 µl PBS) or PBS (vehicle) employing oral-tracheal intubation. Following challenge, the mice were injected i.p. with 5 mg/kg of compound 100, every 8 hours. The relative level of ROS release in the lungs upon LPS challenge was assessed by measuring 8-isoprostane by ELISA in lung tissue homogenates. Isoprostanes are a family of eicosanoids produced by the oxidation of tissue phospholipids by oxygen radicals. The amount of 8-isoprostane generated is thus an indication of ROS production. As shown in FIG. 8A, at 24 hours, LPS-challenged mice had higher levels of 8-isoprostane relative to control animals. This was blunted by treatment with compound 100.

Example 10 p67$^{phox}$ Protein Inhibitor Reduces Lung Inflammation In Vivo

Figure 8B:
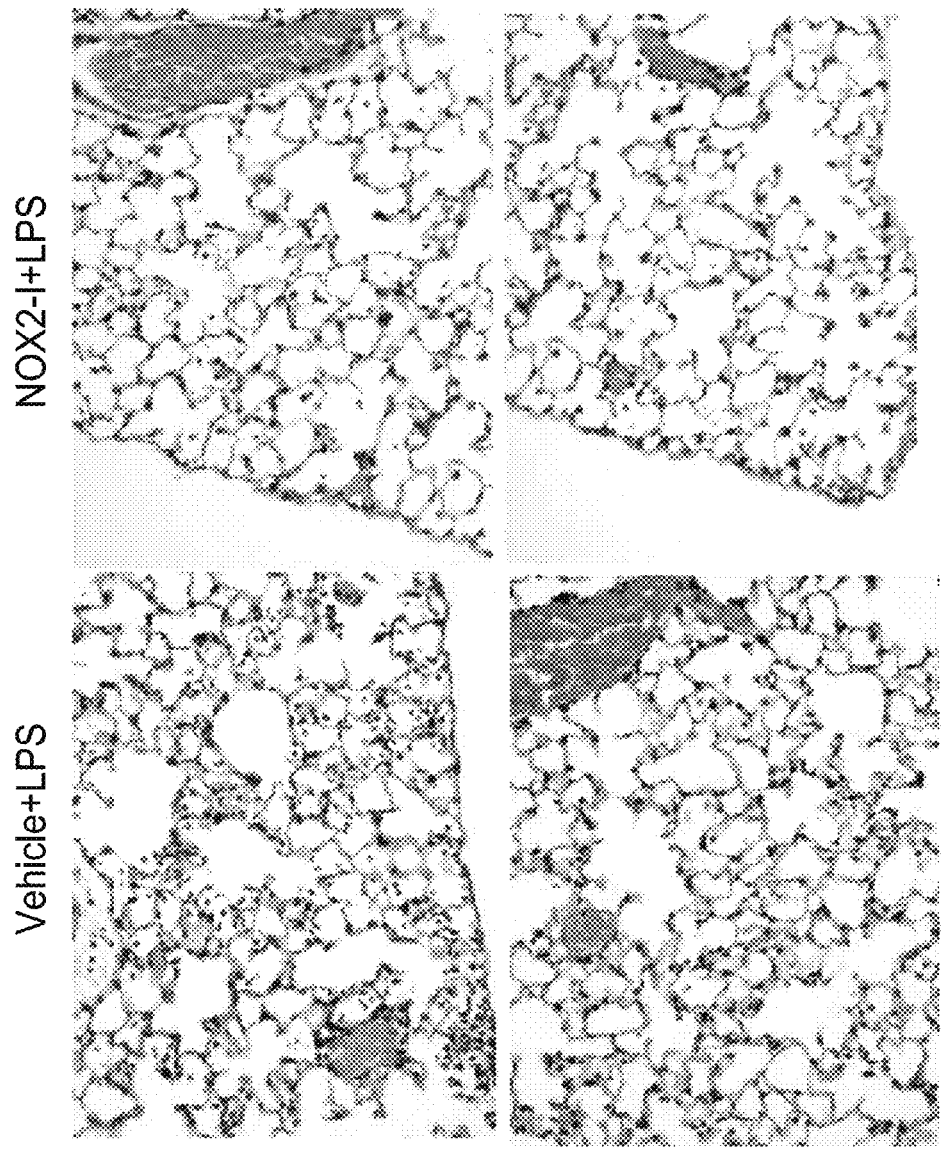

The LPS challenge described above in Example 8 also induced lung neutrophil infiltration, increased thickness of the alveoli walls and disruption of lung architecture at 24 hours of LPS challenge, as shown in FIG. 8B. As shown in FIG. 8B, these pathological findings were attenuated by treatment with compound 100.

Example 11

Effect of Compounds on Neutrophil ROS Production

Figure 9:
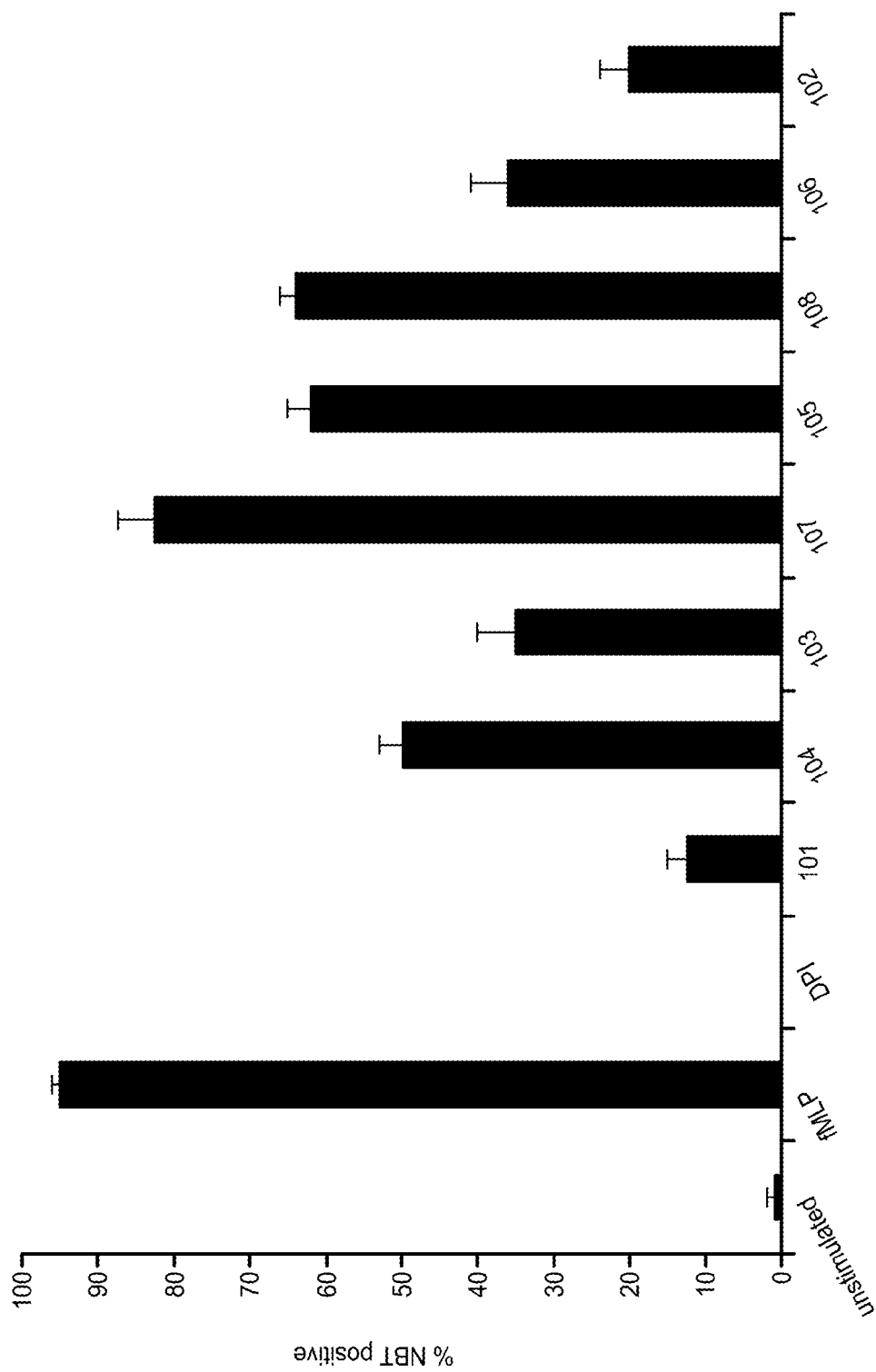
FIG. 9 sets forth experimental results demonstrating that compounds 101-108 have ROS inhibitory activity. Freshly isolated primary murine neutrophils were unstimulated or stimulated with fMLP to initiate ROS production, cells with stimulated primary murine neutrophil cells were either a control, or each treated with a compound where each of compound 101-108 was added to a separate cell and a Nitroblue tetrazolium (NBT) assay was performed. ROS production was quantified in the cells.

Compounds 101-109 shown in Table 4 were synthesized and tested using the NBT assay. The NBT assay was performed in primary murine neutrophils to measure ROS neutrophil production. FIG. 9 shows a graph of the analysis of several of the compounds assayed by a NBT readout and shows the inhibitory activities of the compounds. The percent of NBT positive cells is shown in FIG. 9 indicating positive ROS production. N-Formyl-methionyl-leucyl-phenylalanine (fMLP) a potent stimulator of ROS production; diphenyleneiodonium (DPI) a potent inhibitor of ROS production were used as controls. Each compound was used at 10 µM. The data suggest that compounds 101, 103, 106, and 102 show the highest level of ROS inhibition. Compound 109 shown in Table 4 was toxic to neutrophils.

Figure 10:
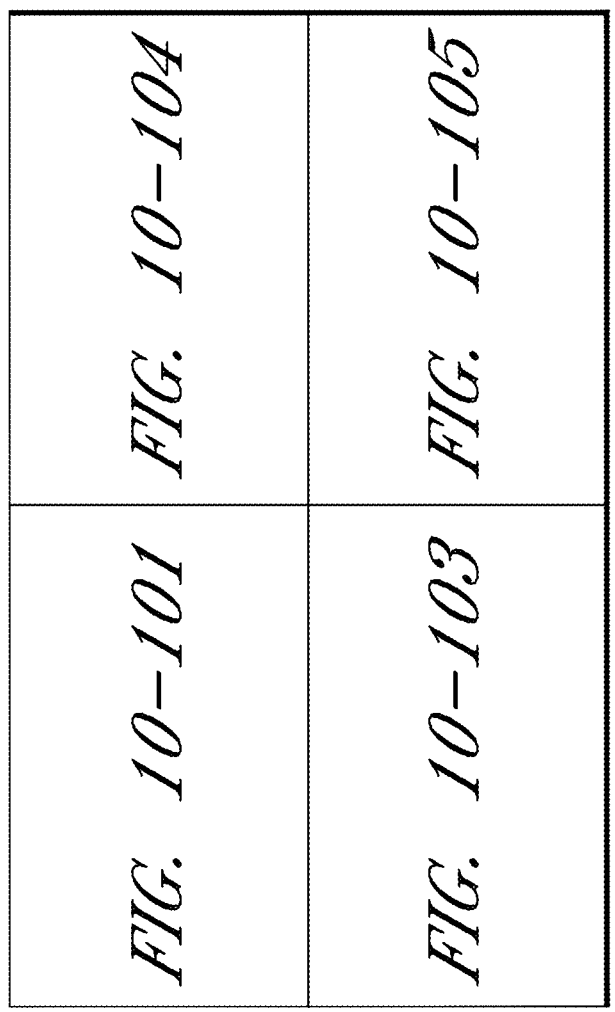
FIG. 10 sets forth experimental results demonstrating that compounds 101, 104, 103, and 105 have ROS inhibitory activity. The histograms show the inhibitory activities of the compounds, assayed by a NBT readout. The percent of NBT positive cells is shown, indicating positive ROS production. fMLP and DPI were used as positive and negative controls. Each compound was used at 0.1 to 10 μM.
Figures 10, 101:
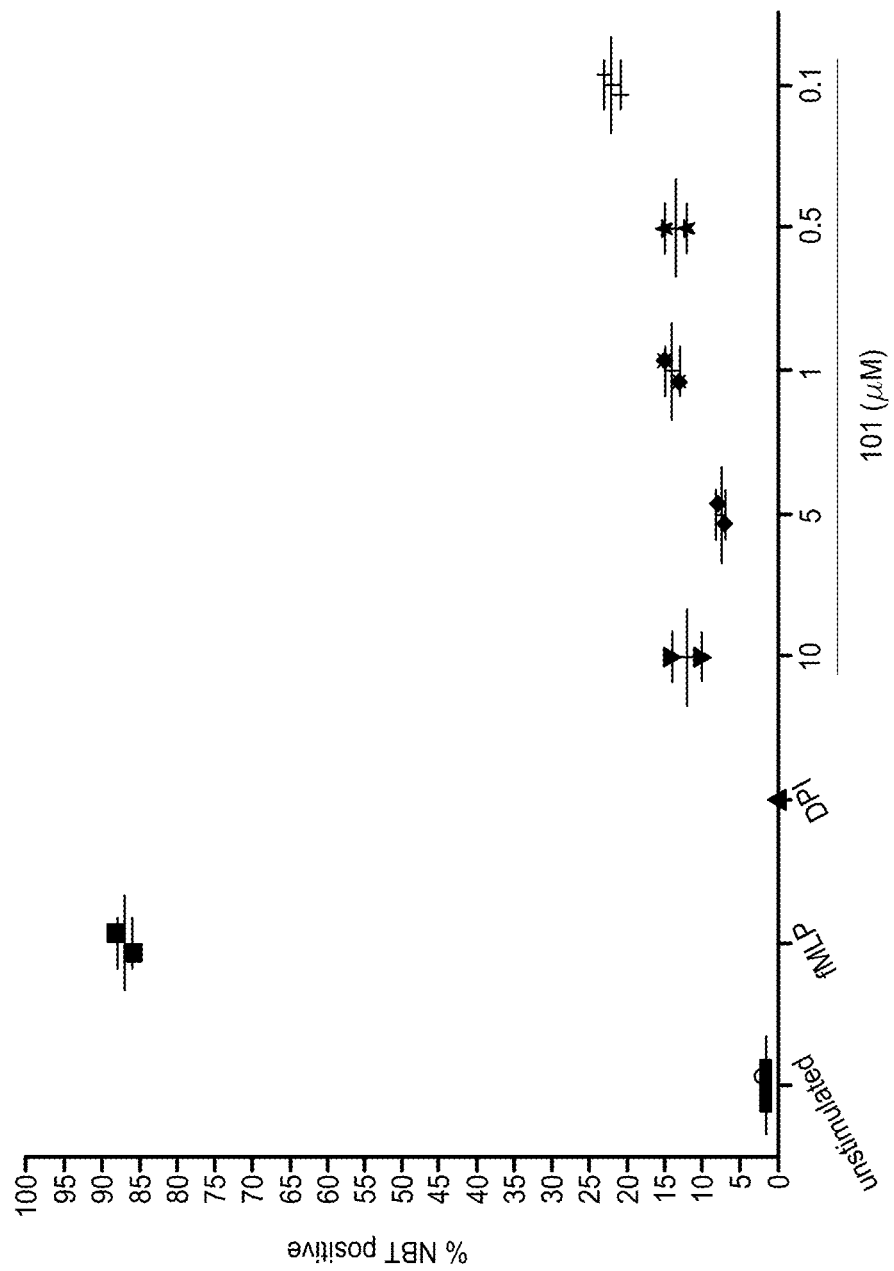
Figures 10, 103:
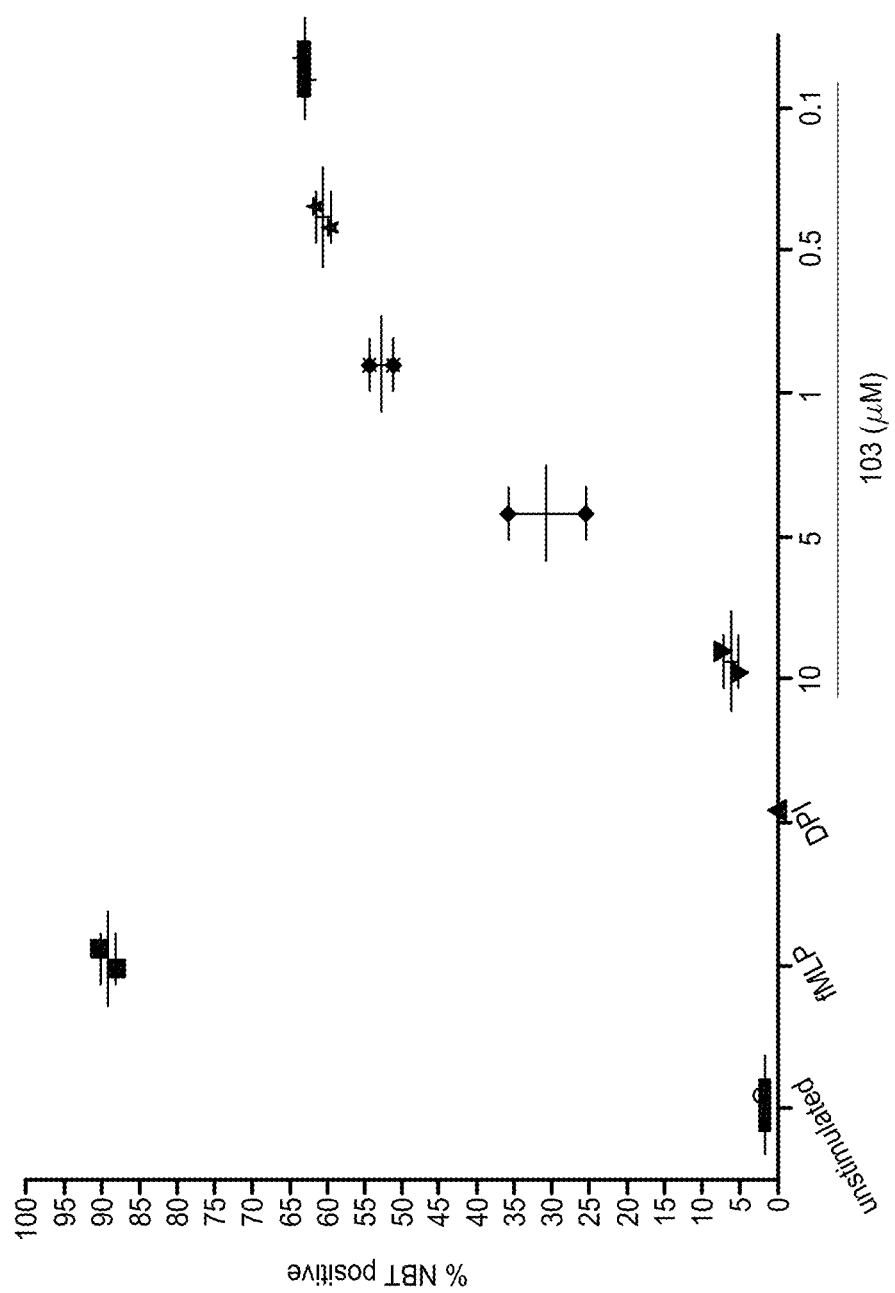
Figures 10, 104:
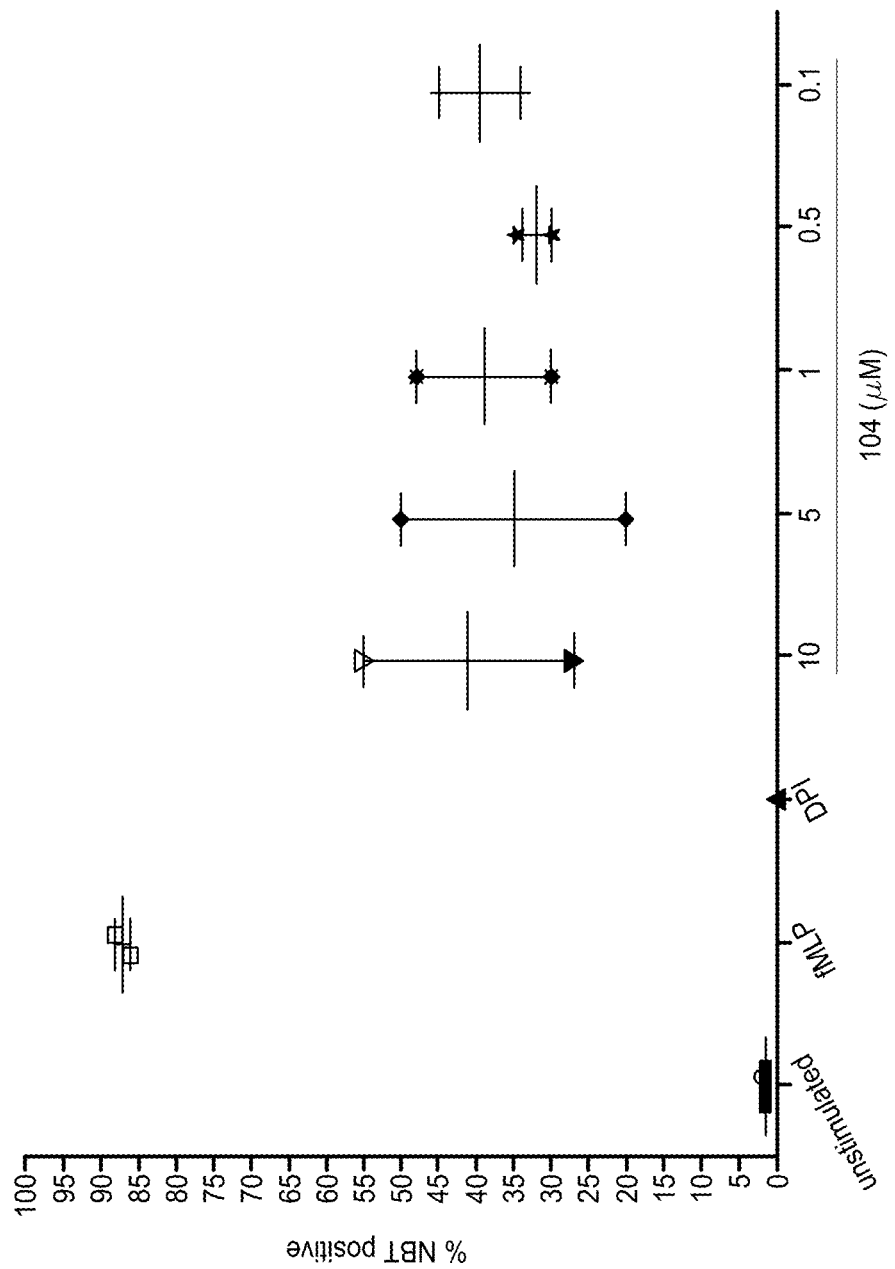
Figures 10, 105:
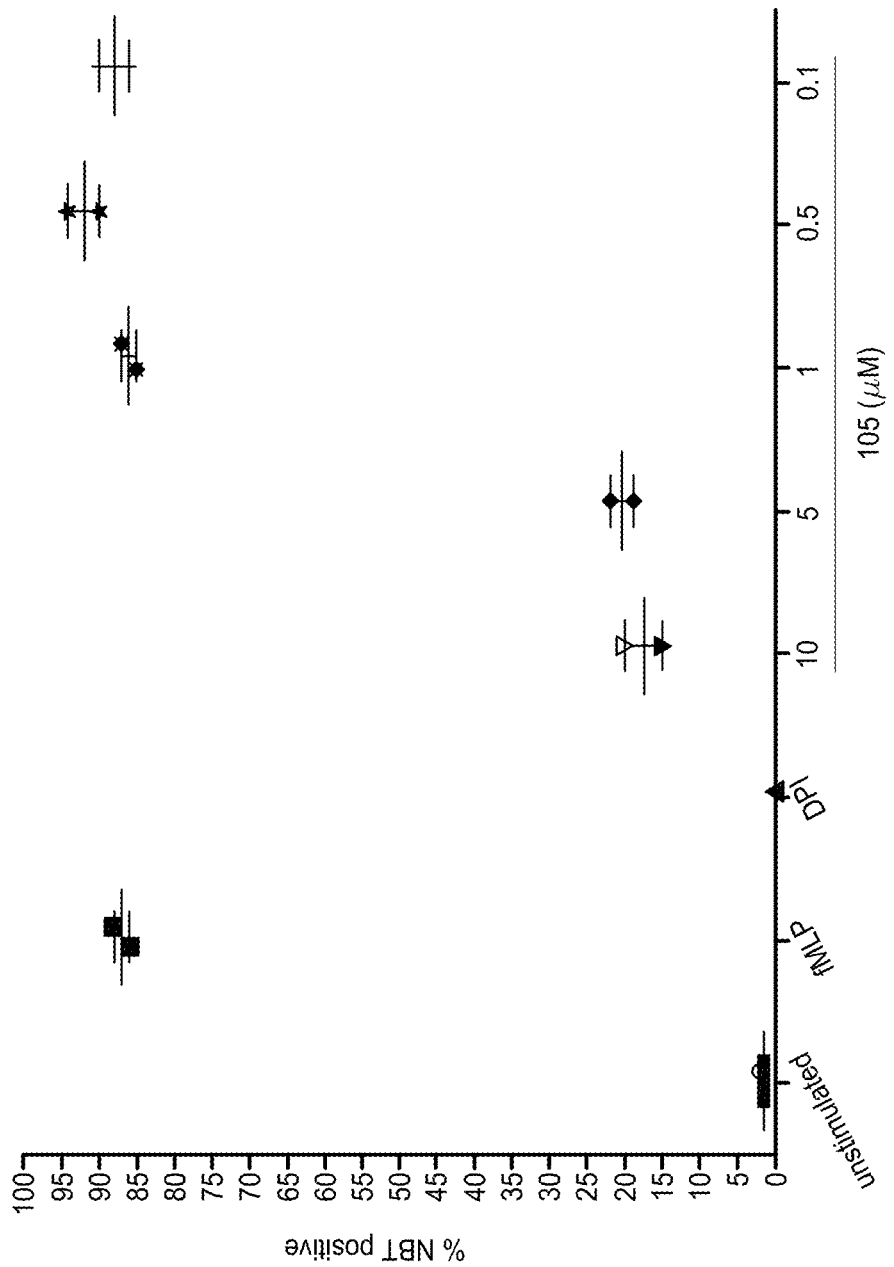

A dose response study (0.1 to 10 µM) of compounds 101, 104, 103, and 105 selected in murine neutrophils are shown in FIG. 10. The NBT test was used to measure ROS neutrophil production. Compound 101 appears the most potent ROS inhibitor.

TABLE 4

| Compound Number | Structure |
| --- | --- |
| 109 | 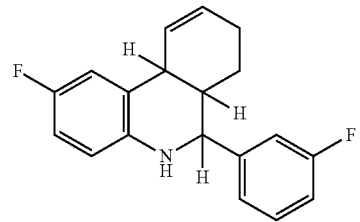 [SMILES: Fc1cccc(C2Nc3ccc(F)cc3C3C=CCCC32)c1] |

While the present embodiments have been described in connection with what is presently considered to be practical exemplary embodiments, it is to be understood that the invention is not limited to the disclosed embodiments and is intended to cover various modifications and equivalent arrangements included within the spirit and scope of the appended claims.

What is claimed is:

1. A method of treating neutrophil infiltration, hemorrhagic shock or lung inflammation in an individual comprising administering to the individual an effective amount of a compound having the structure of Formula I:

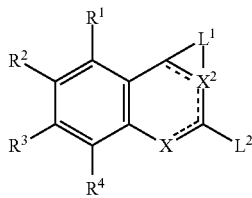

I or a pharmaceutically acceptable salt thereof,
wherein:
L$^1$ is selected from the group consisting of —C=C—C—; —O—C—C—; —O—C—C—C—; or the bridge structure shown below

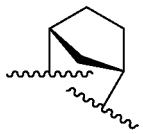 [SMILES: *[C@@H]1CC[C@H](*)C1]

each optionally substituted with one or more R$^{1A}$;
L$^2$ is aryl or heteroaryl each optionally substituted with one or more with one or more R$^{2A}$;
each R$^{1A}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, (R$^{1BB}$R$^{1CC}$N)alkyl, (C$_1$-C$_6$)alkyl optionally substituted with up to 5 fluoro, and (C$_1$-C$_6$)alkoxy optionally substituted with up to 5 fluoro,
said aryl, heteroaryl, heterocyclyl, arylalkyl, heteroarylalkyl, heterocyclylalkyl, cycloalkyl, cycloalkenyl, and (cyclolalkyl)alkyl in the definition of R$^{1A}$ are each optionally substituted with one or more R$^{1AA}$;
each R$^{1AA}$ is independently selected from the group consisting of hydroxy, halo, cyano, nitro, aryl, heteroaryl, heterocyclyl, arylalkyl, heteroarylalkyl, heterocyclylalkyl, cycloalkyl, cycloalkenyl, (cyclolalkyl)alkyl, (C$_1$-C$_6$)alkyl optionally substituted with up to 5 fluoro, and (C$_1$-C$_6$)alkoxy optionally substituted with up to 5 fluoro;
each R$^{2A}$ is independently selected from the group consisting of hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;
R$^1$, R$^2$, R$^3$, and R$^4$ are each independently selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

each NR$^{1B}$R$^{1C}$ is independently selected, wherein R$^{1B}$ and R$^{1C}$ are each independently from the group consisting of hydrogen, C$_{1-6}$alkyl, aryl, arylalkyl, cycloalkyl, (cyclolalkyl)alkyl, (R$^{1BB}$R$^{1CC}$N)alkyl, and (R$^{1BB}$R$^{1CC}$N)C(=O)—;
each R$^{1D}$ is independently selected from the group consisting of hydroxy, aryl, heteroaryl, heterocyclyl, arylalkyl, cycloalkyl, cycloalkenyl, (cyclolalkyl)alkyl, (R$^{1BB}$R$^{1CC}$N)alkyl, (C$_1$-C$_6$)alkyl optionally substituted with up to 5 fluoro, and (C$_1$-C$_6$)alkoxy optionally substituted with up to 5 fluoro;
each R$^{1BB}$R$^{1CC}$N is independently selected, wherein R$^{1BB}$ and R$^{1CC}$ are each independently from the group consisting of hydrogen, C$_{1-6}$alkylOC(=O)—, C$_{1-6}$alkyl, C$_{1-6}$alkylC(=O)—, aryl, arylalkyl, cycloalkyl, and heterocyclyl;
X is N (nitrogen) or NR$^{11}$;
each z is independently 0, 1 or 2;
R$^{11}$ is H (hydrogen) or C$_{1-6}$ alkyl;
X$^2$ is C (carbon), or CR$^{12}$;
R$^{12}$ is H (hydrogen) or C$_{1-6}$ alkyl; and
each dashed line is an optional double bond.

2. The method of claim 1, wherein the compound having the structure of Formula I has the structure of Formula II,

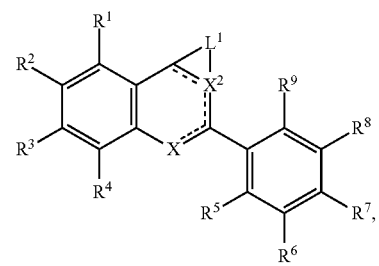

II or a pharmaceutically acceptable salt thereof,
wherein:
R$^5$, R$^6$, R$^7$, R$^8$, and R$^9$ are each independently selected from the group consisting of hydrogen, hydroxy, halo, cyano, nitro, —S(O)$_z$NR$^{1E}$R$^{1F}$, —NHS(O)$_z$NR$^{1E}$R$^{1F}$, —OC(=O)NR$^{1E}$R$^{1F}$, —NHC(=O)NR$^{1E}$R$^{1F}$, —C(=O)NR$^{1E}$R$^{1F}$, —NR$^{1E}$R$^{1F}$, —S(O)$_z$R$^{1G}$, —NHS(O)$_z$R$^{1G}$, —NHC(=O)R$^{1G}$, —OC(=O)R$^{1G}$, —C(=O)R$^{1G}$, —C(=O)OR$^{1G}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;
each NR$^{1E}$R$^{1F}$ is independently selected, wherein R$^{1E}$ and R$^{1F}$ are each independently from the group consisting of hydrogen, C$_{1-6}$alkyl, aryl, arylalkyl, cycloalkyl, (cyclolalkyl)alkyl, (R$^{1EE}$R$^{1FF}$N)alkyl, and (R$^{1EE}$R$^{1FF}$N)C(=O)—;
each R$^{1G}$ is independently selected from the group consisting of hydroxy, aryl, heteroaryl, heterocyclyl, arylalkyl, cycloalkyl, cycloalkenyl, (cyclolalkyl)alkyl, (R$^{1EE}$R$^{1FF}$N)alkyl, (C$_1$-C$_6$)alkyl optionally substituted with up to 5 fluoro, and (C$_1$-C$_6$)alkoxy optionally substituted with up to 5 fluoro; and
each R$^{1EE}$R$^{1FF}$N is independently selected, wherein R$^{1EE}$ and R$^{1FF}$ are each independently from the group consisting of hydrogen, C$_{1-6}$alkylOC(=O)—, C$_{1-6}$alkyl, C$_{1-6}$alkylC(=O)—, aryl, arylalkyl, cycloalkyl, and heterocyclyl.

3. The method of claim 2, wherein the compound having the structure of Formula II has the structure of Formula Ia, Formula Ic, or Formula Id, (Ia)
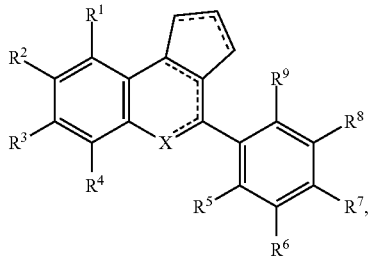

(Ic)
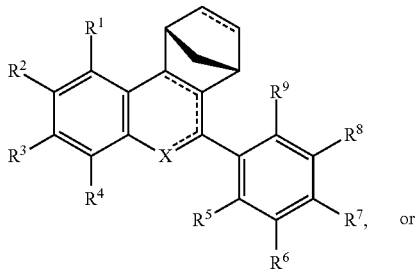

or (Id)
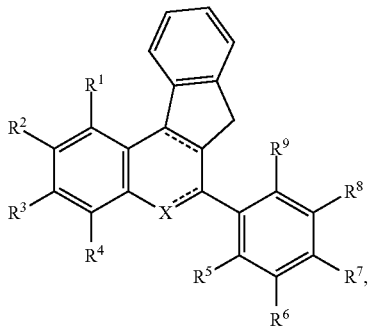

or a pharmaceutically acceptable salt thereof.

4. The method of claim 3, wherein the compound having the structure of Formula Ia has the structure of Formula Iaa, Iab, or Iac, (Iaa)
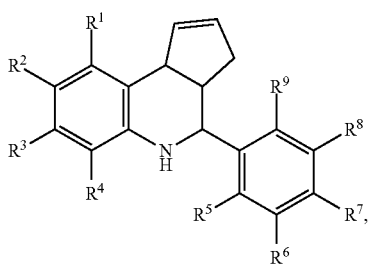

-continued (Iab)
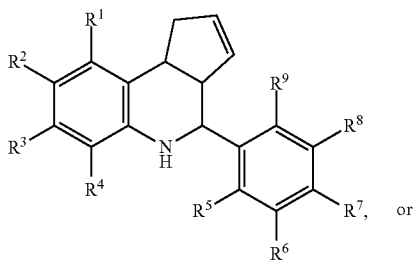

or (Iac)
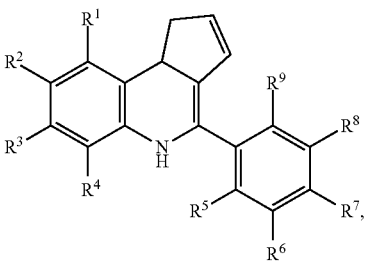

or a pharmaceutically acceptable salt thereof.

5. The method of claim 3, wherein the compound having the structure of Formula Ic has the structure of Formula Ica or Icb, (Ica)
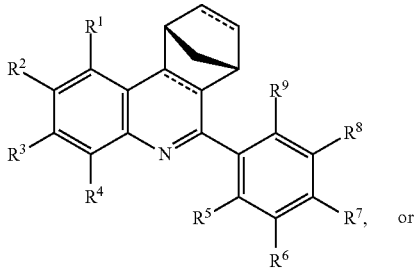

or (Icb)
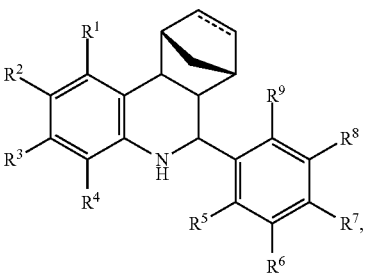

or a pharmaceutically acceptable salt thereof.

6. The method of claim 3, wherein the compound having the structure of Formula Id has the structure of Formula Ida,

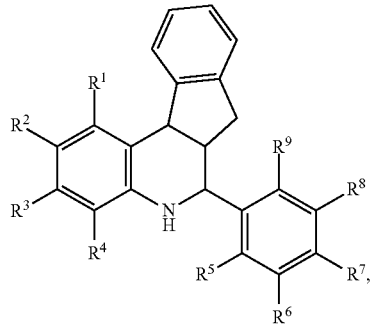

(Ida)

or a pharmaceutically acceptable salt thereof.

7. The method of claim 1, wherein:

$R^1$, $R^2$, $R^3$, and $R^4$ are each independently selected from the group consisting of hydrogen, hydroxy, halo, cyano, nitro, —S(O)$_z$NR$^{1B}$R$^{1C}$, —C(=O)NR$^{1B}$R$^{1C}$, —NR$^{1B}$R$^{1C}$, —NHS(O)$_z$R$^{1D}$, —NHC(=O)R$^{1D}$, —C(=O)R$^{1D}$, —C(=O)OR$^{1D}$, hydroxy(C$_1$-C$_6$)alkyl, (C$_1$-C$_6$)alkyl optionally substituted with up to 5 fluoro, and (C$_1$-C$_6$)alkoxy optionally substituted with up to 5 fluoro;

each NR$^{1B}$R$^{1C}$ is independently selected, wherein R$^{1B}$ and R$^{1C}$ are each independently from the group consisting of hydrogen, and C$_{1-6}$alkyl; and each R$^{1D}$ is independently selected from the group consisting of (C$_1$-C$_6$)alkyl optionally substituted with up to 5 fluoro, and (C$_1$-C$_6$)alkoxy optionally substituted with up to 5 fluoro.

8. The method of claim 2, wherein:

$R^5$, $R^6$, $R^7$, $R^8$, and $R^9$ are each independently selected from the group consisting of hydrogen, halo, nitro, —NR$^{1E}$R$^{1F}$, (C$_1$-C$_6$)alkyl optionally substituted with up to 5 fluoro, and (C$_1$-C$_6$)alkoxy optionally substituted with up to 5 fluoro; and each NR$^{1E}$R$^{1F}$ is independently selected, wherein R$^{1E}$ and R$^{1F}$ are each independently from the group consisting of hydrogen, and C$_{1-6}$alkyl.

9. A pharmaceutical composition comprising a pharmaceutically acceptable excipient, and a compound having the structure of Formula Ica or Icb,

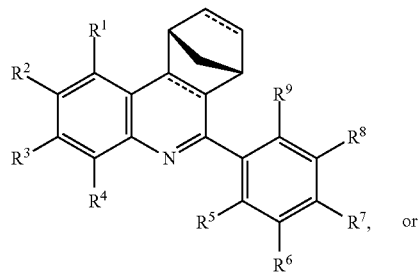

(Ica)

or

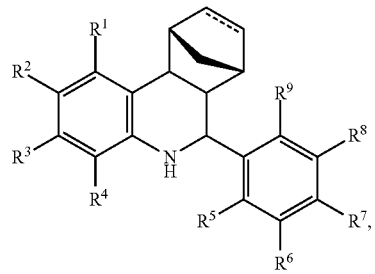

(Icb)

or a pharmaceutically acceptable salt thereof, wherein $R^1$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

$R^2$ is selected from the group consisting of hydrogen, fluoro, bromo, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —S(O)$_z$R$^{1D}$, —OC(=O)R$^{1D}$, hydroxy(C$_2$-C$_6$)alkyl, aryl, heteroaryl, heterocyclyl, arylalkyl, (cyclolalkyl)alkyl, (C$_3$-C$_7$)cycloalkyl, (C$_4$-C$_6$) alkyl optionally substituted with up to 5 fluoro, and (C$_2$-C$_6$)alkoxy optionally substituted with up to 5 fluoro;

$R^3$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{1D}$, —C(=O)OR$^{1D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro;

$R^4$ is selected from the group consisting of hydrogen, hydroxy, halo, cyano, nitro, —S(O)$_z$NR$^{1B}$R$^{1C}$, —NHS(O)$_z$NR$^{1B}$R$^{1C}$, —OC(=O)NR$^{1B}$R$^{1C}$, —NHC(=O)NR$^{1B}$R$^{1C}$, —C(=O)NR$^{1B}$R$^{1C}$, —NR$^{1B}$R$^{1C}$, —S(O)$_z$R$^{1D}$, —NHS(O)$_z$R$^{1D}$, —NHC(=O)R$^{1D}$, —OC(=O)R$^{1D}$, —C(=O)R$^{2D}$, —C(=O)OR$^{2D}$, hydroxy(C$_1$-C$_6$)alkyl, aryl, heteroaryl, heterocyclyl, arylalkyl, (cyclolalkyl)alkyl, (C$_3$-C$_7$)cycloalkyl, (C$_1$-C$_6$)alkyl optionally substituted with up to 5 fluoro, and (C$_1$-C$_6$)alkoxy optionally substituted with up to 5 fluoro, wherein $R^2$ or $R^4$ is not hydrogen;

each NR$^{1B}$R$^{1C}$ is independently selected, wherein R$^{1B}$ and R$^{1C}$ are each independently from the group consisting of hydrogen, C$_{1-6}$alkyl, aryl, arylalkyl, cycloalkyl, (cyclolalkyl)alkyl, (R$^{1BB}$R$^{1CC}$N)alkyl, and (R$^{1BB}$R$^{1CC}$N)C(=O)—;

each R$^{1D}$ is independently selected from the group consisting of hydroxy, aryl, heteroaryl, heterocyclyl, arylalkyl, cycloalkyl, cycloalkenyl, (cyclolalkyl)alkyl, (R$^{1BB}$R$^{1CC}$N)alkyl, (C$_1$-C$_6$)alkyl optionally substituted with up to 5 fluoro, and (C₁-C₆)alkoxy optionally substituted with up to 5 fluoro;

each R²ᴰ is independently selected from the group consisting of hydroxy, aryl, heteroaryl, heterocyclyl, arylalkyl, cycloalkyl, cycloalkenyl, (cyclolalkyl)alkyl, (R¹ᴮᴮR¹ᶜᶜN)alkyl, (C₁-C₆)alkyl substituted with up to 5 fluoro, and (C₁-C₆)alkoxy substituted with up to 5 fluoro;

each R¹ᴮᴮR¹ᶜᶜN is independently selected, wherein R¹ᴮᴮ and R¹ᶜᶜ are each independently from the group consisting of hydrogen, C₁₋₆alkylOC(=O)—, C₁₋₆alkyl, C₁₋₆alkylC(=O)—, aryl, arylalkyl, cycloalkyl, and heterocyclyl;

R⁵ is selected from the group consisting of hydrogen, hydroxy, halo, cyano, nitro, —S(O)$_z$NR¹ᴱR¹ᶠ, —NHS(O)$_z$NR¹ᴱR¹ᶠ, —OC(=O)NR¹ᴱR¹ᶠ, —NHC(=O)NR¹ᴱR¹ᶠ, —C(=O)NR¹ᴱR¹ᶠ, —NR¹ᴱR¹ᶠ, —S(O)$_z$R¹ᴳ, —NHS(O)$_z$R¹ᴳ, —NHC(=O)R¹ᴳ, —OC(=O)R¹ᴳ, —C(=O)R¹ᴳ, —C(=O)OR¹ᴳ, hydroxy(C₁-C₆)alkyl, aryl, heteroaryl, heterocyclyl, arylalkyl, (cyclolalkyl)alkyl, (C₃-C₇)cycloalkyl, (C₁-C₆)alkyl optionally substituted with up to 5 fluoro, and (C₁-C₆)alkoxy optionally substituted with up to 5 fluoro;

R⁶ is selected from the group consisting of hydrogen, hydroxy, halo, cyano, nitro, —S(O)$_z$NR¹ᴱR¹ᶠ, —NHS(O)$_z$NR¹ᴱR¹ᶠ, —OC(=O)NR¹ᴱR¹ᶠ, —NHC(=O)NR¹ᴱR¹ᶠ, —C(=O)NR¹ᴱR¹ᶠ, —NR¹ᴱR¹ᶠ, —S(O)$_z$R¹ᴳ, —NHS(O)$_z$R¹ᴳ, —NHC(=O)R¹ᴳ, —OC(=O)R¹ᴳ, —C(=O)R¹ᴳ, —C(=O)OR¹ᴳ, hydroxy(C₁-C₆)alkyl, aryl, heteroaryl, heterocyclyl, arylalkyl, (cyclolalkyl)alkyl, (C₃-C₇)cycloalkyl, (C₁-C₆)alkyl optionally substituted with up to 5 fluoro, and (C₁-C₆)alkoxy optionally substituted with up to 5 fluoro;

R⁷ is selected from the group consisting of hydrogen, hydroxy, halo, cyano, nitro, —S(O)$_z$NR¹ᴱR¹ᶠ, —NHS(O)$_z$NR¹ᴱR¹ᶠ, —OC(=O)NR¹ᴱR¹ᶠ, —NHC(=O)NR¹ᴱR¹ᶠ, —C(=O)NR¹ᴱR¹ᶠ, —NR¹ᴱR¹ᶠ, —S(O)$_z$R¹ᴳ, —NHS(O)$_z$R¹ᴳ, —NHC(=O)R¹ᴳ, —OC(=O)R¹ᴳ, —C(=O)R¹ᴳ, —C(=O)OR¹ᴳ, hydroxy(C₁-C₆)alkyl, aryl, heteroaryl, heterocyclyl, arylalkyl, (cyclolalkyl)alkyl, (C₃-C₇)cycloalkyl, (C₁-C₆)alkyl optionally substituted with up to 5 fluoro, and (C₁-C₆)alkoxy optionally substituted with up to 5 fluoro;

R⁸ is selected from the group consisting of hydrogen, hydroxy, halo, cyano, nitro, —S(O)$_z$NR¹ᴱR¹ᶠ, —NHS(O)$_z$NR¹ᴱR¹ᶠ, —OC(=O)NR¹ᴱR¹ᶠ, —NHC(=O)NR¹ᴱR¹ᶠ, —C(=O)NR¹ᴱR¹ᶠ, —NR¹ᴱR¹ᶠ, —S(O)$_z$R¹ᴳ, —NHS(O)$_z$R¹ᴳ, —NHC(=O)R¹ᴳ, —OC(=O)R¹ᴳ, —C(=O)R¹ᴳ, —C(=O)OR¹ᴳ, hydroxy(C₁-C₆)alkyl, aryl, heteroaryl, heterocyclyl, arylalkyl, (cyclolalkyl)alkyl, (C₃-C₇)cycloalkyl, (C₁-C₆)alkyl optionally substituted with up to 5 fluoro, and (C₁-C₆)alkoxy optionally substituted with up to 5 fluoro;

R⁹ is selected from the group consisting of hydrogen, hydroxy, halo, cyano, nitro, —S(O)$_z$NR¹ᴱR¹ᶠ, —NHS(O)$_z$NR¹ᴱR¹ᶠ, —OC(=O)NR¹ᴱR¹ᶠ, —NHC(=O)NR¹ᴱR¹ᶠ, —C(=O)NR¹ᴱR¹ᶠ, —NR¹ᴱR¹ᶠ, —S(O)$_z$R¹ᴳ, —NHS(O)$_z$R¹ᴳ, —NHC(=O)R¹ᴳ, —OC(=O)R¹ᴳ, —C(=O)R¹ᴳ, —C(=O)OR¹ᴳ, hydroxy(C₁-C₆)alkyl, aryl, heteroaryl, heterocyclyl, arylalkyl, (cyclolalkyl)alkyl, (C₃-C₇)cycloalkyl, (C₁-C₆)alkyl optionally substituted with up to 5 fluoro, and (C₁-C₆)alkoxy optionally substituted with up to 5 fluoro;

each NR¹ᴱR¹ᶠ is independently selected, wherein R¹ᴱ and R¹ᶠ are each independently from the group consisting of hydrogen, C₁₋₆alkyl, aryl, arylalkyl, cycloalkyl, (cyclolalkyl)alkyl, (R¹ᴱᴱR¹ᶠᶠN)alkyl, and (R¹ᴱᴱR¹ᶠᶠN)C(=O)—;

R¹ᴳ is independently selected from the group consisting of hydroxy, aryl, heteroaryl, heterocyclyl, arylalkyl, cycloalkyl, cycloalkenyl, (cyclolalkyl)alkyl, (R¹ᴱᴱR¹ᶠᶠN)alkyl, (C₁-C₆)alkyl optionally substituted with up to 5 fluoro, and (C₁-C₆)alkoxy optionally substituted with up to 5 fluoro;

each R¹ᴱᴱR¹ᶠᶠN is independently selected, wherein R¹ᴱᴱ and R¹ᶠᶠ are each independently from the group consisting of hydrogen, C₁₋₆alkylOC(=O)—, C₁₋₆alkyl, C₁₋₆alkylC(=O)—, aryl, arylalkyl, cycloalkyl, and heterocyclyl; and each dashed line is an optional double bond.

10. A compound having the structure:

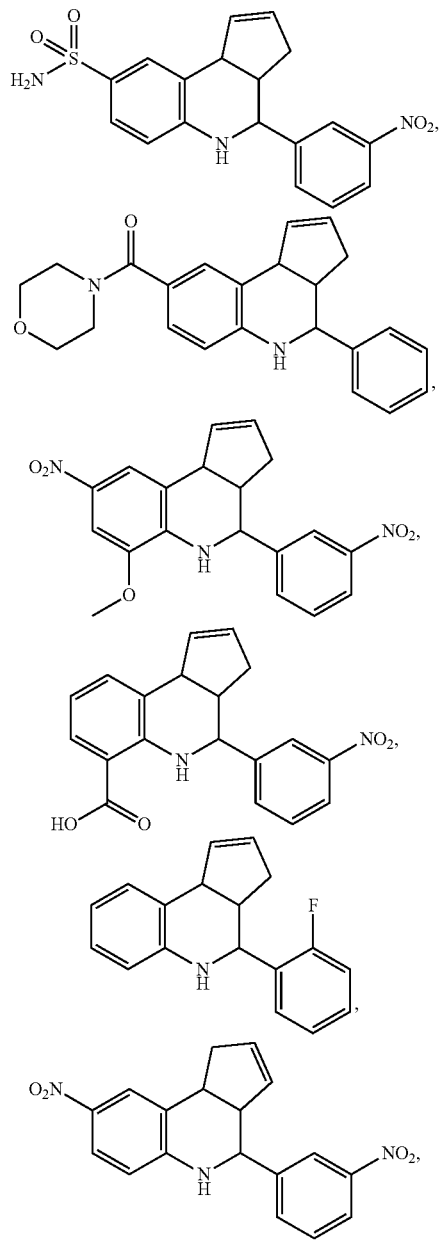

-continued
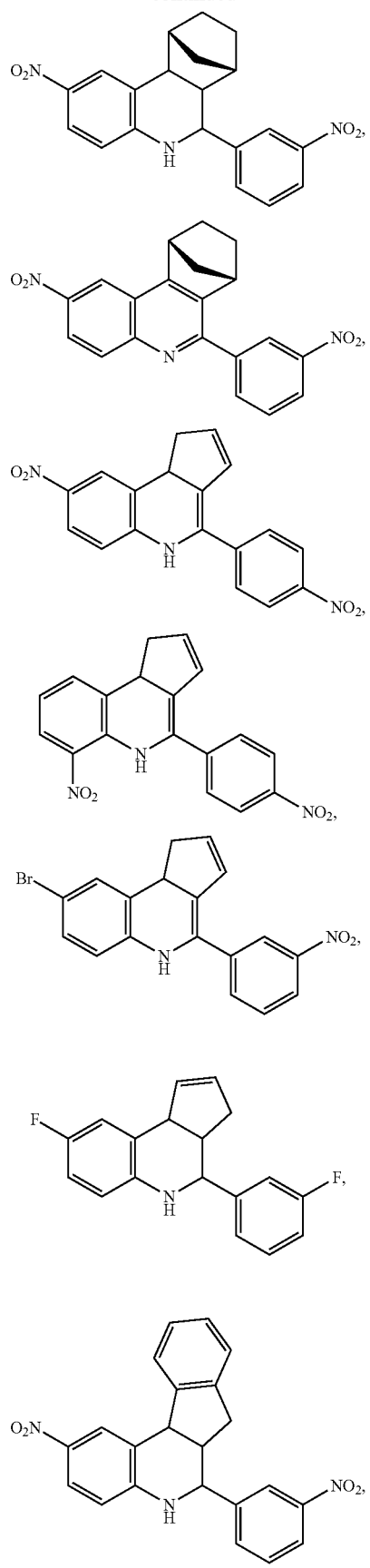
-continued
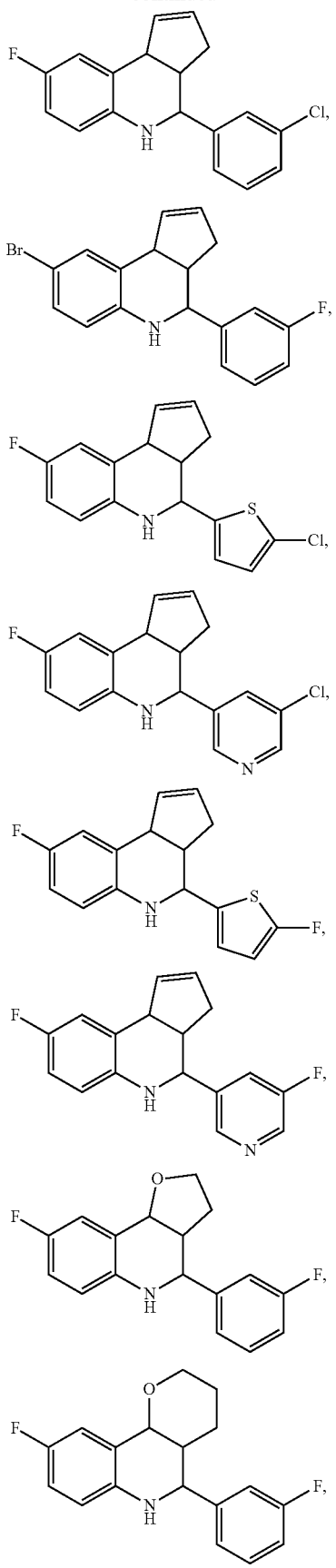

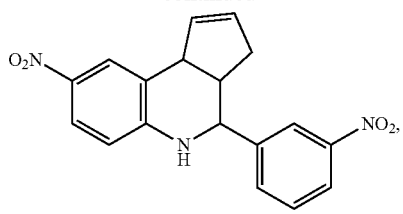
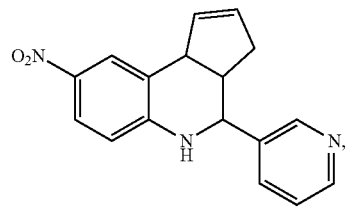
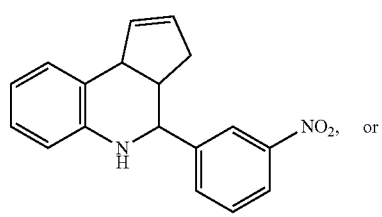
or
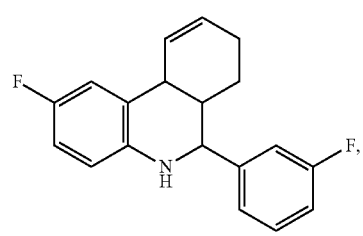
or a pharmaceutically acceptable salt thereof.
11. The compound of claim 10 having the structure:
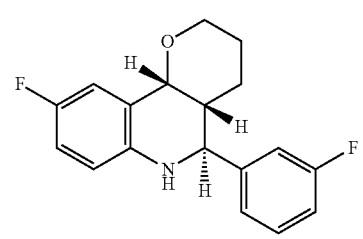
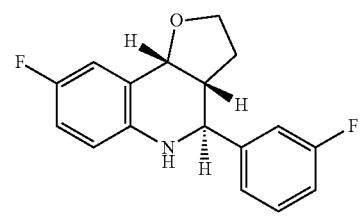
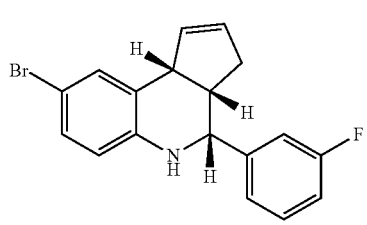
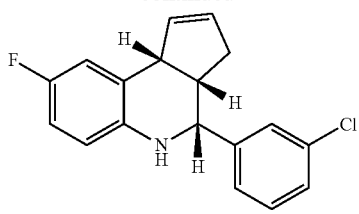
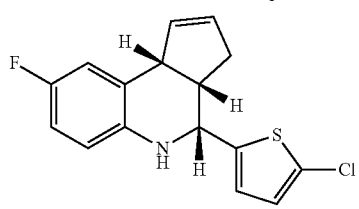
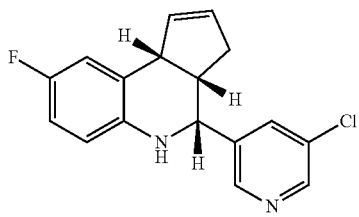
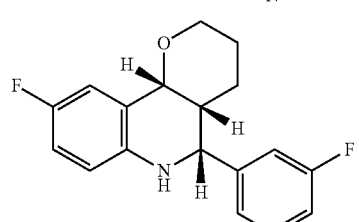
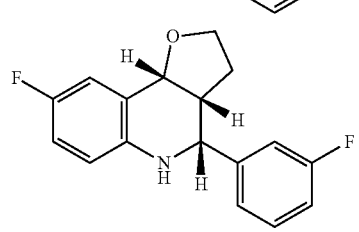
or a pharmaceutically acceptable salt thereof.
12. A pharmaceutical composition comprising a pharmaceutically acceptable excipient, and a compound, wherein the compound is:
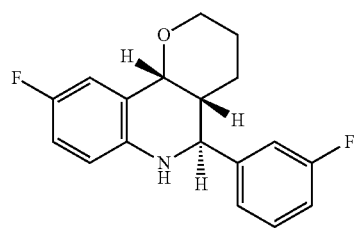
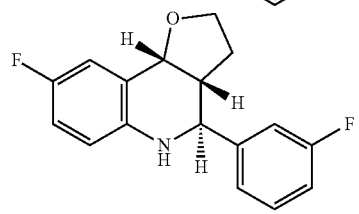

-continued
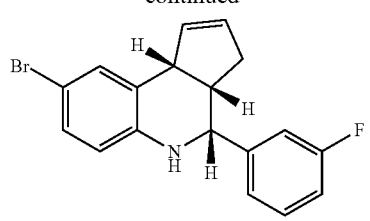
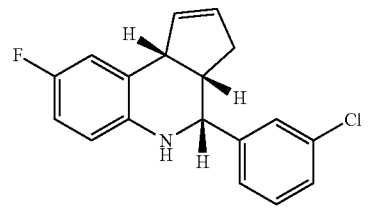
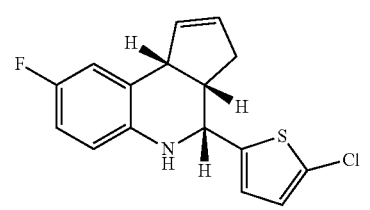
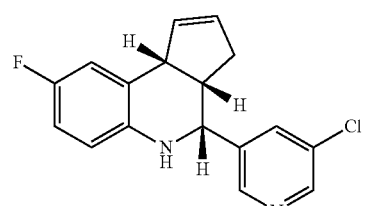
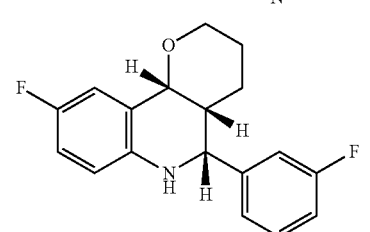
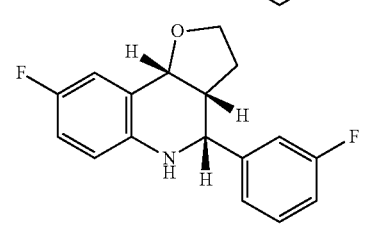
or a pharmaceutically acceptable salt thereof.
13. The method of claim 1, wherein the compound is:
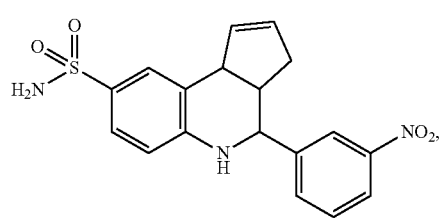
-continued
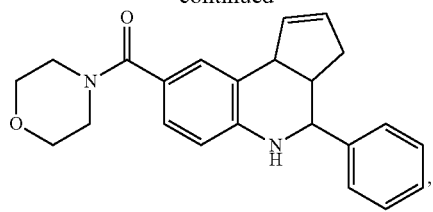
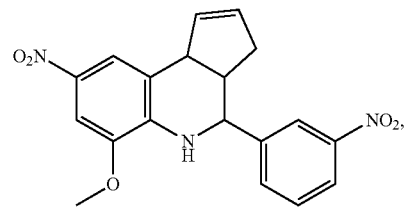
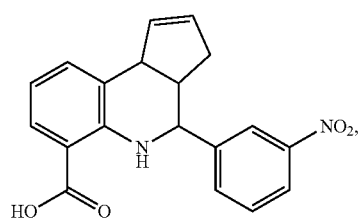
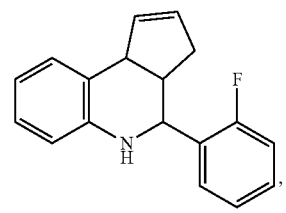
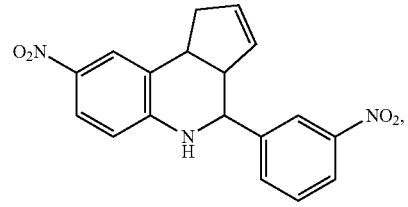
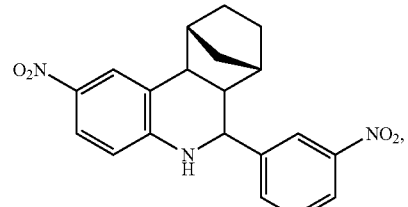
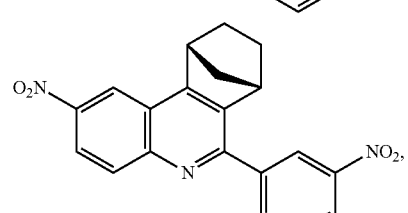

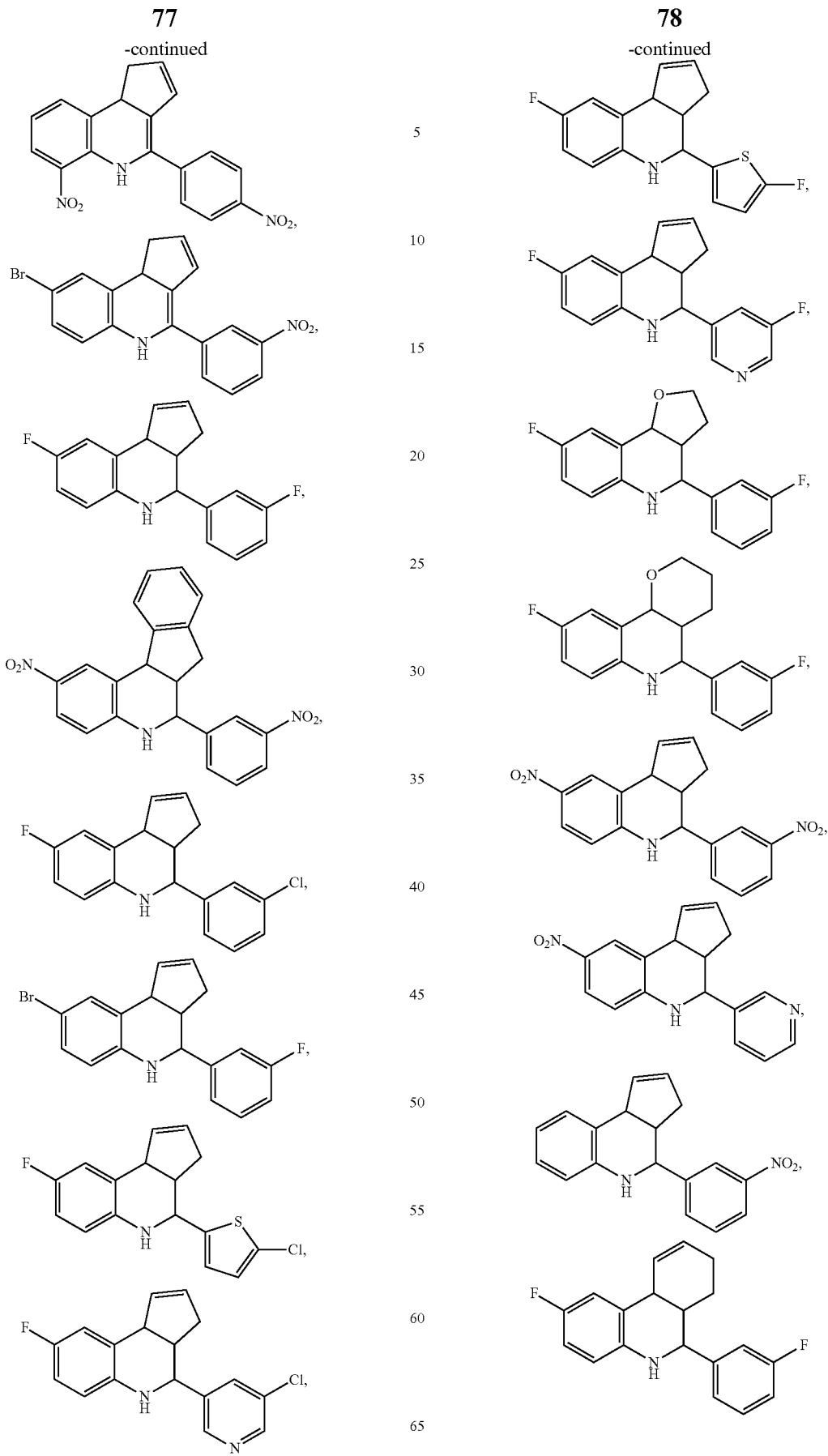
or a pharmaceutical acceptable salt thereof.

14. The method of claim 1, wherein the compound is:
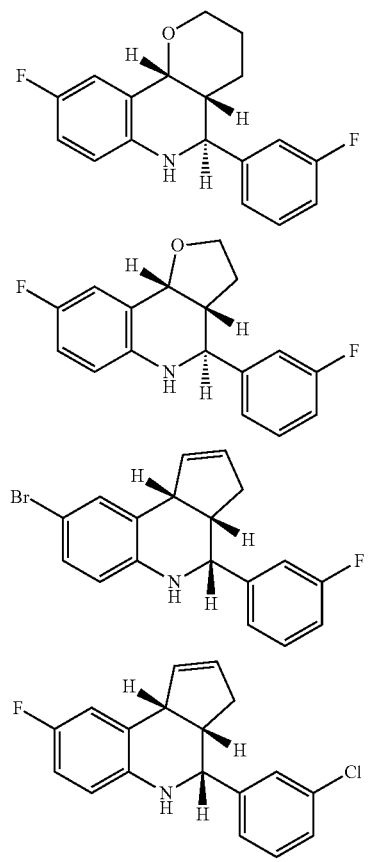
-continued
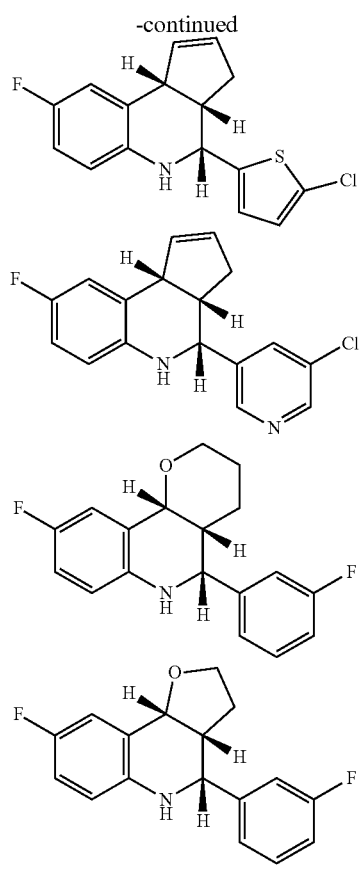
or a pharmaceutically acceptable salt thereof.
* * * * *